US012667845B2

(12) United States Patent (10) Patent No.: US 12,667,845 B2

Cucchi et al. (45) **Date of Patent: \*Jun. 30, 2026**

(54) CARTRIDGE FOR SAMPLE PREPARATION AND MOLECULE ANALYSIS, CARTRIDGE CONTROL MACHINE, SAMPLE PREPARATION SYSTEM AND METHOD USING THE CARTRIDGE

(71) Applicant: STMICROELECTRONICS S.r.l., Agrate Brianza (IT)

(72) Inventors: Davide Cucchi, Brugherio (IT); Marco Angelo Bianchessi, Melzo (IT); Alessandro Cocci, Rovellasca (IT); Lillo Raia, Desio (IT); Lorenzo Bruno, Masera (IT); Nadia Serina, Monza (IT); Marco Cereda, Segrate (IT); Danilo Pirola, Bussero (IT); Pietro Ferrari, Piacenza (IT); Francesco Ferrara, Monteroni di Lecce (IT); Alessandro Paolo Bramanti, Maglie (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 451 days.

This patent is subject to a terminal disclaimer.

(21) Appl. No.: 17/671,382

(22) Filed: Feb. 14, 2022

(65) Prior Publication Data

US 2022/0161259 A1 May 26, 2022

Related U.S. Application Data

(63) Continuation of application No. 16/224,626, filed on Dec. 18, 2018, now Pat. No. 11,278,897.

(30) Foreign Application Priority Data

Dec. 28, 2017 (IT) ........................ 102017000150521

(51) Int. Cl.
B01L 3/00 (2006.01)
C12Q 1/6806 (2018.01)
G01N 1/34 (2006.01)

(52) U.S. Cl.
CPC ... B01L 3/502753 (2013.01); B01L 3/502715 (2013.01); B01L 3/502723 (2013.01);
(Continued)

(58) Field of Classification Search
CPC ......... B01L 3/502753; B01L 3/502715; B01L 3/502723; B01L 3/50273; B01L 3/502738;
(Continued)

(56) References Cited

U.S. PATENT DOCUMENTS 4,671,486 A 6/1987 Giannini
5,163,920 A 11/1992 Olive
(Continued)

FOREIGN PATENT DOCUMENTS

CN 101218032 A 7/2008
CN 101446356 A 6/2009
(Continued)

OTHER PUBLICATIONS

Fang Liang, "Polymer Science in Pharmaceutics," China Medical Science and Technology Press; China; Aug. 31, 2015; pp. 140-142 (5 pages), (with concise explanation of relevance).
(Continued)

*Primary Examiner* — Rebecca M Fritchman

(74) *Attorney, Agent, or Firm* — Seed IP Law Group LLP

(57) ABSTRACT

A sample treatment and molecule analysis cartridge is configured to be mounted in a treatment machine vertically. The cartridge has a sample inlet opening, a fluidic inlet, and a fluidic outlet. The cartridge houses an extraction chamber extending vertically from the sample inlet opening and
(Continued)

connected to the fluidic inlet; a waste chamber extending vertically, alongside the extraction chamber; and a collector extending along the extraction chamber and the waste chamber and having a smaller height than the extraction chamber and the waste chamber. A fluidic circuit connects together the extraction chamber, the waste chamber, the collector, the fluidic inlet, and the fluidic outlet, and is configured to connect the fluidic outlet to vent openings of the extraction chamber, the waste chamber, and the collector, and to connect the bottom end of the extraction chamber to the fluidic inlet, the waste chamber, and the collector.

20 Claims, 46 Drawing Sheets

(52) U.S. Cl.
CPC ..... *B01L 3/50273* (2013.01); *B01L 3/502738* (2013.01); *C12Q 1/6806* (2013.01); *B01L 2200/026* (2013.01); *B01L 2200/0621* (2013.01); *B01L 2200/0668* (2013.01); *B01L 2200/10* (2013.01); *B01L 2300/022* (2013.01); *B01L 2300/044* (2013.01); *B01L 2300/0681* (2013.01); *B01L 2300/0816* (2013.01); *B01L 2300/087* (2013.01); *B01L 2400/043* (2013.01); *B01L 2400/0487* (2013.01); *B01L 2400/049* (2013.01); *B01L 2400/0677* (2013.01); *G01N 1/34* (2013.01)

(58) Field of Classification Search
CPC ....... B01L 2200/026; B01L 2200/0621; B01L 2200/0668; B01L 2200/10; B01L 2300/022; B01L 2300/044; B01L 2300/0681; B01L 2300/0816; B01L 2300/087; B01L 2400/043; B01L 2400/0487; B01L 2400/049; B01L 2400/0677; B01L 3/5027; C12Q 1/6806; C12Q 1/686; G01N 1/34; G01N 33/536; G01N 33/54326; G01N 33/569
See application file for complete search history.

(56) References Cited

U.S. PATENT DOCUMENTS

| | | | |
|---|---|---|---|
| 5,863,024 A | 1/1999 | Blind et al. | |
| 8,137,905 B2 | 3/2012 | Brauner et al. | |
| 8,642,293 B2 | 2/2014 | Sarofim et al. | |
| 8,840,848 B2 | 9/2014 | Kraihanzel | |
| 9,200,315 B2 | 12/2015 | Jung et al. | |
| 9,927,425 B2 | 3/2018 | Shin et al. | |
| 2006/0032746 A1 | 2/2006 | Knott et al. | |
| 2006/0163069 A1 | 7/2006 | Prak et al. | |
| 2006/0219308 A1 | 10/2006 | Oh et al. | |
| 2006/0263914 A1 | 11/2006 | Sando et al. | |
| 2007/0014695 A1 | 1/2007 | Yue et al. | |
| 2009/0030342 A1 | 1/2009 | Flanigan et al. | |
| 2009/0137874 A1 | 5/2009 | Cheng et al. | |
| 2009/0155877 A1 | 6/2009 | Iliescu et al. | |
| 2010/0068706 A1* | 3/2010 | Pourahmadi ........... | B01D 15/00 435/6.19 |
| 2010/0167414 A1 | 7/2010 | Bianchessi et al. | |
| 2010/0233824 A1 | 9/2010 | Verhoeckx et al. | |
| 2010/0273258 A1 | 10/2010 | Lannutti et al. | |
| 2010/0294811 A1 | 11/2010 | Akechi et al. | |
| 2010/0311616 A1 | 12/2010 | Ozawa et al. | |
| 2010/0322826 A1 | 12/2010 | Locascio et al. | |
| 2011/0008223 A1* | 1/2011 | Tsao ........................ | B01L 9/527 422/502 |
| 2011/0049401 A1 | 3/2011 | Chung et al. | |
| 2011/0071055 A1 | 3/2011 | Belgrader et al. | |
| 2011/0232832 A1 | 9/2011 | Park et al. | |
| 2012/0016112 A1 | 1/2012 | Pridmore et al. | |
| 2012/0156112 A1 | 6/2012 | Sprague et al. | |
| 2012/0178091 A1 | 7/2012 | Glezer et al. | |
| 2012/0276592 A1 | 11/2012 | Daub et al. | |
| 2012/0322110 A1 | 12/2012 | Gomi et al. | |
| 2013/0079253 A1 | 3/2013 | Belgrader et al. | |
| 2013/0273548 A1 | 10/2013 | Mastromatteo et al. | |
| 2013/0273549 A1 | 10/2013 | Sullivan et al. | |
| 2013/0331298 A1 | 12/2013 | Rea | |
| 2014/0012558 A1 | 1/2014 | Mansi et al. | |
| 2014/0045275 A1 | 2/2014 | Rothacher et al. | |
| 2014/0287955 A1 | 9/2014 | Wende et al. | |
| 2014/0352819 A1 | 12/2014 | Pugliese et al. | |
| 2015/0024436 A1 | 1/2015 | Eberhart et al. | |
| 2015/0153257 A1 | 6/2015 | Olivier et al. | |
| 2015/0182202 A1 | 7/2015 | Wan et al. | |
| 2015/0240289 A1 | 8/2015 | Manage | |
| 2015/0285793 A1 | 10/2015 | Chan et al. | |
| 2016/0047832 A1 | 2/2016 | Gumbrecht et al. | |
| 2016/0109466 A1* | 4/2016 | Wang ................. | G01N 33/5302 435/7.94 |
| 2016/0251698 A1* | 9/2016 | Laermer .............. | C12Q 1/6848 506/9 |
| 2016/0310948 A1 | 10/2016 | Nowakowski et al. | |
| 2017/0002399 A1 | 1/2017 | Eberhart et al. | |
| 2017/0297021 A1 | 10/2017 | Chung et al. | |
| 2017/0327867 A1 | 11/2017 | Dohale et al. | |
| 2018/0257075 A1* | 9/2018 | Yellen .................... | B03C 1/288 |
| 2020/0061621 A1 | 2/2020 | Jebrail et al. | |
| 2021/0394181 A1 | 12/2021 | Cereda et al. | |
| 2023/0039883 A1 | 2/2023 | Bianchessi et al. | |
| 2023/0058091 A1 | 2/2023 | Cereda et al. | |
| 2023/0330672 A1 | 10/2023 | Cucchi et al. | |
| 2024/0307876 A1 | 9/2024 | Cereda et al. | |

FOREIGN PATENT DOCUMENTS

| | | | |
|---|---|---|---|
| CN | 101754813 A | 6/2010 | |
| CN | 103555558 A | 2/2014 | |
| CN | 103849548 A | 6/2014 | |
| CN | 104470635 A | 3/2015 | |
| CN | 104704363 A | 6/2015 | |
| DE | 10 2012 208 074 A1 | 11/2013 | |
| EP | 1878802 A1 | 1/2008 | |
| EP | 1944078 A1 | 7/2008 | |
| EP | 2436446 A1 | 4/2012 | |
| EP | 2940470 A1 | 11/2015 | |
| FR | 2109370 A5 | 5/1972 | |
| WO | 2014/012558 A2 | 1/2014 | |

OTHER PUBLICATIONS

Abbott Molecular, "M2000 Realtime System," downloaded from https://www.molecular.abbott/us/en/products/instrumentation/m2000-realtime-system on Jan. 5, 2018, 6 pages.

BD Molecular Diagnostics, "BD Max™ System," downloaded from http://moleculardiagnostics.bd.com/bd-max-system/ on Jan. 5, 2018, 5 pages.

BioFire®, A Biomérieux Company, "FilmArray® Link Software," downloaded from http://www.biofiredx.com/products/filmarray/filmarray-link-software/ on Jan. 5, 2018, 5 pages.

Cepheid North America, "GeneXpert® IV," downloaded from http://www.cepheid.com/us/cepheid-solutions/systems/genexpert-systems/genespert-iv on Jan. 5, 2018, 2 pages.

Fredrickson et al., "Macro-to-micro interfaces for microfluidic devices," Miniaturisation for Chemistry, Biology, & Bioengineering, Lab Chip 4:526-533, 2004.

Garcia-Cordero et al., "Optically Addressable Single-use Microfluidic Valves by Laser Printer Lithography," Lab Chip 10(20):2680-2687, 2010 (9 pages).

Korivi et al., "A Generic Chip-to-World Fluidic Interconnect System for Microfluidic Devices," 39th Southeastern Symposium on System Theory, Mercer University, Macon, Georgia, Mar. 4-6, pp. 176-180, 2007.

(56) References Cited

OTHER PUBLICATIONS

Lok et al., "Sample loading and retrieval by centrifugation in a closed-loop PCR microchip," Microchimica Acta, 176(3):445-453, 2012.

PerkinElmer, "LabChip EZ Reader 4-Sipper Chip," downloaded from http://www.perkinelmer.com/product/labchip-ez-reader-tm-4-sipper-chip-760394 on Jan. 9, 2018, 2 pages.

Rahbar et al., "Arrayable Microfluidic Valves Based on Rare Earth Permanently Magnetic Polymer for Use in Microfluidic Flow Switching," 18th International Conference on Miniaturized Systems for Chemistry and Life Sciences, San Antonio, Texas, Oct. 26-30, pp. 205-209 2014.

Roche Molecular Diagnostics, "cobas® Liat® System,", downloaded from https://molecular.roche.com/systems/cobas-liat-systems/ on Jan. 5, 2018, 4 pages.

STATDx, "Simple & Fast Syndromic Testing Closer to Care," downloaded from https://www.stat-dx.com/ on Jan. 5, 2018, 4 pages.

Temiz et al., "Lab-on-a-chip devices: How to close and plug the lab?" Microelectronic Engineering 132:156-175, 2015.

Wikipedia, "Capillary action," downloaded from https://en.wikipedia.org/wiki/Capillary_action on Jan. 5, 2018, 5 pages.

U.S. Appl. No. 16/221,152 (now U.S. Pat. No. 11,110,457), filed Dec. 14, 2018, Analysis Unit for a Transportable Microfluidic Device, in Particular for Saiviple Preparation and Molecule Analysis.

U.S. Appl. No. 17/465,732, filed Sep. 2, 2021, Analysis Unit for a Transportable Microfluidic Device, in Particular for Saiviple Preparation and Molecule Analysis.

U.S. Appl. No. 16/226,590, filed Dec. 19, 2018, Solid Reagent Containivient Unit, in Particular for a Transportable Microfluidic Device for Sample Preparation and Molecule Analysis.

U.S. Appl. No. 16/231,272, filed Dec. 21, 2018, Microfluidic Connector Group, Microfluidic Device and Manufacturing Process Thereof, in Particular for a Cartridge for Saiviple Preparation and Molecule Analysis.

U.S. Appl. No. 16/231,251, filed Dec. 21, 2018, Magnetically Controllable Valve and Portable Microfluidic Device Having a Magnetically Controllable Valve, in Particular Cartridge for Sample Preparation And Molecule Analysis.

Prakash et al., "Identification of respiratory pathogen Bordetella Pertussis using integrated microfluidic chip technology," Microfluid Nanofluid 4, 451-456 (2008). https://doi.org/10.1007/s10404-007-0195-y (Year: 2008).

Hitzbleck et al., "Reagents in microfluidics: an 'in' and 'out' challenge," *Chem. Soc. Rev. 42*:8494-8516, 2013. (24 pages).

Casals-Terré et al., "Design, fabrication and characterization of an externally actuated ON/OFF microvalve," *Sensors and Actuators A: Physical, 147*: 600-606, July 2008.

Fuliang, Hu; "Excipient of the Tablet," Mar. 31, 2005; 6 pages.

Gholizadeh et al., "Magnetically Actuated Microfluidic Transistors: Miniaturized Micro-Valves Using Magnetorheological Fluids Integrated With Elastomeric Membranes," *IEEE, Journal of Microelectromechanical Systems*: 1-7, 2016.

Tang et al., "Versatile Microfluidic Platforms Enabled by Novel Magnetorheological Elastomer Microactuators," *Advanced Functional Materials 1705484*: 1-10, 2018.

* cited by examiner 242  248  244  246  236A  244A  235  223  221

241  222  254

236  230A

225

240  245  243A  226  236B

86

2'

240

245

171

236

170

110'

245
236
175
240
172

221
226

226

11

221

12

30A

30B

51

50

33,54

55

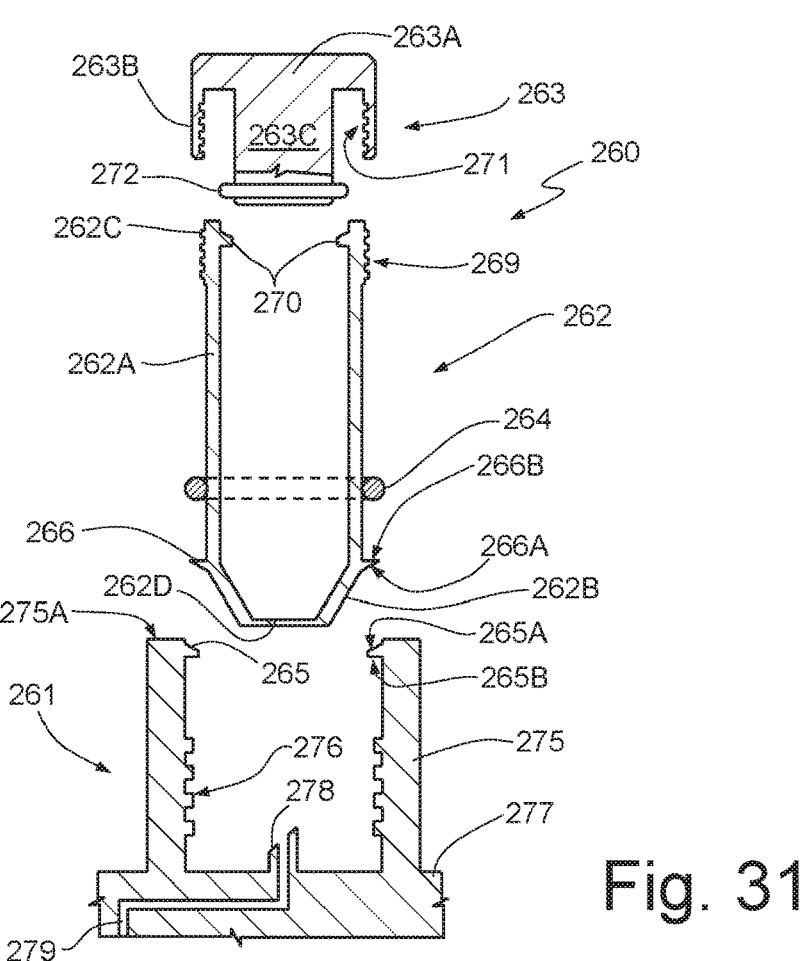
Fig. 31
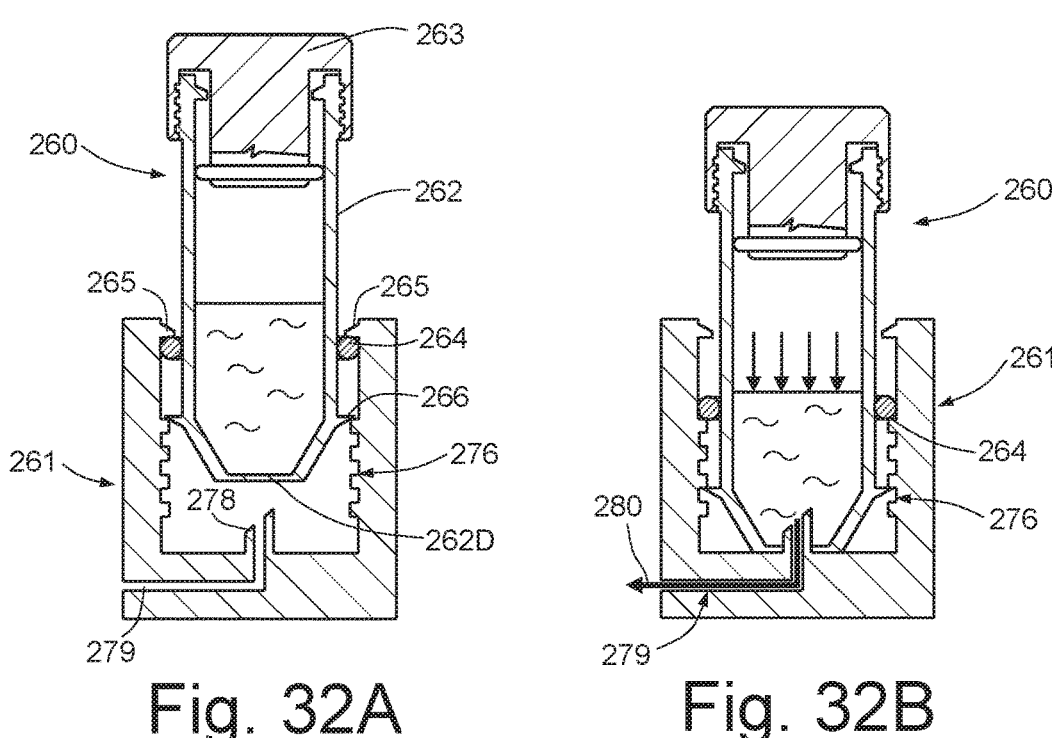
Fig. 32A                    Fig. 32B

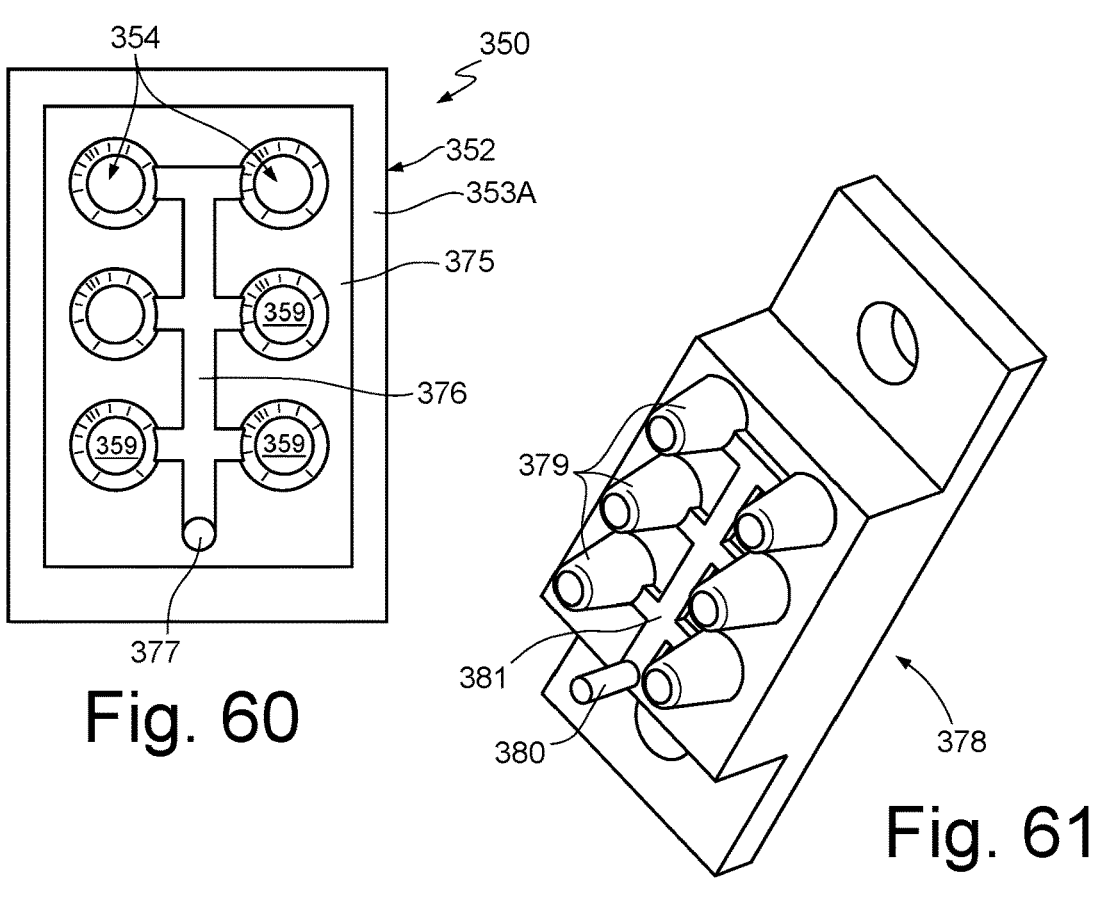
Fig. 60
Fig. 61
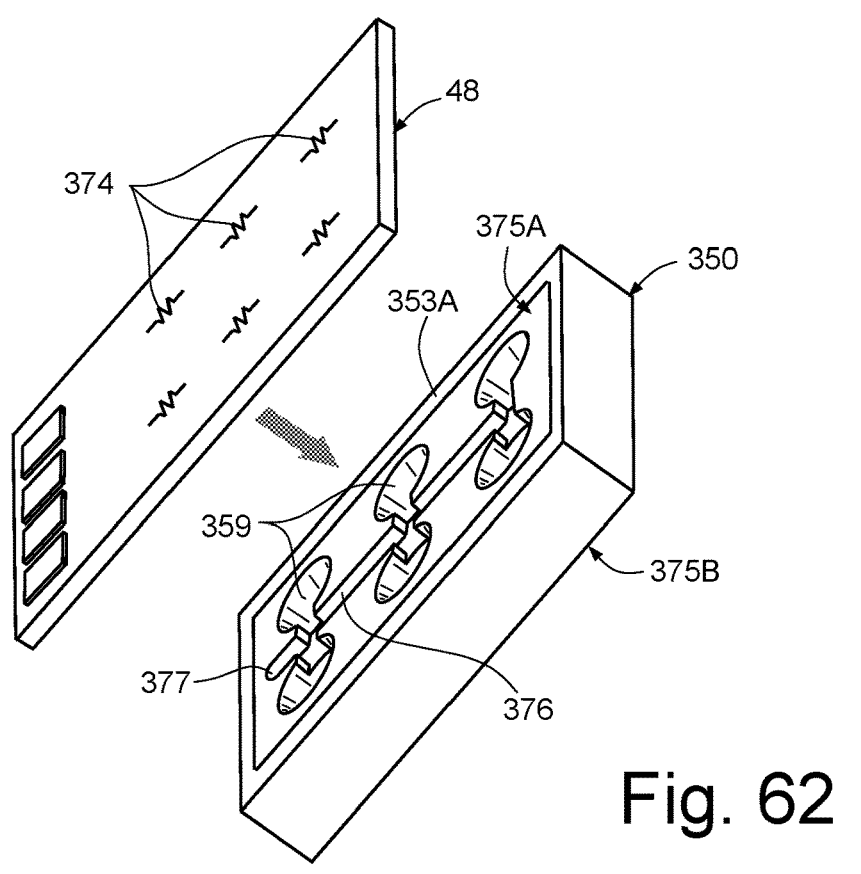
Fig. 62

CARTRIDGE FOR SAMPLE PREPARATION AND MOLECULE ANALYSIS, CARTRIDGE CONTROL MACHINE, SAMPLE PREPARATION SYSTEM AND METHOD USING THE CARTRIDGE

BACKGROUND

Technical Field

The present disclosure relates to a cartridge for sample preparation and molecule analysis, a cartridge control machine, a sample preparation system and method using this cartridge. In particular, the present disclosure relates to the field of so-called Lab-On-a-Chip (LOC) devices, where a single disposable cartridge (also referred to as disposable unit) comprises structures designed to carry out at least some steps of treatment of a sample in order to extract and analyze molecules.

Description of the Related Art

In general, disposable cartridges of the above type are put in a machine that carries out analysis of the substances contained in the cartridge, in general after pre-treatment.

Such systems are of great importance for health, importance that increases in time together with the number of analyses that can be performed in a simple way by a patient alone or with the aid of not particularly skilled persons.

In particular, the above systems enable analysis of biological molecules, such as nucleic acids, proteins, lipids, polysaccharides, etc. They comprise a plurality of operations that start from the raw material, for example a blood sample. These operations may include various degrees of sample pre-treatment, lysis, purification, amplification, and analysis of the resulting product.

For instance, in DNA-based blood tests, the samples are frequently pre-treated by filtration, centrifugation, or electrophoresis to eliminate all the non-nucleated cells. Then the remaining white blood cells are subject to lysis using chemical, thermal, or enzymatic methods to release the DNA that is to be analyzed. This DNA is then purified, to concentrate it and eliminate the other molecules in the cells.

Next, DNA is amplified by an amplification reaction, such as PCR (Polymerase Chain Reaction), LCR (Ligase Chain Reaction), SDA (Strand-Displacement Amplification), TMA (Transcription-Mediated Amplification), RCA (Rolling-Circle Amplification), LAMP (Loop-Mediated Isothermal Amplification) and the like.

The procedures are similar if RNA is to be analyzed, but more emphasis is laid on purification to protect the RNA molecule, which is labile. The RNA is usually copied into DNA (cDNA), and then the analysis proceeds as described for DNA.

Finally, the product of amplification undergoes an analysis, usually based upon the sequence or dimensions or a combination of both. In an analysis by hybridization, for example, amplified DNA is passed over a plurality of detectors formed by individual oligonucleotide probes, which are anchored, for example, on electrodes. If the amplified-DNA strands are complementary to the probes, stable bonds are formed between them, and this hybridization may be read by observing it using a wide range of methods, which include optical or electrical methods.

Other biological molecules are analyzed in a similar way, but typically purification is not followed by amplification, and the detection methods vary as a function of the molecule that is detected. For instance, a common diagnostic system comprises detection of a specific protein by getting it to bind to its antibody or using a specific enzymatic reaction. Lipids, carbohydrates, pharmaceuticals, and small molecules contained in biological fluids are treated in a similar way.

Furthermore, these systems may be used also for the purification of non-biological samples, such as water samples, and for the analysis of non-biological molecules.

The discussion is here simplified by focusing on purification and analysis of nucleic acids (DNA and RNA) as example of molecules that can be purified and analyzed using the cartridge that is the subject of the disclosure. However, in general, the present cartridge may be used for any chemical or biological test that has the requisites referred to hereinafter.

As regards the purification step, the treatment is based upon the following passages:

movement and mixing of liquid reagents; and specific capture of the target molecule to be purified using appropriately functionalized magnetic beads.

As regards the analysis step, the treatment is based upon the following elements:

thermal control (even be very precise); and detection using optical methods, such as, purely by way of non-limiting example, fluorescence or chemiluminescence.

Currently, LOC systems for analysis of nucleic acids have two main applications in the field of human diagnostics: quantitative detection of micro-organisms that cause infective diseases, based upon quantification of nucleic acids of the pathogens; and detection of specific short subsections within a human genome, which enables correlation with specific conditions, such as the individual response to pharmaceuticals or the predisposition to illnesses. In the former case, these systems are designed for monitoring health, in stable or emergency conditions (for example, in the case of spread of epidemics). The latter application regards, among the various contexts, prevention of pathological states and molecular medicine and is increasing in value over time, since the research in progress finds increasing correlations between the DNA/RNA sequences and their functions. As a whole, the market for the two applications is expected to exceed some ten billion dollars in the next few years.

Current systems for analysis of nucleic acids are usually based upon the PCR procedure. This step is typically used in order to obtain a sufficient amount of target nucleic acids to be analyzed even starting from small samples of biological material. PCR moreover enables simplification and reduction of the operations of purification of the nucleic acids to be examined since the useful amplified material considerably exceeds the starting material, as well as possible material (such as non-nucleated cells) not useful for analysis.

Execution of PCR typically employs a specific prior preparation of the biological samples in order to concentrate the nucleic acids, increasing the sensitivity, and to eliminate substances in the biological samples that would inhibit PCR.

With the technique referred to as real-time PCR, PCR is monitored in real time during amplification, and this enables quantification of the strands of target nucleic acids based upon amplification curves. To this end, for example, the material is amplified in presence of oligonucleotide probes labelled in various ways. If the strands of the amplified target nucleic acids are complementary to the oligonucleotide probes, in specific conditions of temperature a stable bond is formed between them (hybridization). The hybridized material may be detected in various ways, for example in an optical or electrochemical way.

Lab-On-a-Chip devices are very promising for performing PCR or real-time PCR, in particular in order to obtain fast, automated, and inexpensive tests even in non-hospital environments. However, many current systems load the cartridge with samples already treated (for example, with DNA/RNA already extracted from the biological sample). This causes the analysis operations to be more complex due to preliminary treatments, which frequently are done by specialized persons.

It is noted that the ensuing discussion regards purification of nucleic acids and their detection through real-time PCR amplification, as example of use of the present system. However, the present disclosure may be applied to other chemical or biological tests.

BRIEF SUMMARY

One or more embodiments of the present disclosure provide solutions that simplify treatment and analysis of samples.

According to the present disclosure, a cartridge, a machine, a system, and a method for sample preparation and molecule analysis are provided.

BRIEF DESCRIPTION OF THE SEVERAL VIEWS OF THE DRAWINGS

For a better understanding of the present disclosure some embodiments thereof are now described, purely by way of non-limiting example, with reference to the attached drawings, wherein:

FIG. 31 shows a cross-section, exploded view of a container for collecting samples, according to one aspect of the present disclosure;

FIGS. 32A and 32B show steps of fixing the container of FIG. 31 in a support;

FIGS. 57A-57C are cross-sections of the solid-reagent containment unit of FIG. 52A in an operative step of a microfluidic device;

FIG. 58 is a perspective view of a different solid-reagent containment unit, which may be applied to the cartridge 2 or 2' of FIGS. 4-6 and 13-15, respectively;

FIG. 59 shows the containment unit of FIG. 58 applied to a part of the cartridge 2' of FIGS. 13-15;

FIG. 60 is a top plan view of a different embodiment of the containment unit of FIG. 58, which may be applied to the cartridge 2 or 2' of FIGS. 4-6 and 13-15, respectively;

FIG. 61 is a perspective view of an embossing tool used for forming the containment unit of FIG. 60;

FIG. 62 is a perspective view of the containment unit of FIG. 60;

DETAILED DESCRIPTION

The following description relates to a miniaturized (on-chip) cartridge, wherein automated extraction of molecules, in particular nucleic acids, is carried out from a biological sample for their analysis. The system implements all the steps envisaged to this end, from loading a biological sample to extracting nucleic acids and collecting them in a collector to enable analysis. The collector may be formed by an analysis chamber, where the nucleic acids may be subject to amplification (where necessary) and detection, for example using real-time PCR. The structure is such that the movement of the liquids (sample, reagents, and products of extraction) is obtained by exploiting the force of gravity and a suction pressure generated by an external pump.

Figure 1:
FIG. 1 shows a block diagram of an embodiment of a system for preparing samples for molecule analysis.

FIG. 1 shows a block diagram of an embodiment of a system 1 for the preparation of biological samples by extracting nucleic acids.

The system 1 comprises a disposable element 2, also referred to hereinafter as cartridge 2, and a control machine 3.

The cartridge 2 comprises a casing 5, having a generally parallelepipedal shape, housing an extraction chamber 6, a waste chamber 7, and a collector 8. In the embodiment described, the collector 8 contains assay reagents and forms an analysis chamber, for example an amplification chamber, also designated hereinafter by 8. The chambers 6, 7, and 8 have respective vent openings 6A, 7A, 8A and are connected together and to the outside world through a fluidic circuit 9, allowing introduction of a sample and preparation reagents into the extraction chamber 6, transfer of the treated sample from the extraction chamber 6 to the analysis chamber 8, as well as collection of waste material in the waste chamber 7. In addition, the fluidic circuit 9 enables an air flow from the inlet to the extraction chamber 6, as well as application of a suction pressure generated by the control machine 3 in the chambers 6-8 in order to transfer the treated sample, the preparation reagents, and the extracted products in the cartridge 2, as described in detail hereinafter with reference to FIGS. 7-10.

Figure 3A:
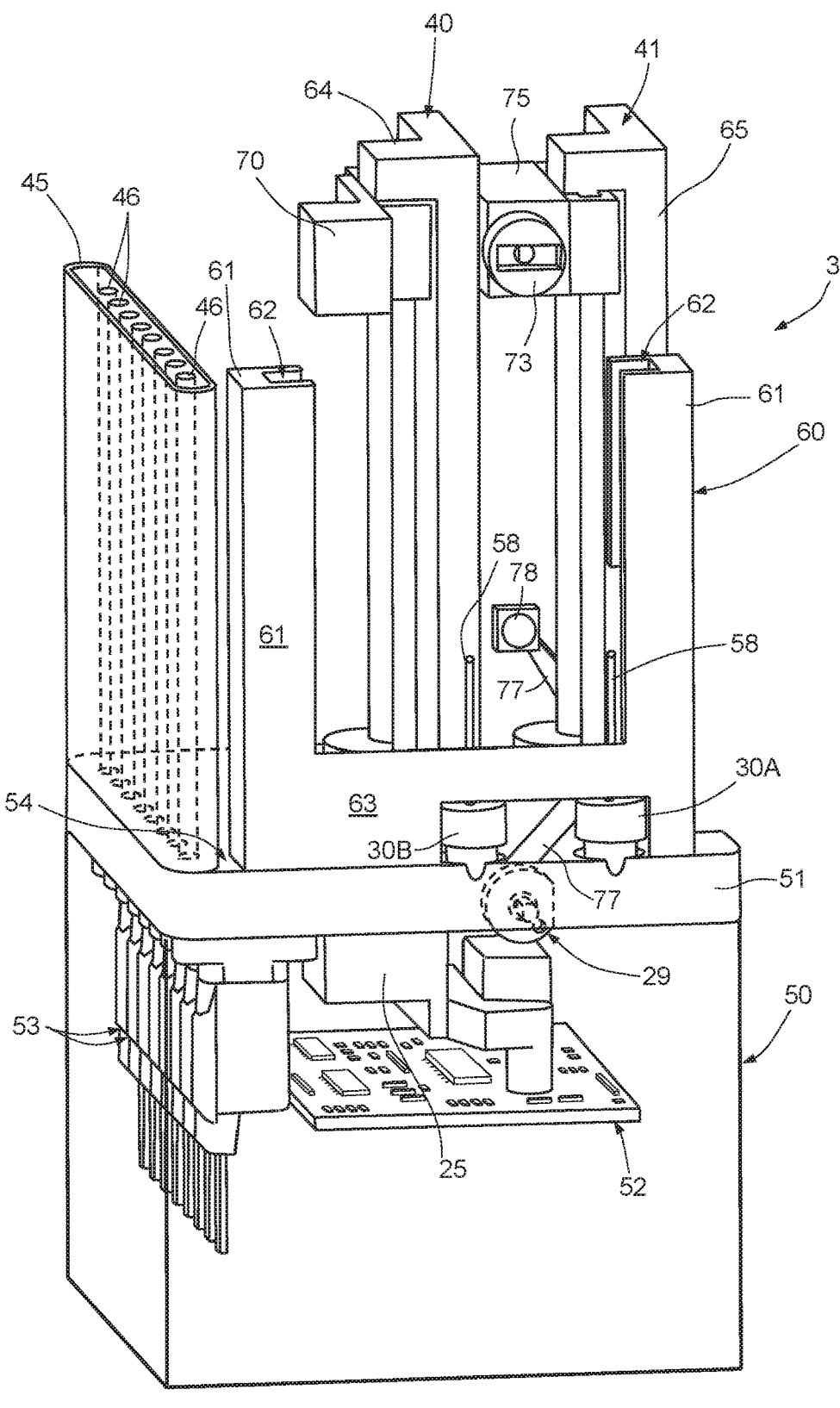
FIG. 3A is a perspective view, with parts removed for reasons of clarity, of an embodiment of the machine of FIG. 2.
Figure 3B:
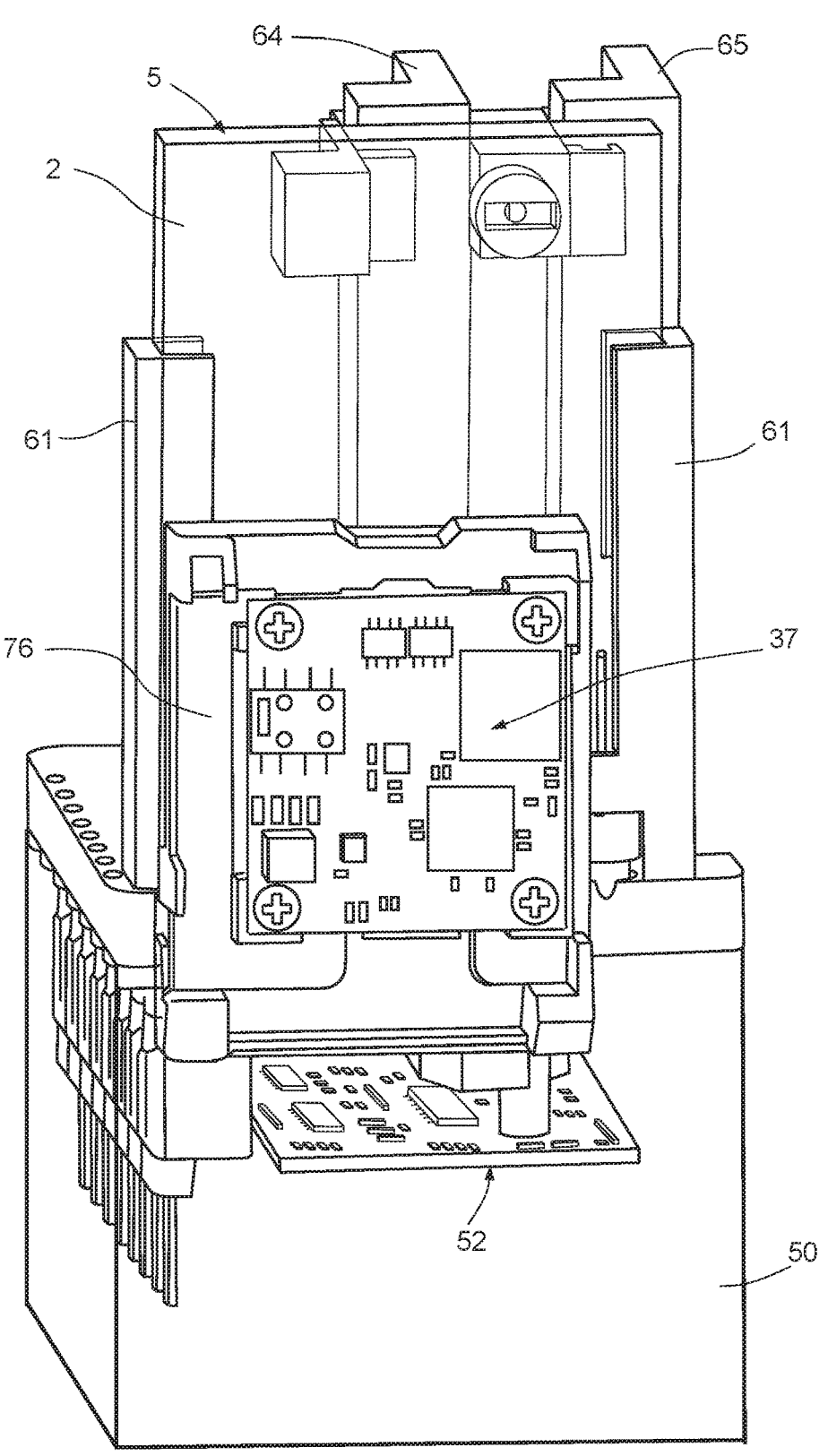
FIG. 3B is a perspective view similar to FIG. 3A, after insertion of a cartridge, showing other parts of the machine.
Figures 4, 4A:
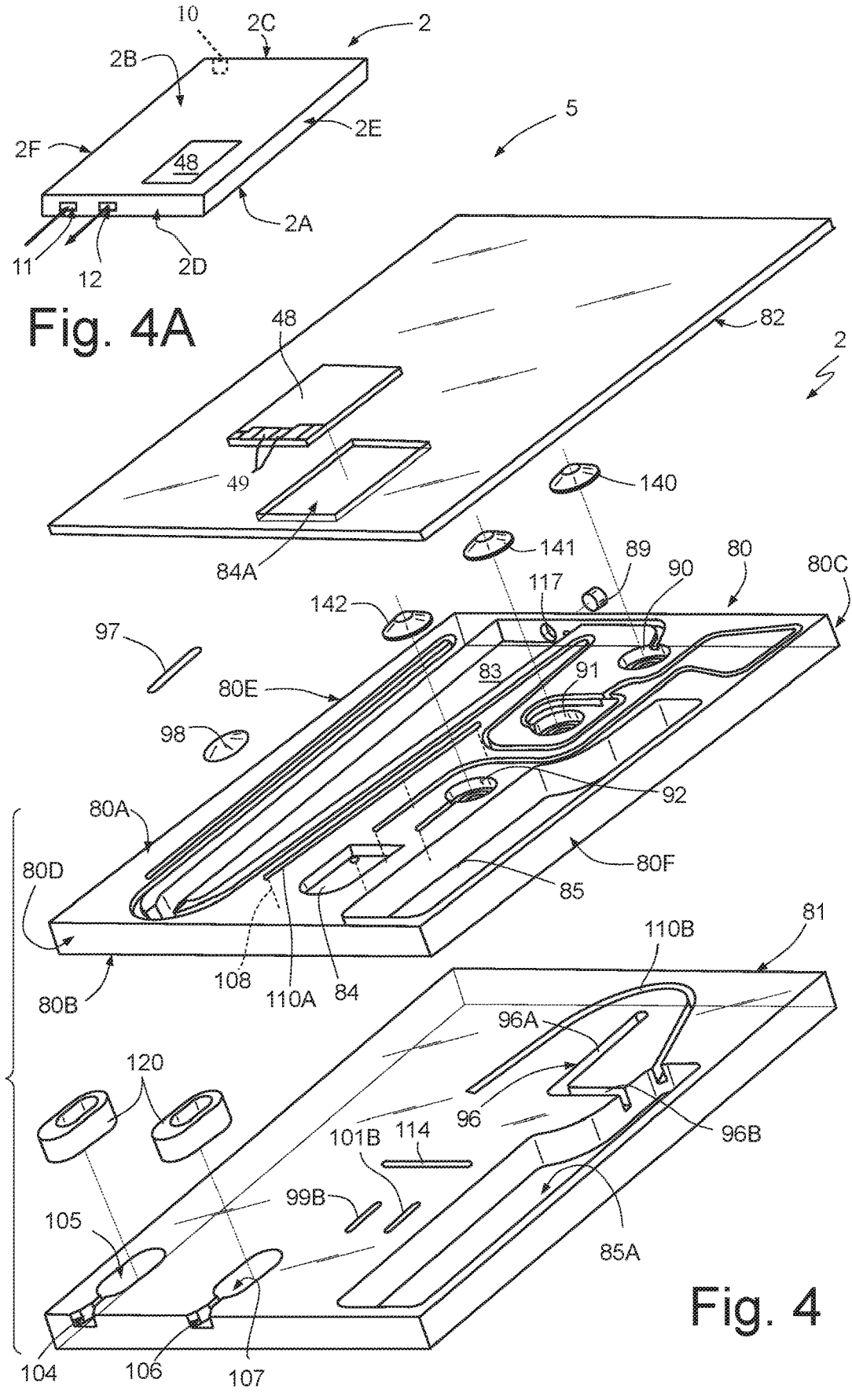
FIGS. 4, 4A, 5, and 6 show, respectively, an exploded view, a perspective view, a front view, and a ghost back view of a first embodiment of a cartridge, which may be used in the system for sample preparation and analysis of FIG. 1.

To this end, the cartridge 2 has a sample inlet 10, arranged on a top face 2C of the cartridge 2 (see also FIG. 4A), a fluidic inlet 11 and a fluidic outlet 12, arranged on a bottom face 2D of the cartridge 2 (see also FIG. 4A). The fluidic inlet 11 and the fluidic outlet 12 are connected to the control machine 3 through a first and a second connection element 30A, 30B, arranged on the control machine 3 and forming, together with the respective fluidic inlet 11 and fluidic outlet 12, a connector group (see also FIGS. 2, 3 and 26-30). In FIG. 1 (where the connections of a pneumatic type are represented with a thin solid line, the connections for the liquids are represented with a thick solid line, and the electrical connections are represented with a dashed and dotted line), the sample inlet 10 is directly connected to the extraction chamber 6, the fluidic inlet 11 (where both air and liquids pass) is connected to the extraction chamber 6 through an inlet channel 13, and the fluidic outlet 12 is connected to the vent opening 7A of the waste chamber 7 through a vent channel 14.

The fluidic circuit 9 of the cartridge 2 further comprises a first pneumatic channel 16, extending between the vent opening 6A of the extraction chamber 6 and the waste chamber 7 and having a first valve 20; a reagent-discharge channel 15, extending between the bottom end of the extraction chamber 6 and an intermediate portion of the waste chamber 7 and having a second valve 21; a product-transfer channel 19, extending between the bottom end of the extraction chamber 6 and the analysis chamber 8; and a second pneumatic channel 17, extending between the vent opening 8A of the analysis chamber 8 and the fluidic outlet 12 and having a third valve 22. Alternatively, the second pneumatic channel 17 may also be connected to the vent channel 14.

The control machine 3 comprises a pump 25, connected to the fluidic outlet 12 of the cartridge 2 through a pneumatic duct 55 and to a ventilation outlet 26 for generating the suction pressure within the cartridge 2; an actuator group 27, facing the cartridge 2, as described hereinafter; a supporting structure 28 for the cartridge 2; the connection elements 30A, 30B, which may be coupled, respectively, to the fluidic inlet 11 and to the fluidic outlet 12 of the cartridge 2; a ventilation inlet 33A, connected to the first connection element 30A through a ventilation line 33 and having a ventilation valve 34; a control unit 35, electrically connected to all the members of the control machine 3; and a memory 36, connected to the control unit 35. The control machine 3 may moreover comprise an optical-detection unit 37, for detecting the reactions in the cartridge 2, and a heating-control and temperature-monitoring unit 38, for controlling the temperature (when necessary, for example by carrying out thermal cycles) during analysis of the treated sample, as described in detail below. Air filters (not shown) may be provided on the ventilation line 33, on the ventilation outlet 26, and on the pneumatic duct 55.

The pump 25 is, for example, of a peristaltic, piezoelectric, syringe, or membrane type, or the like, and generates a suction pressure in the region of 0.05-0.4 atm, for example 0.1 atm in the case of a peristaltic pump and 0.4 atm in the case of a membrane pump.

The actuator group 27 comprises one or more magnetic-valve actuators 40, facing the cartridge 2 for controlling the valves 20-22, as described in greater detail hereinafter with reference to FIGS. 2, 3A, and 3B; an anchor actuator 41, facing the analysis chamber 8, for controlling the movement of a mixing anchor, as described in greater detail hereinafter with reference to FIG. 9; cooling fans 42, also facing the cartridge 2 for reducing the temperature on the basis of any thermal cycles during analysis of the treated sample; and a blocking actuator 43, for trapping magnetic particles, for example magnetic beads, during sample preparation, as described in greater detail hereinafter with reference to FIG. 9.

The control machine 3 moreover carries a reagent-supporting structure 45, accommodating a plurality of containers 46 (see also FIGS. 2 and 3A) and connected to the first connection element 30A.

A heating and temperature-control element 48 is coupled to the analysis chamber 8 and is controlled by the heating-control unit 38 through an electrical-connection element 47. For instance, as described in greater detail hereinafter (FIGS. 4-6), the heating and temperature-control element 48 may be a silicon chip housing integrated resistors.

Figure 2:
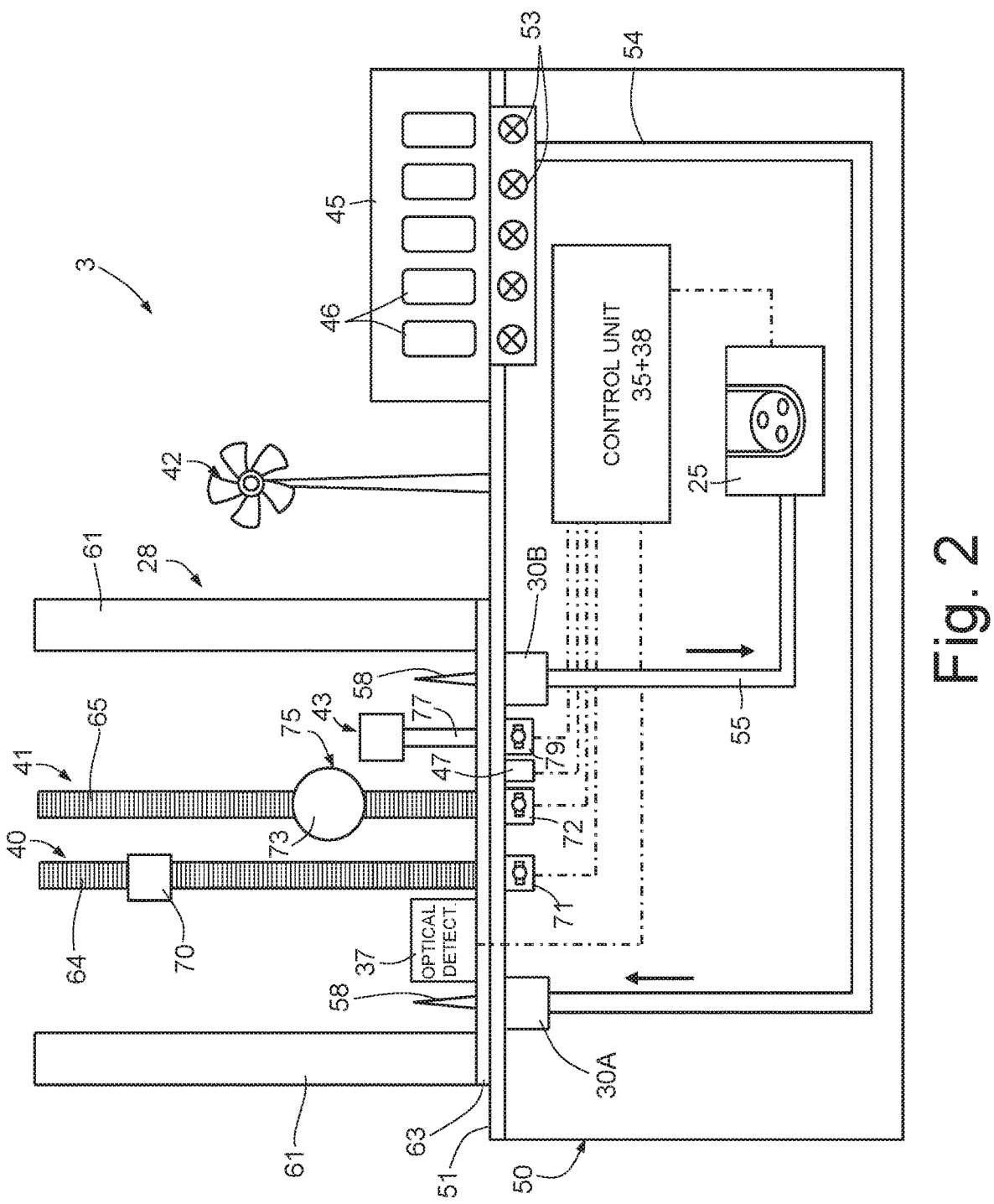
FIG. 2 shows a simplified structural diagram of a control machine belonging to the system of FIG. 1.

FIGS. 2, 3A, and 3B show in a simplified way the structure of the control machine 3. In detail, the control machine 3 comprises a base 50 closed at the top by a manifold structure 51 and housing a printed-circuit board 52 (FIGS. 3A and 3B), which carries the control and processing unit 35 and the heating-control unit 38 (FIG. 2). Moreover, the base 50 accommodates the pump 25; reagent valves 53 connected to the reagent containers 46; a fluidic duct 54, connecting the reagent valves 53 to the first connection element 30A; and the pneumatic duct 55, connecting the pump 25 to the second connection element 30B.

The connection elements 30A and 30B are carried by the manifold structure 51 and each comprise a needle 58, designed to be inserted in the cartridge 2 and to perforate respective gaskets 120 (FIG. 4) in the cartridge 2, as described in greater detail hereinafter with reference to FIGS. 4-6).

The supporting structure 28 is carried by the manifold structure 51 and comprises two U-shaped guides 61 defining mutually facing grooves 62, for allowing insertion of the cartridge 2. The supporting structure 28 further comprises a horizontal bar 63, extending between the guides 61, and from which the needles 58 project upwards. The needles 58 of the connection elements 30A and 30B thus automatically penetrate into the fluidic inlet 11 and the fluidic outlet 12 of the cartridge 2 when the cartridge is inserted in the grooves 62 and pushed down until it rests against the horizontal bar 63.

Furthermore, the manifold structure 51 carries the magnetic valve actuator 40, the anchor actuator 41, the optical-detection unit 37, the blocking actuator 43 (adjacent to the supporting structure 28 so as to face the cartridge 2, when the latter is inserted in the supporting structure 28), as well as the cooling fan 42.

In detail, the magnetic valve actuator 40 comprises a first turret 64 carrying a first magnetic element 70 (for example, a permanent magnet) mobile along the first turret 64. The first turret 64 may be a worm screw rotated about a vertical axis (perpendicular to the manifold structure 51) by a first electric motor 71 in the base 50 (FIG. 2), co-operating with a counter-thread formed on a support of the first magnet or of the first magnetic element 70 so as to be brought each time into a facing position with one of the valves 20-22, according to the operative step of the system 1. Alternatively, the magnetic valve actuator 40 may comprise a plurality of electromagnets, one for each valve 20-22 of the cartridge 2, fixed on the first turret 64 (which, in this case, is formed by a simple supporting vertical structure), facing a respective valve 20-22, and selectively operated when desired (as explained in greater detail hereinafter with reference to FIGS. 7-10).

The anchor actuator 41 comprises a second turret 65, carrying a second magnetic element 73 (for example, a permanent magnet) mobile along the second turret 65 and rotatable about a horizontal axis. In particular, the second magnetic element is mobile along the height of the extraction chamber 6 and governs displacement and rotation of an anchor 97 (FIG. 4) in the extraction chamber 6, for stirring and mixing the liquid present therein, as explained with reference to FIGS. 9 and 45-47. For instance, the second turret 65 may also be a worm screw, extending vertically, rotatably driven by a second electric motor 72 (also arranged in the base 50, FIG. 2) and co-operating with a counter-thread formed on the casing of a third electric motor 75 (FIG. 3A). The third motor 75 is horizontally rotatable and carries the second magnetic element 73, which can thus translate vertically and rotate.

The blocking actuator 43 comprises an arm 77 carrying a permanent magnet 78. The arm 77 is brought to and away from the cartridge 2 by a fourth electric motor 79, fixed to the manifold structure 51. Alternatively, the support 77 may be fixed, and the permanent magnet 78 can be replaced by an electromagnet that is activated/deactivated according to the operative step of sample preparation, as explained in detail hereinafter with reference to FIG. 9.

The optical-detection unit 37 (FIG. 3B), carried by the base 50 through a support 76, is arranged alongside the supporting structure 28, on the opposite side of the cartridge 2 (after insertion of the latter in the guides 61) with respect to the turrets 64-65. The optical-detection unit 37 has the function of detecting the reaction that is occurring (or has occurred) in the analysis chamber 8, for example by optical detection of nucleotide fragments hybridized to corresponding labelled detection fragments, in a per se known manner.

Figure 5:
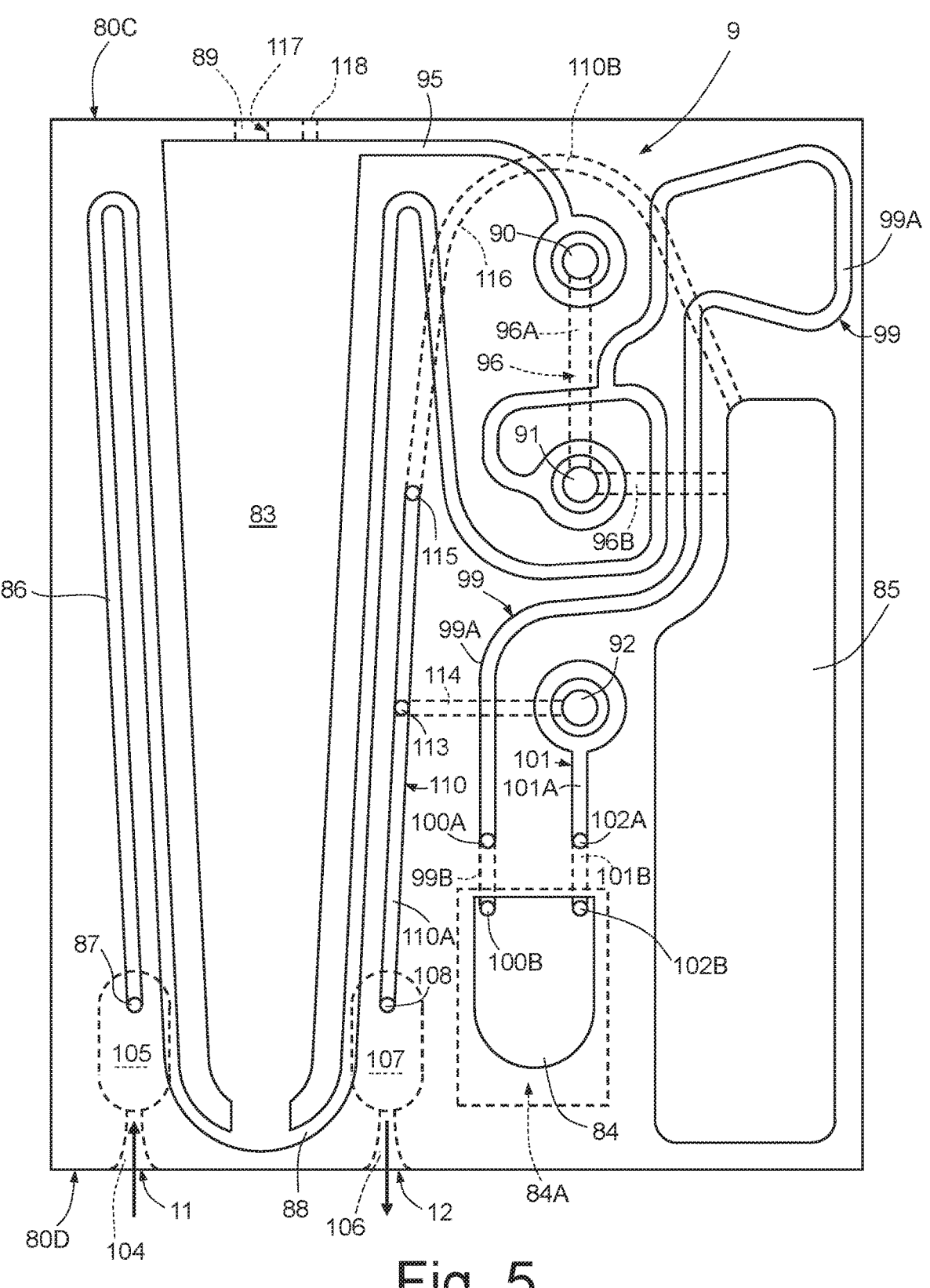
Figure 6:
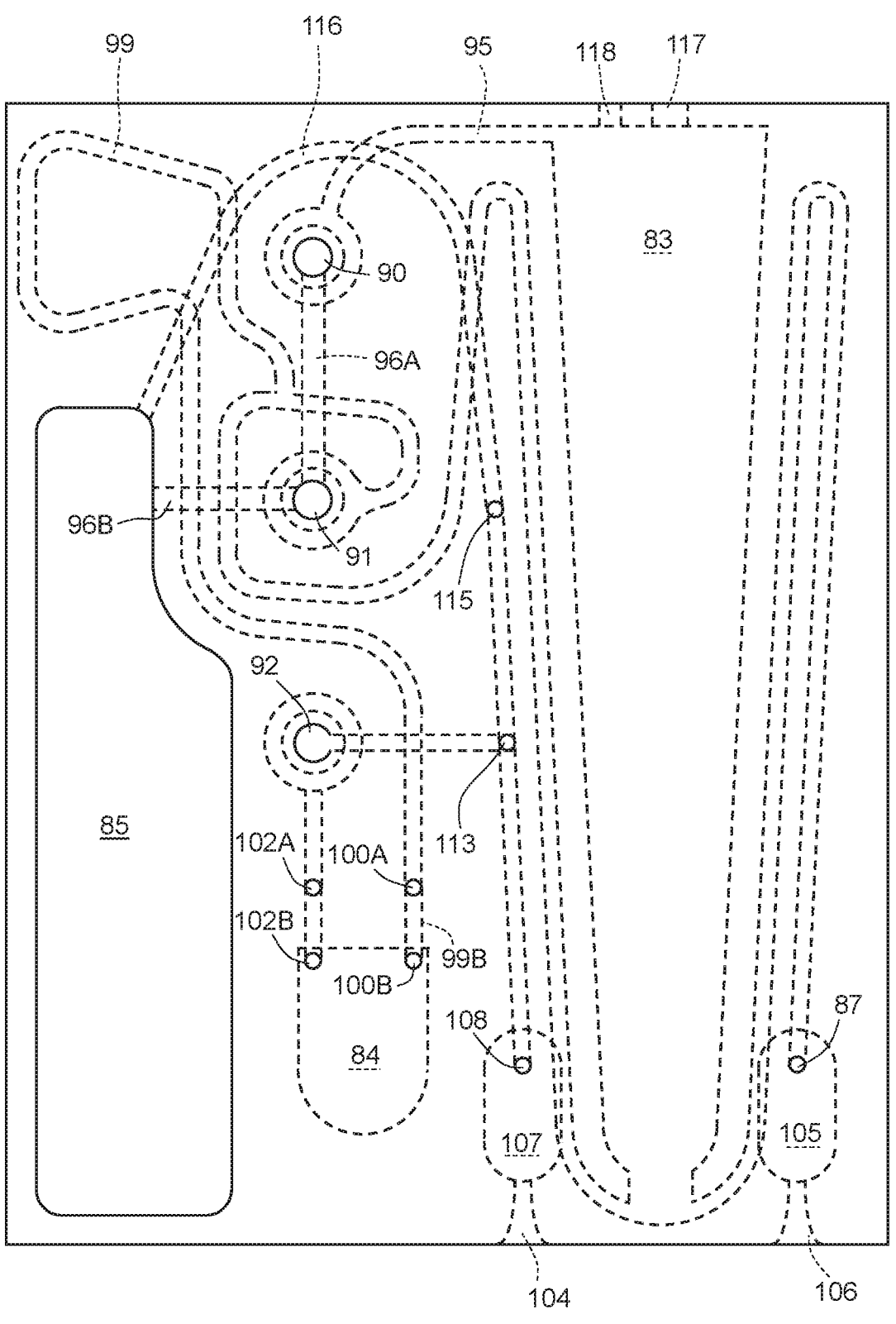

FIGS. 4-6 show a possible implementation of the structure of a cartridge 2 that can be used with the system 1 of FIGS. 1-3. In detail (FIG. 4A), the cartridge 2 has a generally parallelepipedal shape configured to be mounted in the control machine 3 so that its major dimension (hereafter denoted as height H) is arranged vertically. In addition, the cartridge 2 has another of the three dimensions (referred to as thickness T) much smaller than the other two dimensions, and the third dimension, referred to as width L, with an intermediate value. For instance, the cartridge 2 may have H=75 mm, L=50 mm, and T=10 mm.

The cartridge 2 is delimited by a front face 2A, a back face 2B, a top face 2C, a bottom face 2D, a first lateral face 2E, and a second lateral face 2F (where "top" and "bottom" refer to the position of in the control machine 3). The lateral faces 2E, 2F are designed to be inserted in the guides 61, with the front face 2A facing the optical detector 37 and the back face 4B facing the turrets 64 and 65. The bottom face 2D is designed to be introduced in the supporting structure 28 first and to arranged against the horizontal bar 63 of the control machine 3 (FIGS. 2 and 3).

The cartridge 2 is here formed by three parts, all of transparent material: a body 80; a first closing wall 81; and a second closing wall 82, for example a film. The parts 80-82 are bonded together, for example glued or welded thermally, and may have gaskets and sealing means (not shown) to prevent leakage of liquids towards the outside, and to ensure separation of the various channels from each other and isolation from the external environment.

The body 80, for example of molded plastic, has a first main face 80A and a second main face 80B, opposite to each other; and a top face 80C and a bottom face 80D, opposite to each other, forming in part the top face 2C and the bottom face 2D of the cartridge 2. The first closing wall 81 has a face 81A fixed to the second main face 80B of the body 80; the second closing wall 82 is bonded to the first face 80A of the body 80.

The first and second main faces 80A, 80B of the body 80 are shown in detail in FIGS. 5 and 6. The first main face 80A has a plurality of recesses and openings that form, together with other recesses and openings on the face 81A of the first closing wall 81, the chambers 6-8 of FIG. 1 and the channels 14-19. Moreover, the body 80 has a first, a second and a third valve hole 90-92, where the valves 20-22 of FIG. 1 are formed, as described in detail hereinafter. To clarify further the structure, in FIGS. 5 and 6 recesses and cavities formed on the first face 81A of the closing wall 81 are moreover represented dashed.

In detail, the first main face 80A of the body 80 has a first recess (referred to hereinafter as extraction recess 83 since it forms, together with the second closing wall 82, the extraction chamber 6) and a second recess (referred to hereinafter as analysis recess 8 since it forms the analysis chamber 8, as explained hereinafter). The body 80 moreover has a through opening 85 since it forms, together with the closing walls 81, 82, the waste chamber 7, as explained hereinafter.

The extraction recess 83 is generally V-shaped with its bottom portion near the bottom face 80D and its top portion, wider than the bottom portion, near the top face 80C. Thus, by virtue of the use arrangement of the cartridge 2, the extraction chamber 6 has a vertical main dimension, narrower at the bottom and wider at the top. In particular, the extraction recess 83 has an aspect ratio (the ratio between the vertical, larger dimension and the smaller, horizontal dimension) of at least 5, typically approximately 10.

Moreover, the extraction recess 83 accommodates the anchor 97 and a tablet 98 containing the magnetic beads that capture the nucleic acids. In a per se known manner, the tablet 98 may be produced by oven drying or lyophilizing a solution containing the magnetic beads.

The analysis recess 84 has a generally parallelepipedal shape, here like a bag, with bottom rounded corners, and is closed at the sides by a chip, which forms the heating and temperature-control element 48 and is thus designated by 48. The chip 48 is inserted in a through opening 84A (FIG. 4) having a parallelepipedal shape, formed in the second closing wall 82 and sealed in any suitable way. For instance, the chip 48 may be glued to the first main face 80A of the body 80. In practice, the chip 48 and the analysis recess 84 form the collector (analysis chamber) 8. The chip 48 has on the back (on the face 2B of the cartridge 2, FIG. 4A) electrical contacts 49 designed to be electrically coupled with the electrical-connection element 47 on the control machine 3 (FIG. 1).

It is noted that, if the collector 8 is limited to collecting the separated nucleic acids and does not contain assay reagents, the cartridge 2 may be equipped with a further fluidic outlet (not shown), closed, for example, by a perforable gasket, allowing recovery of the treated nucleic acids, for example, using a syringe. In this case, the chip 48 may be missing.

An introduction opening 117 extends from the top face 80C of the body 80 to the extraction recess 83 to form the sample inlet 10 of FIG. 1. The introduction opening 117 may be closed by a plug element 89, represented schematically in FIGS. 4 and 5. Furthermore, the introduction opening 117 may have a screw portion (not shown), for screwing a sample container (not shown either), and/or may have reclosing means, for example as described in detail hereinafter with reference to FIGS. 26-30. A lateral opening 118 may be arranged alongside the introduction opening 117 to enable venting of the extraction recess 83 during introduction of a sample into the sample inlet 10.

The bottom portion of the extraction recess 83 is in fluidic connection with a coiled inlet fluidic recess 86, which extends on a first side (on the left in FIG. 5) of the extraction chamber 6 from the bottom portion as far as near the top face 80C of the body 80 and then from here as far as near the bottom face 80D, where a first through hole 87 connects the first main face 80A to the second main face 80B of the body 80. In practice, the inlet fluidic recess 86 forms the inlet channel 13 of FIG. 1. An output fluidic recess 88, also coiled, extends on a second side of the extraction chamber 6 (on the right in FIG. 5), from the bottom portion as far as near the top face 80C of the body 80 and then from here up to the second valve hole 91, at an intermediate height with respect to the cartridge 2. The second valve hole 91 is vertically aligned (in the in-use position of the cartridge 2) to the first valve hole 90 and to the third valve hole 92, which are arranged, respectively, above the second valve hole 91 (near the top face 80C of the body 80) and below the second valve hole 91. The first, second, and third valve holes 90-92 connect the first main face 80A to the second main face 80B of the body 80 and are normally closed by respective shutters 140-142 represented in ghost view only in FIG. 4. For instance, the shutters 140-142 are elastic elements that undergo deformation under the action of an external magnetic field, opening the respective valve holes 90-92, as described in greater detail hereinafter with reference to FIGS. 38-44, and form, together with the respective valve holes 90-92, the valves 20-22 of FIG. 1.

The first valve hole 90 is fluidically connected to the vent opening 6A of the extraction recess 83 through a first vent recess 95 formed on the first main face 80A, and to an intermediate portion of the waste opening 85 through a first L-shaped fluidic recess 96 formed on the face 81A of the first closing wall 81 (FIG. 4). In practice, the first fluidic recess 96 has a first portion 96A that extends between the first and the second valve holes 90, 91, and a second portion 96B that extends between the second valve hole 91 and the waste recess 85. In practice, the first vent recess 95 and the first fluidic recess 96 form the first pneumatic channel 16 of FIG. 1. In addition, the second portion 96B of the first fluidic recess 96 forms, together with the output fluidic recess 88, the reagent-discharge channel 15 of FIG. 1.

The output fluidic recess 88 is moreover connected to the analysis recess 84 through a product recess 99 (having a first portion 99A, which extends on the first main face 80A of the body 80, and a second portion 99B, which extends on the face 81A of the first closing element 81, FIG. 4) and a first pair of through holes 100A and 100B, which extend in the body 80. The first portion 99A extends from the output fluidic recess 88 towards the top face 80C of the body 80 and then downwards, towards the bottom face 80D, to prevent the products extracted from the sample to be transferred to the waste chamber 7, as explained hereinafter. In practice, the output fluidic recess 88 and the product recess 99 form the product-transfer channel 19 of FIG. 1.

The third valve hole 92 is connected to the vent opening 8A of the analysis recess 84 through a second vent recess 101 and a second pair of through holes 102A, 102B. The second vent recess 101 has a first portion 101A extending on the first main face 80A of the body 80 and a second portion 101B extending on the face 81A of the first closing element 81 (FIG. 4).

A first cavity 104 (FIG. 4) extends on the face 81A of the first closing wall 81 from the bottom face 2D of the cartridge 2 up to a first chamber-like recess 105 facing the first through hole 87 (FIG. 5). A second cavity 106 extends on the face 81A of the first closing wall 81 from the bottom face 2D of the cartridge 2 up to a second chamber-like recess 107 where ends a second through hole 108 formed in the body 80. The first cavity 104, the first chamber-like recess 105, and the first through hole 87 form the fluidic inlet 11; the second cavity 106, the second chamber-like recess 107, and the second through hole 108 form the fluidic outlet 12 of FIG. 1. Gaskets 120, for example of rubber are inserted in the cavities 105, 107 and hermetically seal the fluidic inlet 11 and the fluidic outlet 12 prior to insertion of the cartridge 2 in the control machine 3; the gaskets may be easily be perforated by the needles 58 (FIGS. 2 and 3).

The second through hole 108 places the second chamber-like recess 107 in fluidic communication with a first end of a third vent recess 110, which has a first portion 110A extending on the first main face 80A, partially along the output fluidic recess 88, and a second portion 110B that extends on the first closing wall 81. A third through hole 113 arranged in a middle area of the first portion 110A of the third vent recess 110 connects the third vent recess 110 to the third valve hole 92 through a fourth vent recess 114, which extends on the face 81A of the first closing element 81 (FIG. 4). The first portion 110A of the third vent recess 110, the third through hole 113, the fourth vent recess 114, the second vent recess 101, and the second pair of through holes 102A, 102B, form the second pneumatic channel 17 of FIG. 1.

A fourth through hole 115 connects the first portion 110A to the second portion 110B of the third vent recess 110 (FIG. 4); the second portion 110B of the third vent recess 110 ends into a waste recess 85A on the first closing wall 81. The waste recess 85A on the first closing wall 81 is congruent with and faces the waste opening 85 in the body 80 and forms with this, and with the corresponding portion of the second closing wall 82, the waste chamber 7 of FIG. 1, as already mentioned. The area where the second portion 110B of the third vent recess 110 ends into the waste recess 85A thus forms the vent opening 7A of the waste chamber 7, which is set at the highest point (when the cartridge 2 is inserted in the control machine 3) of the waste chamber 7, to ensure that the liquid cannot exit from the waste chamber 7. In practice, the second portion 110B of the third vent recess 110, the fourth through hole 115, and the third vent recess 110 form the vent channel 14 of FIG. 1.

The waste opening 85 and the waste recess 85A are sized so that the waste chamber 7 has a greater volume than all the spent reagents discharged therein, as explained hereinafter.

In practice, the recesses, holes, and openings 83-117 in the cartridge 2 form the fluidic circuit 9 of FIG. 1 and, as has been mentioned, are arranged so that the displacement of the liquids and the corresponding displacement of the air occur by exploiting the force of gravity and a slight suction pressure applied on the fluidic outlet 12 (recesses 106, 106A, 107, 107A), as described in detail hereinafter with reference to FIGS. 7-10. In particular, FIGS. 7-10 show the movement of fluids in the body 80 in the successive operative steps. For greater clarity, FIGS. 7-10 shows the body 80 in ghost view and the fluidic structures of the first closing wall 81, irrespective whether the recesses, openings, and chambers are arranged on the first main face 80A, on the second main face 80B or on the first closing wall 81.

In detail, the cartridge 2 is inserted in the supporting structure 28 so that the second closing wall 82 faces the turrets 64-65, and the analysis chamber 8 (containing the assay reagents, for example, amplification reagents) faces the optical detector 37. The contacts 49 on the chip 48 thus are brought at the electrical-connection element 47 (FIG. 1) on the control machine 3, thus connecting the chip 48 to the control unit 35. During insertion of the cartridge 2, the needles 58 perforate the gaskets 120, thus connecting the fluidic inlet 11 and the fluidic outlet 12 to the control machine 3. Then, a liquid sample is introduced into the extraction chamber 6. The liquid sample is introduced through the introduction opening 117, for example using a syringe (not shown), which perforates (arrow 150 of FIG. 7) the plug element 89. Alternatively, a container (not shown), as described in greater detail hereinafter with reference to FIGS. 31-37, or a plug such as for a test tube may be screwed on the introduction opening 117 shown. In this step, all the valves 20-22 are closed, and the pump 25 (FIG. 1) is inactive. The liquid sample accumulates by gravity on the bottom of the extraction chamber 6 and fills it partially (typically, less than half full, for example approximately one fifth). After introducing the liquid sample, if necessary, the introduction opening 117 is reclosed.

Figures 7, 8:
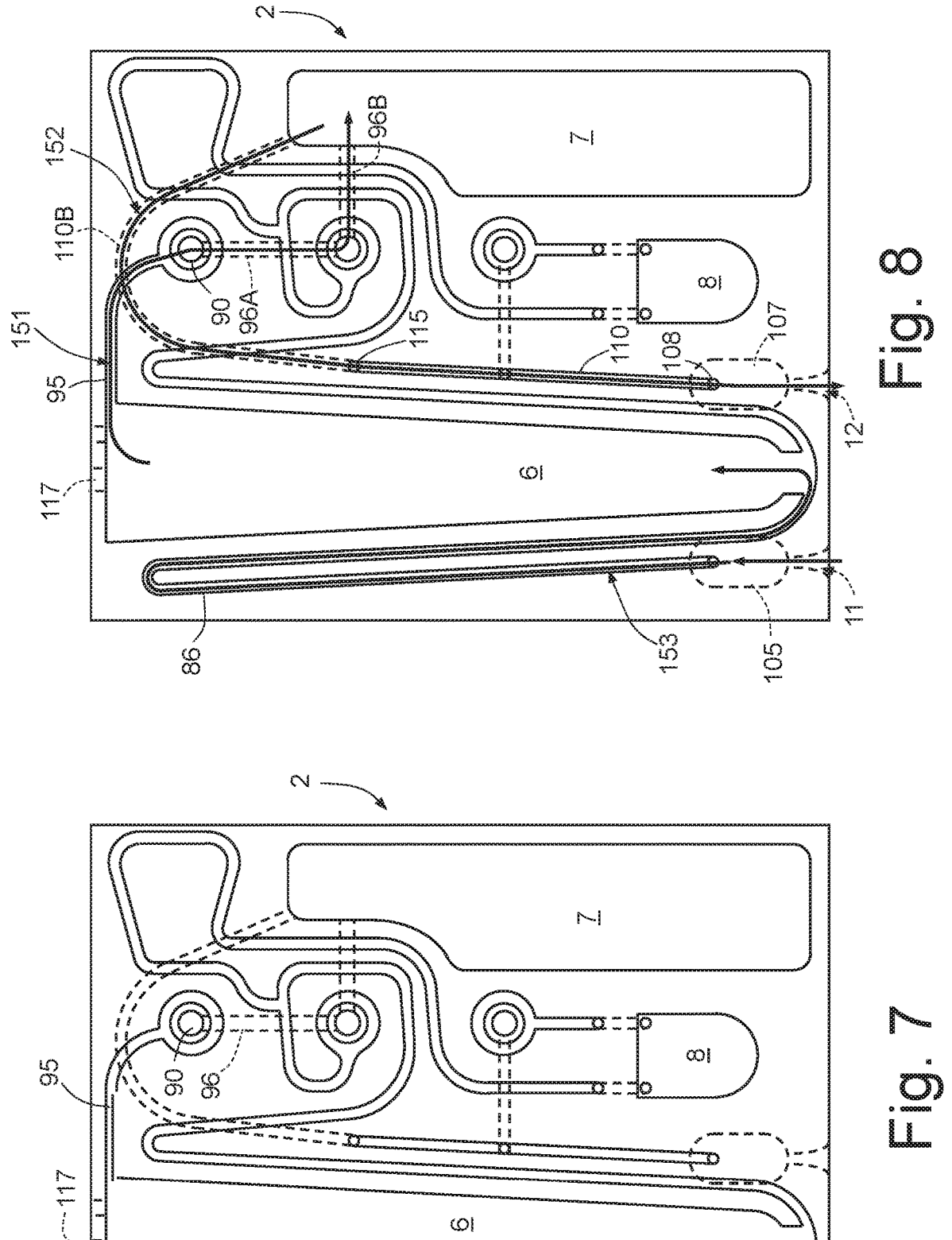
FIGS. 7-10 show the circulation of fluids in successive operative steps of the cartridge of FIGS. 4-6.

Next, FIG. 8, the preparation reagents are introduced into the extraction chamber 6, and the nucleic acids are extracted from the liquid sample in the extraction chamber 6.

To this end, the containers 46 (FIGS. 1-3) are selectively connected in sequence, according to envisaged procedures, to the fluidic inlet 11 through the reagent valves 53 and the first fluidic duct 54 (FIG. 2). In this step, the first valve 20 is opened, by causing deformation of the first shutter 140 (FIG. 4). In this way, the top part of the extraction chamber 6 is connected to the waste chamber 7 through the extraction vent opening 6A, the first vent recess 95, the first valve hole 90, and the first fluidic recess 96, as indicated by the arrow 151. Furthermore, the pump 25 is activated so as to generate a suction pressure in the waste chamber 7, through the fluidic outlet 12, the second chamber-like recess 107, the second through hole 108, the third vent recess 110, the fourth through hole 115, the second portion 110B of the third vent recess 110, and the vent opening 6A, as indicated by the arrow 152. In this way, the preparation reagents at the fluidic inlet 11 are lead, by the suction pressure generated by the pump 25, towards the bottom part of the extraction chamber 6, through the first chamber-like recess 105 and the inlet fluidic recess 86, as indicated by the arrow 153, and the air in the extraction chamber 6 can flow away from the top of the extraction chamber 6 towards the waste chamber 7.

After introducing the first preparation reagent, namely, the lysis liquid, proper lysis is carried out in a per se known manner.

During lysis, the anchor actuator 41 may be operated to cause a repeated vertical movement and rotation of the anchor 97 (FIG. 4) in the extraction chamber 6 in order to stir and mix the lysis liquid (as well as of the magnetic beads capturing the nucleic acids, as described hereinafter with reference to FIGS. 45-47).

Figure 9:
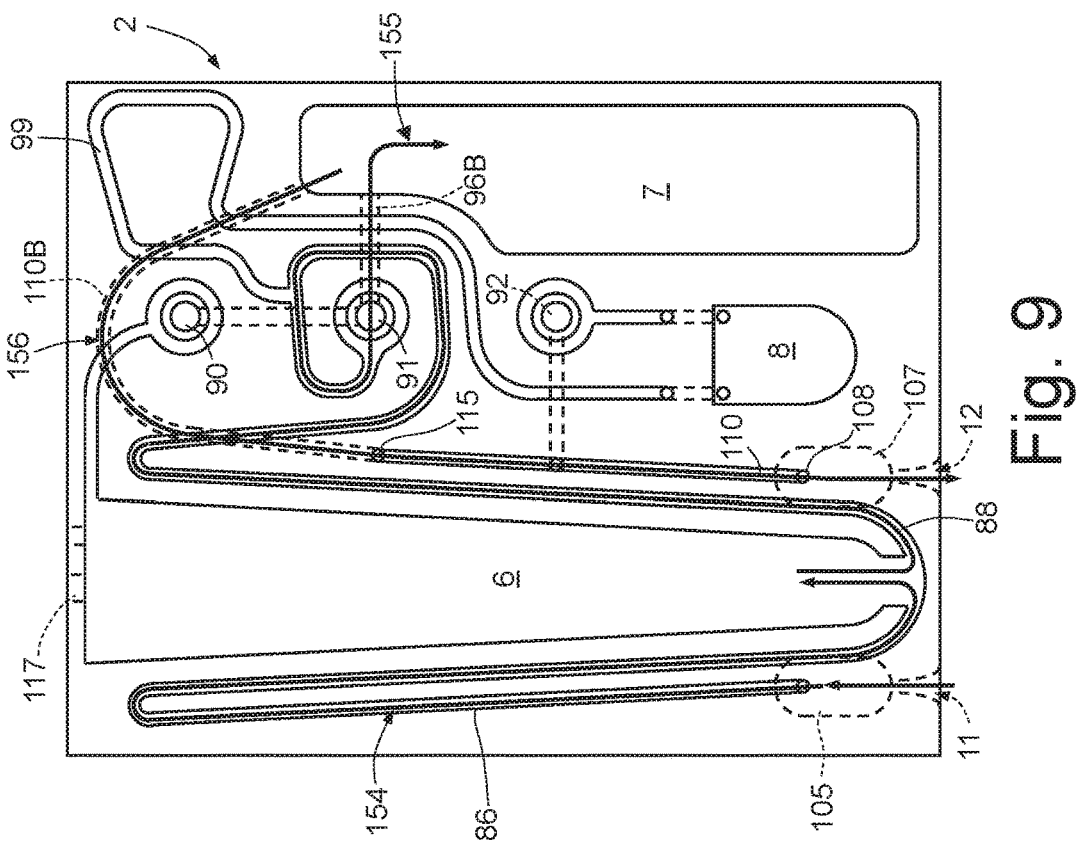

At the end of lysis, spent lysis reagents are discharged into the waste chamber 7 (FIG. 9). To this end, the fluidic inlet 11 is connected to the external environment (by opening the ventilation valve 34 of the control machine 3 and connection to the ventilation inlet 33A of the machine, FIG. 1), thus allowing the air to flow into the cartridge 2 through the inlet fluidic recess 86 towards the bottom end of the extraction chamber 6 (arrow 154). In addition, the magnetic valve actuator 40 opens the second valve 21 by causing deformation of the second shutter 141 and freeing the second valve hole 91. The bottom end of the extraction chamber 6 is thus connected to the waste chamber 7 through the output fluidic recess 88 and the second portion 96B of the first fluidic recess 96 (arrow 155). Also in this step, the pump 25 is active and generates a suction pressure in the waste chamber 7, through the fluidic outlet 12, the second chamber-like recess 107, the second through hole 108, the third vent recess 110, and the fourth through hole 115, as indicated by the arrow 156. In this step, the blocking actuator 43 is activated and attracts the magnetic beads coupled to the nucleic acids. The magnetic beads are generally already in the extraction chamber 6, having been introduced in the manufacturing step, and are here contained in the tablet 98 (FIG. 4), which dissolves when the sample or the first lysis liquid is introduced in a per se known manner. The separated nucleic acids are thus held in the extraction chamber 6 by the magnetic attraction generated by the blocking actuator 43, whereas the spent lysis reagents are drawn into the waste chamber 7 by the action of the suction pressure generated by the pump 25 and the force of gravity. It is noted that, in this step, even though the product recess 99 is free, the spent lysis reagents do not pass through it, since the first stretch thereof is in a higher position than the second portion 96B of the first fluidic recess 96 and as a result of the suction pressure existing in the waste chamber 7. The air displaced in the waste chamber 7 may be discharged outwards through the fluidic outlet 12.

Next, in a known manner, the nucleic acids are flushed by introducing in sequence appropriate flushing liquids supplied by the containers 46 (FIG. 1), according to the path indicated by the arrow 153 of FIG. 8, and subsequently discharging them, along the path indicated by the arrow 156 of FIG. 9, as described previously in detail for the lysis liquid. Also during the flushing step, the anchor actuator 41 may be operated to obtain stirring and mixing of the liquid and the magnetic beads. In addition, the fluidic inlet 11 may be connected to the ventilation inlet 33A of the control machine 3 (FIG. 1) by opening the ventilation valve 34, allowing the air to flow into the cartridge 2 towards the bottom end of the extraction chamber 6 through the inlet fluidic recess 86. As described in detail with reference to FIGS. 48-49, this enables bubbling of air in the extraction chamber 6 and re-mixing of the liquid and of the magnetic beads present therein.

Flushing may comprise a number of cycles with different liquids, in a per se known manner.

At the end of this step, only the nucleic acids attached to the magnetic beads are present on the bottom of the extraction chamber 6.

Next, the nucleic acids, by now purified, are eluted via an expressly provided elution liquid. In this step, the nucleic acids are separated from the magnetic beads and dispersed in the elution liquid. In this step, air may again be bubbled in the extraction chamber 6 to favor detachment, as discussed in greater detail hereinafter with reference to FIGS. 48-49. Moreover, the anchor actuator 41 may again be operated (FIGS. 2, 3A).

Figure 10:
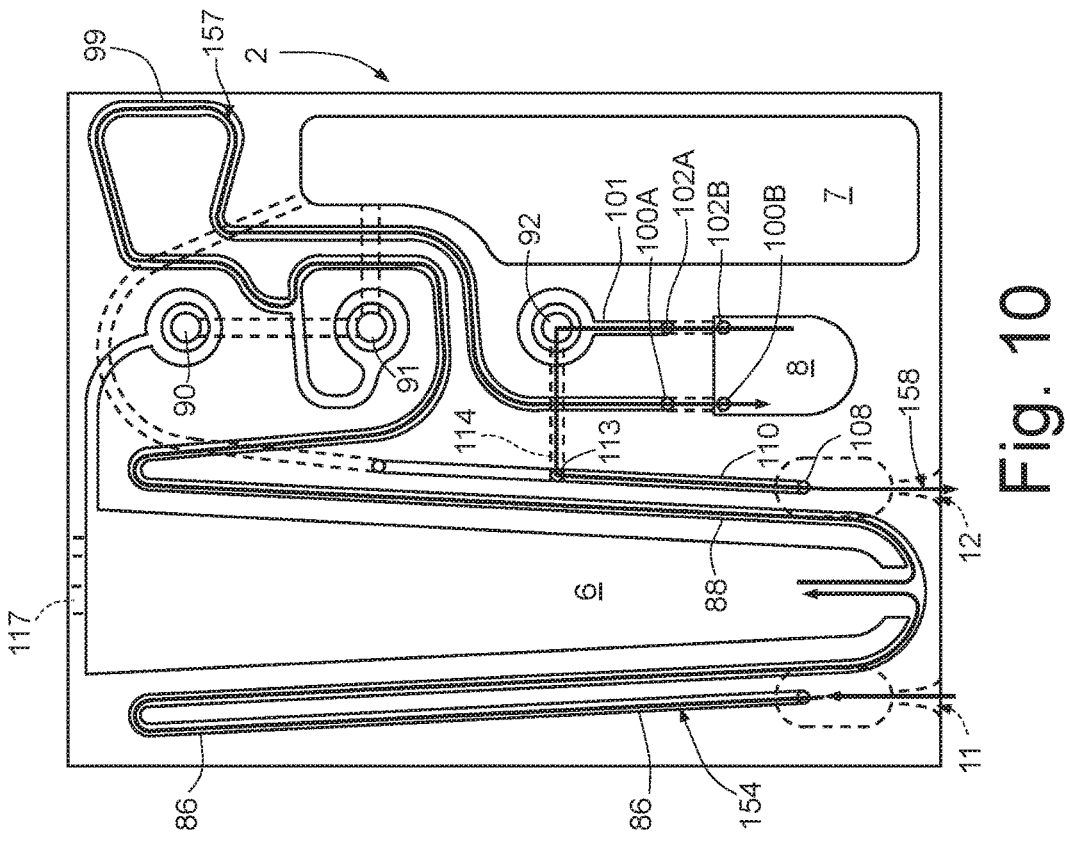

In FIG. 10, the extracted nucleic acids and the elution liquid are sent to the collector or analysis chamber 8 by the action of the suction pressure generated by the pump 25 and the force of gravity. In this step, the first and second valve holes 90, 91 are closed by the corresponding shutters 140, 141 (by closing the first and second valves 20, 21), and the third valve hole 92 is opened by causing deformation of the third shutter 142 (by opening the third valve 22). Thus, the suction pressure generated by the pump 25 causes suction of the liquid on the bottom of the extraction chamber 6 and of the extracted nucleic acids (which are no longer bound to the magnetic beads) through the output fluidic recess 88, the product recess 99, and the first pair of through holes 100A and 100B (arrow 157). In this step, the magnetic beads are withheld in the extraction chamber 6 by the blocking actuator 43 (FIG. 1). It is noted that, in this step, closing of the second valve hole 91 prevents discharge of the extracted nucleic acids into the discharge chamber 7. Since the third valve 22 is open, the suction pressure generated by the pump 25 also causes suction and discharge of the air in the analysis collector/chamber 8 towards the fluidic outlet 12 of the cartridge 2 through the second vent recess 101, the second pair of through holes 102A, 102B, the second valve hole 92, the fourth vent recess 114, the third through hole 113, third vent recess 110, and the second chamber-like recess 107 (arrow 158).

In this step, the fluidic inlet 11 is connected to the external environment and allows the air to flow into the extraction chamber 6 as described above with reference to the arrow 154. Consequently, also in FIG. 10, the flow of air from the outside towards the extraction chamber 6 is indicated by the arrow 154. The air introduced from the fluidic inlet 11 then rises towards the top part of the extraction chamber 6, facilitating displacement of the liquid present on the bottom of the extraction chamber 6 towards the extraction collector/chamber 8.

The nucleic acids are then transferred into the analysis collector/chamber 8, from where they may be recovered or where amplification of the nucleic acids and their analysis may be carried out in a per se known manner.

Figure 11:
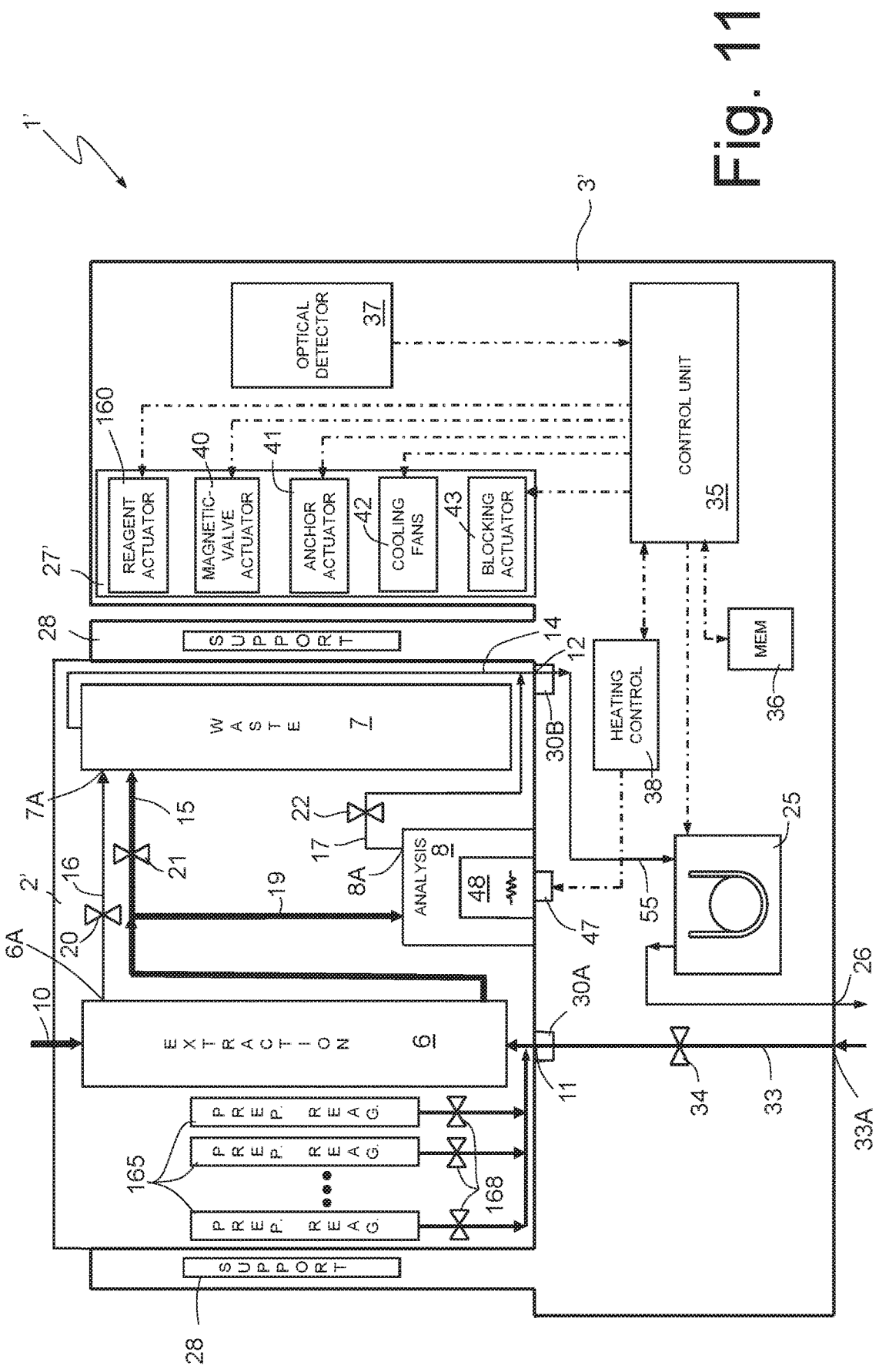
FIG. 11 shows a block diagram of another embodiment of a system for sample preparation and analysis.
Figure 12:
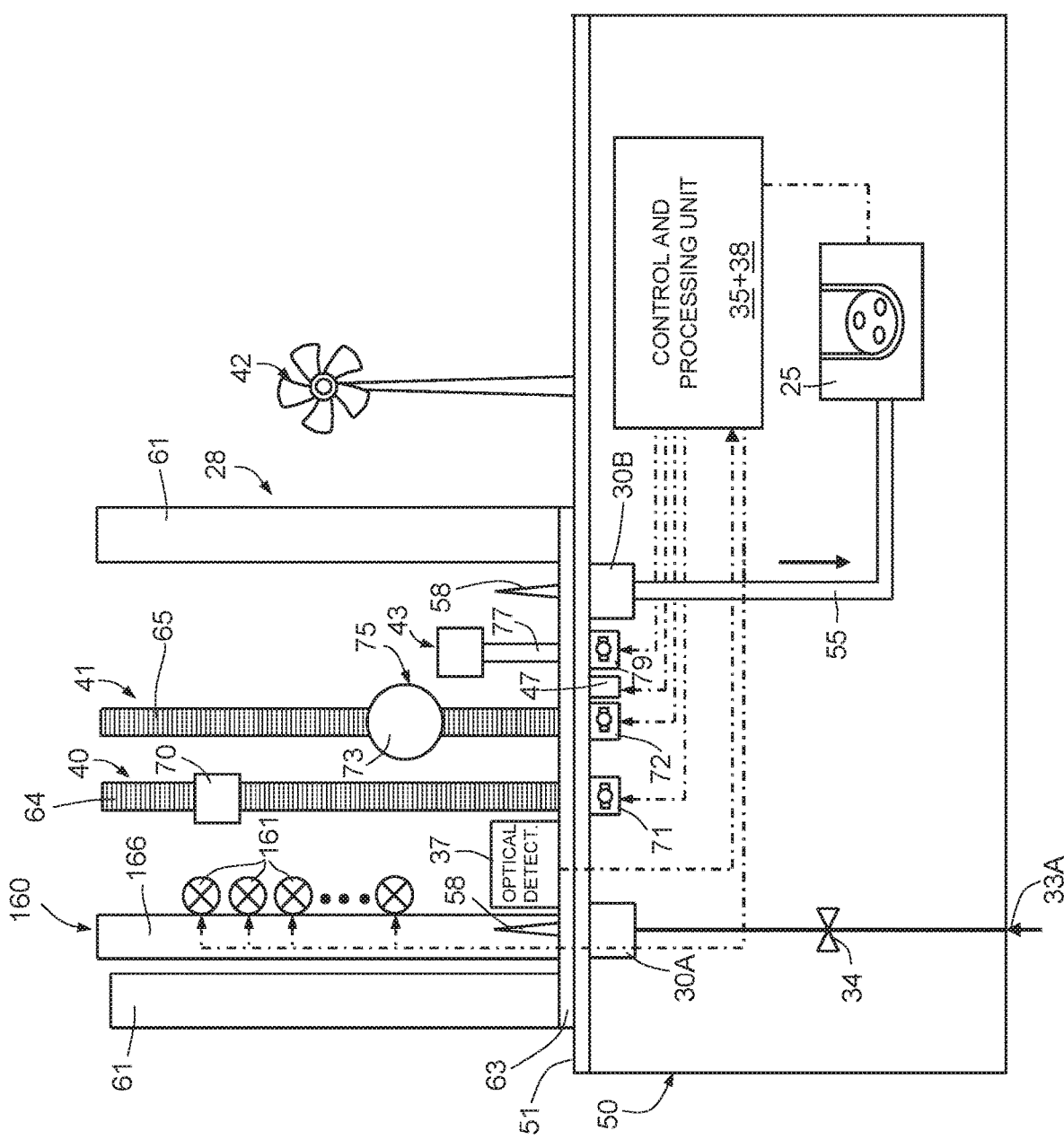
FIG. 12 shows a simplified structural diagram of a control machine belonging to the system of FIG. 11.
Figure 13:
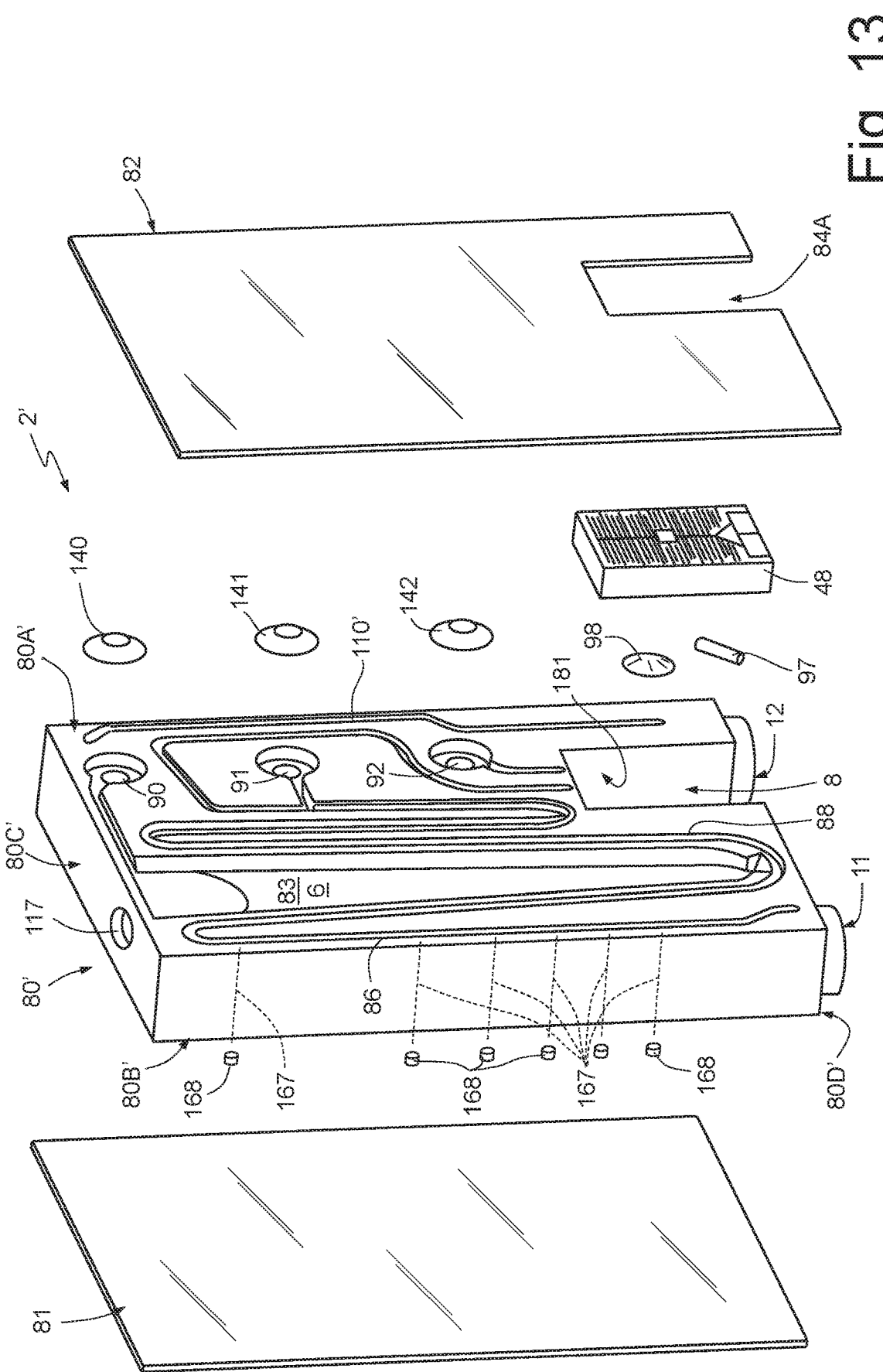
FIGS. 13-15 show, respectively, an exploded view, a front view, and a ghost back view of a second embodiment of a cartridge, which may be used in the system for sample preparation and analysis of FIG. 11.
Figure 14:
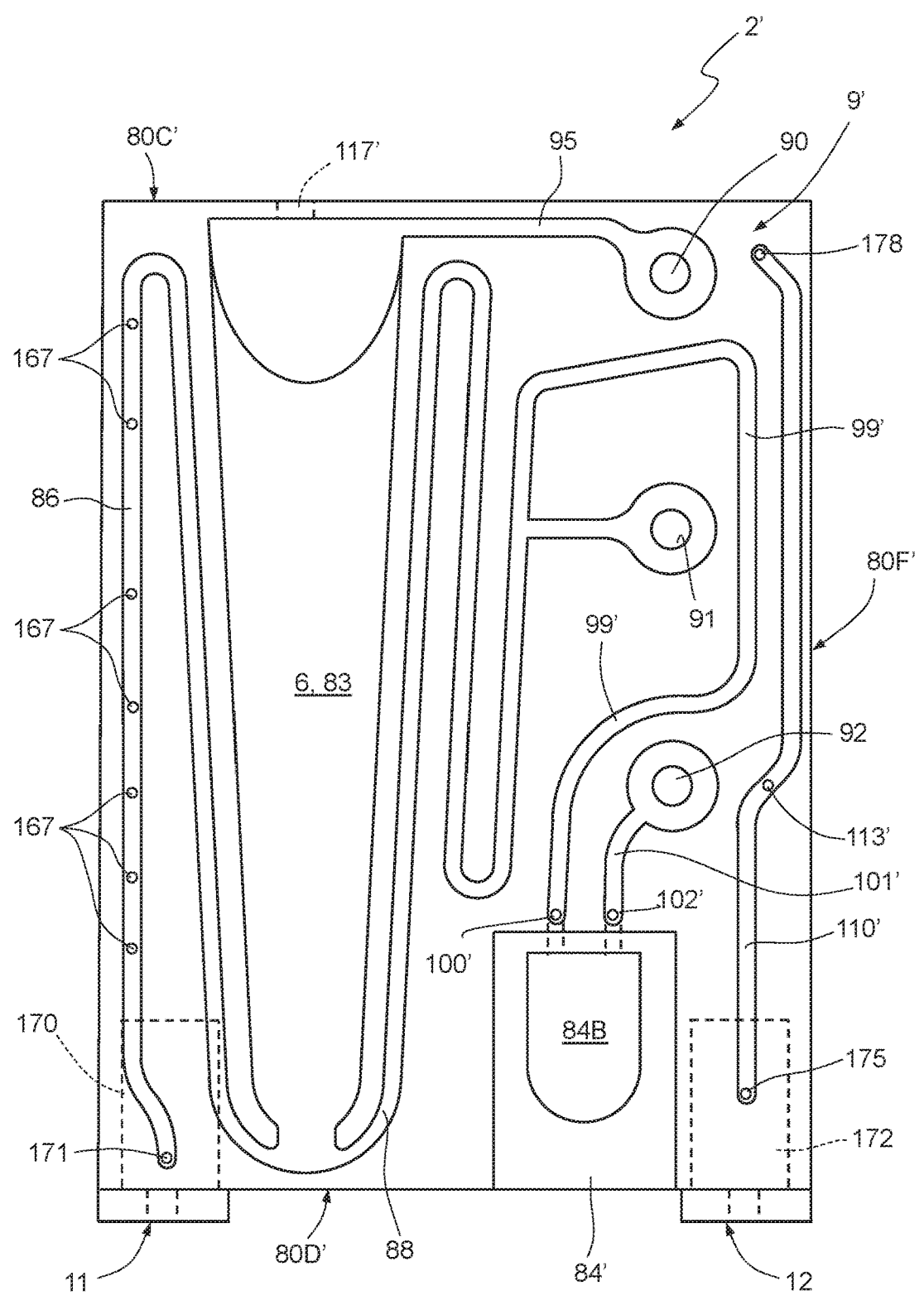
Figure 15:
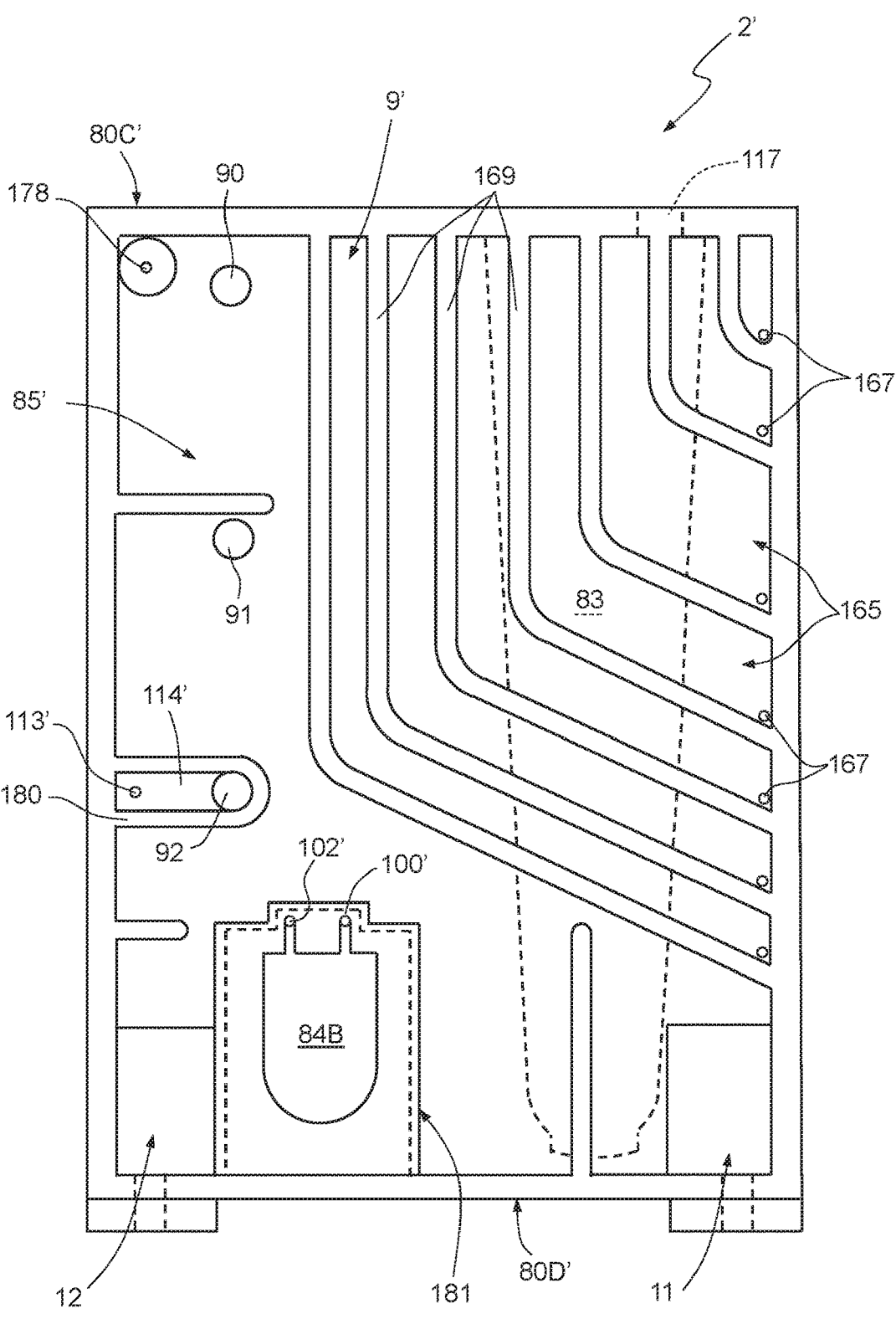
Figures 16, 17A, 17B:
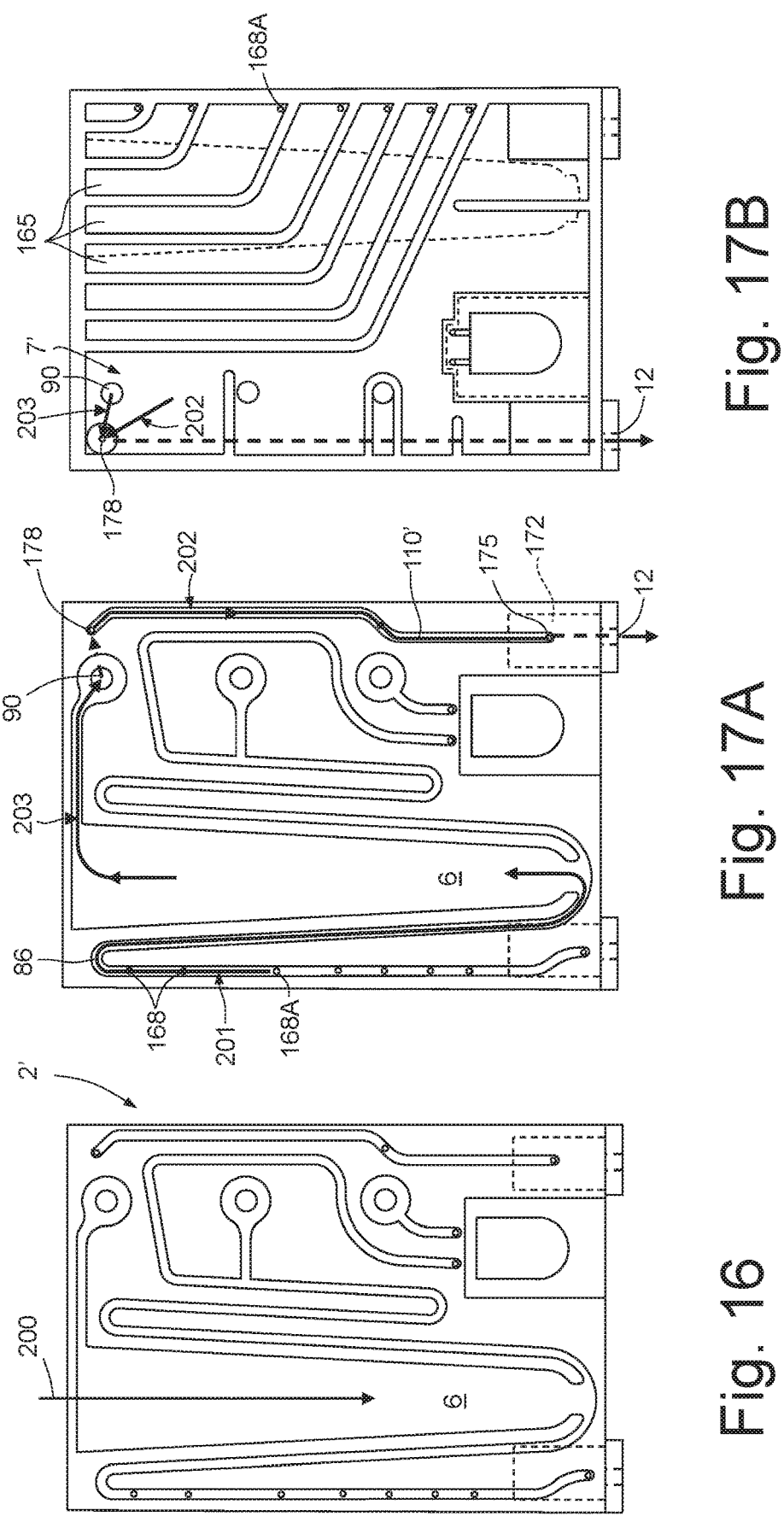
FIGS. 16, 17A, 18A, and 19A show the circulation of fluids on a first face of the cartridge of FIGS. 13-15, in successive operative steps.
FIGS. 17B, 18B, and 19B show the circulation of fluids on a second face of the cartridge of FIGS. 13-15, in successive operative steps.

According to a different embodiment, the cartridge already contains the preparation reagents used in the extraction chamber 6. In this case, the control machine 3 of FIGS. 1-3B is modified as shown in FIGS. 11-12, and the cartridge 2 of FIGS. 4-6 is modified as shown in FIGS. 13-15. Thus, in FIGS. 11-15, elements that are the same as the ones described for the embodiment of FIGS. 1-6 are designated by the same reference numbers and the elements that are modified are distinguished by prime signs.

In detail, FIGS. 11 and 12 show a system 1' comprising a cartridge 2' and a control machine 3'.

The control machine 3' differs from the control machine 3 of FIGS. 1-3B in that the actuator group 27' further comprises a reagent actuator 160 facing the cartridge 2'. The reagent actuator 160 is controlled by the control unit 35'.

Furthermore, the control machine 3' differs from the control machine 3 in that it does not carry any reagent-supporting structure (45 in FIG. 1) and thus does not comprise reagent valves and the corresponding fluidic duct (53 and 54 in FIG. 1). Thus, in the control machine 3' the first connection element 30A is connected only to the ventilation inlet 33A. For the rest, the control machine 3' may be the same as the control machine 3 of FIGS. 1-3.

As mentioned, the cartridge 2' contains the preparation reagents used for extracting the nucleic acids. To this end, the cartridge 2' comprises a plurality of reagent chambers 165 arranged on the second main face 80A' of the body 80' (FIG. 15), connected to the fluidic inlet 11 through respective reagent holes 167 traversing the body 80' and closed by one-shot valves 168 (FIG. 13). The one-shot valves 168 are controlled by the reagent actuator 160. For instance, the one-shot valves 168 may be plugs of wax or any other heat-meltable material, as described in detail hereinafter with reference to FIGS. 20-25. In this case, the reagent actuator 160 may comprise a plurality of melting elements 161 (FIG. 12), for example a plurality of LEDs that, when activated, cause melting of the material of the one-shot valves 168 and opening of the corresponding reagent holes 167. In FIG. 12, the melting elements 161 are arranged on a turret 166 and connected to the control unit 35 controlling turning-on and -off of the melting elements 161.

As an alternative to the above, the reagent actuator 160 on the control machine 3' may comprise just one melting element 161, which can be displaced to a position facing the one-shot valve 168 to be operated each time, using a motor-and-worm mechanism similar to that of the magnetic valve actuator 40.

FIGS. 13-15 show an embodiment of the structure of the cartridge 2' housing the reagent chambers 165. As may be noted, the reagent chambers 165 are arranged on the second main face 80B' of the body 80', approximately behind the extraction chamber 6, are closed at the back by the first closing wall 81', are arranged contiguous to each other, are L-shaped, and are separated from each other by container walls 169. The reagent chambers 165 have respective ends, where the reagent holes 167 open. The reagent holes 167 are thus arranged vertically aligned to the inlet fluidic recess 86 and are closed by the one-shot valves 168 so as to separate the reagent chambers 165 from the inlet fluidic recess 86 when the one-shot valves 168 are closed and to be connected to the inlet fluidic recess 86 when the respective one-shot valves 168 are opened.

In the embodiment of FIGS. 13-15, the fluidic circuit 9' of the cartridge 2' is slightly modified with respect to what described with reference to the cartridge 2 of FIGS. 4-6. In particular, the fluidic circuit 9' is formed by recesses, cavities, and holes, all extending in the body 80' and closed on one side by the first closing wall 81' or the second closing wall 81', 82' according to whether they are arranged on the first main face 80A' or the second main face 80B' of the body 80.

Here (FIG. 14), the fluidic inlet 11 is formed by a first blind hole 170 (represented dashed), which extends from the bottom surface 80D' and is connected to the inlet fluidic recess 86 through an inlet hole 171. The fluidic outlet 12 is here formed by a second blind hole 172 (also represented dashed), which extends from the bottom surface 80D' and is connected to the third vent recess 110' through a first communication hole 175. In turn, the third vent recess 110', similar to the third vent recess 110 of the cartridge 2, extends vertically on the first main face 80A' of the body 80, here in proximity of the second main face 80F', and is connected in an intermediate portion thereof to the third valve hole 92' through the third through hole 113' and the fourth vent recess 114' formed on the second main surface 80B' of the body 80' (FIG. 15). In addition, the third vent recess 110' is connected, near its top end, to a second communication hole 178, which connects the first main face 80A' to the second main face 80B' of the body 80', at the waste chamber 7'.

The waste chamber 7' (FIG. 15) is formed by a waste recess 85' extending over a large part of the second main face 80B' of the body 80', along the area of the reagent chambers 165, and in fluidic communication with the first and second valve holes 90, 91. A first partition wall 180 separates the waste chamber 7' from the fourth vent recess 114' (and thus from the third valve hole 92), and a second partition wall 181 separates the waste chamber 7' from the analysis recess 84' (formed on the first main face 80A', FIG. 14). The analysis recess 84' here has a parallelepipedal shape connected to an analysis opening 84B extending through the body 80'.

Here, the product recess 99' and the second vent recess 101' are formed completely on the first main face 80A' (FIG. 15) and are in fluidic connection with the analysis recess 84' through a fourth communication hole 100' and a fifth communication hole 102', respectively, and the analysis opening 84B (FIGS. 14 and 15).

Operation of the system 1' will be described hereinafter with reference to FIGS. 16-19B.

In detail, the cartridge 2' is inserted in the supporting structure 28 so that the second, covering, wall 82' faces the turrets 64-65 and the analysis chamber 8' (containing the assay reagents) faces the optical detector 37. The contacts 49 on the chip 48 thus each a position facing the electrical-connection element 47 (FIG. 11) on the control machine 3', thus connecting the chip 48 to the control unit 35. Also in this case, during insertion of the cartridge 2', the needles 58 perforate the gaskets (not shown since they are similar to the gaskets 120 of FIG. 4) in the blind holes 170, 172, thus connecting the fluidic inlet 11' and the fluidic outlet 12' to the control machine 3'.

Next (FIG. 16), a liquid sample is introduced into the extraction chamber 6 (arrow 200 of FIG. 16) by using a syringe or by screwing a container (not shown), as described in greater detail hereinafter with reference to FIGS. 31-37. In this step, all the valves 20-22 are closed, and the pump 25 (FIG. 11) is inactive.

Then (FIGS. 17A and 17B), the preparation reagents are introduced into the extraction chamber 6. To this end, the one-shot valves 168 are opened in the sequence provided for by the respective reagent actuators 160 (FIG. 11); for example, they are melted by the respective LEDs 161, as explained in detail with reference to FIGS. 20-25. Opening of each one-shot valve (in FIG. 17A, see the one-shot valve designated by 168A), and thus freeing of the respective hole 167, enables the liquid in the container 165 associated to the one-shot valve 168A to flow towards the inlet fluidic recess 86 and from there into the extraction chamber 6, towards its bottom end (arrow 201). Introduction of the lysis reagents on the bottom of the extraction chamber 6 is thus favored by the force of gravity and by the presence of the suction pressure generated by the pump 25.

In this step, the first valve hole 90 is opened by causing deformation of the first shutter 140, thus connecting the top part of the extraction chamber 6 to the waste chamber 7' (arrow 203). Furthermore, the pump 25 is activated so as to generate a suction pressure in the waste chamber 7' through the fluidic outlet 12, the second blind hole 172, the first communication hole 175, the third vent recess 110', and the second communication hole 178 (arrow 202), also favoring discharge of air from the top part of the extraction chamber 6 (arrow 203).

After introducing the first preparation reagent, namely, the lysis liquid, proper lysis is carried out in a per se known manner.

During lysis, the anchor actuator 41 may be operated to cause a repeated vertical movement and rotation of the anchor 97 (FIG. 4) in the extraction chamber 6 in order to stir and mix the lysis liquid and the magnetic beads capturing the nucleic acids, as described with reference to FIGS. 45-47.

Figure 18B:
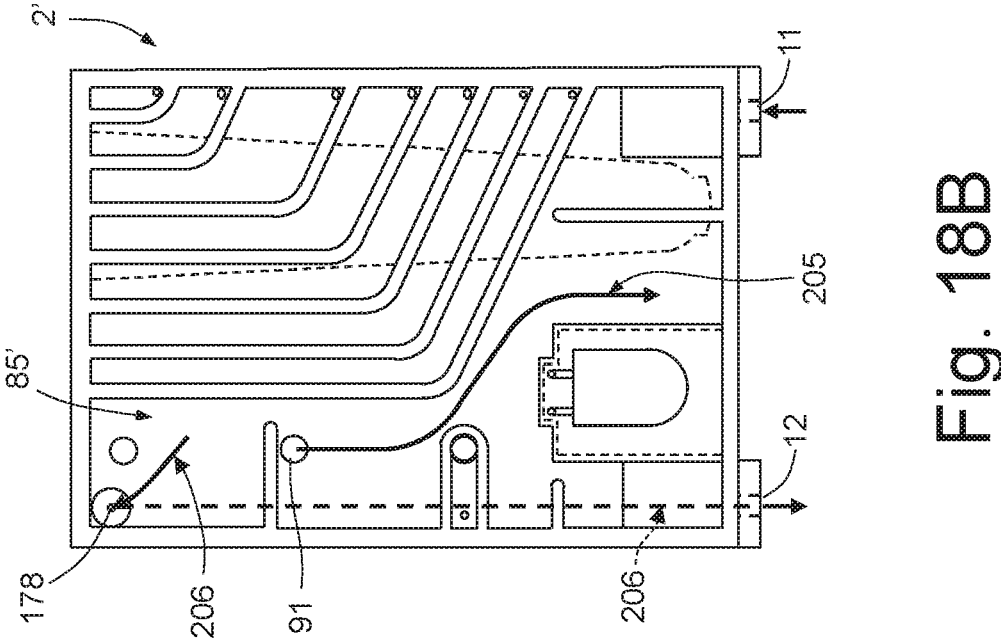
Figure 18A:
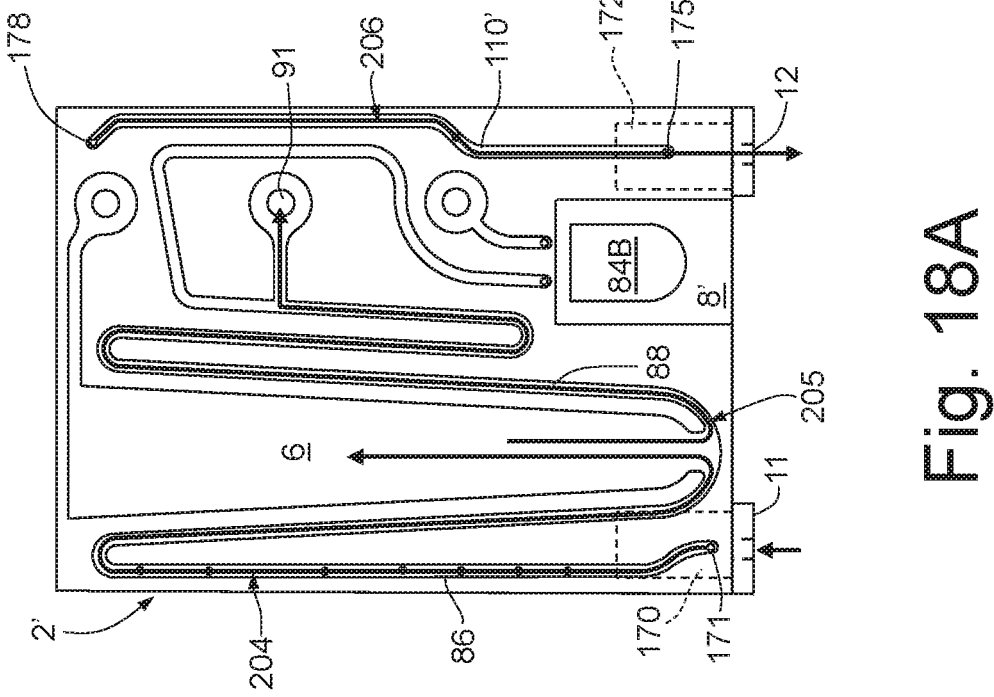

At the end of lysis, the spent lysis reagents are discharged into the waste chamber 7' (FIGS. 18A and 18B). To this end, the fluidic inlet 11 is connected to the external environment (by opening the ventilation valve 34 of the control machine 3' and connection to the ventilation inlet 33A—FIG. 11), allowing air to flow into the cartridge 2' towards the bottom end of the extraction chamber 6 through the first blind hole 170, the inlet hole 171, and the inlet fluidic recess 86 (arrow 204). Furthermore, the magnetic valve actuator 40 (FIG. 11) opens the second valve 21 by causing deformation of the second shutter 141, thus freeing the second valve hole 91. The bottom end of the extraction chamber 6 is thus connected to the waste chamber 7' through the output fluidic recess 88 (arrow 205). Also in this step, the pump 25 is active and generates a suction pressure in the waste chamber 7', through the fluidic outlet 12, the second blind hole 172, the first communication hole 175, the third vent recess 110', and the second communication hole 178, as indicated by arrow 206. In this step, the blocking actuator 43 is activated and attracts the magnetic beads coupled to the nucleic acids. Also in this case, the magnetic beads may already be contained in the extraction chamber 6. The nucleic acids are thus withheld in the extraction chamber 6 by the magnetic attraction generated by the blocking actuator 43, whereas the spent lysis reagents are drawn into the waste chamber 7' by the action of the suction pressure generated by the pump 25 and the force of gravity. The air displaced into the waste chamber 7' may be discharged towards the outside through the fluidic outlet 12.

Then, in a known manner, the nucleic acids are flushed by introducing in sequence appropriate flushing liquids contained in the reagent chambers 165 according to what described with reference to FIGS. 18A and 18B, and by subsequently discharging them, along the path indicated by arrow 205 of FIGS. 18A and 18B, as described previously in detail for the lysis liquid. During flushing, the anchor actuator 41 may be operated for stirring and mixing the liquid and the magnetic beads. Furthermore, the fluidic inlet 11 may be connected to the ventilation inlet 33A of the control machine 3' (FIG. 12) by opening the ventilation valve 34, thus allowing air to flow into the cartridge 2' towards the bottom end of the extraction chamber 6 through the inlet fluidic recess 86, enabling air bubbling in the extraction chamber 6 and remixing of the liquid and of the magnetic beads therein.

Flushing may comprise a number of cycles with different liquids, in a per se known manner.

At the end of this step, only the nucleic acids attached to the magnetic beads step remain on the bottom of the extraction chamber 6.

Next, the nucleic acids are eluted using a suitable elution liquid. In this step, the now purified nucleic acids are separated from the magnetic beads and dispersed in the elution liquid. In this step, air may be bubbled again in the extraction chamber 6 to favor detachment, as discussed in greater detail hereinafter with reference to FIGS. 48-49. Furthermore, the anchor actuator 41 may again be operated.

Figure 19B:
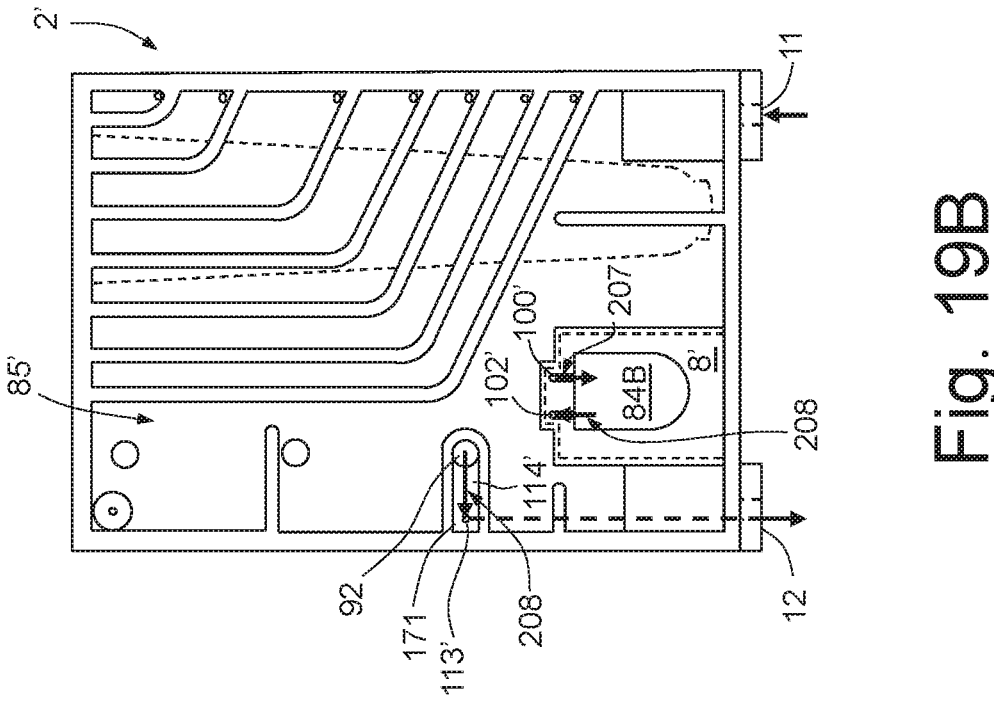
Figure 19A:
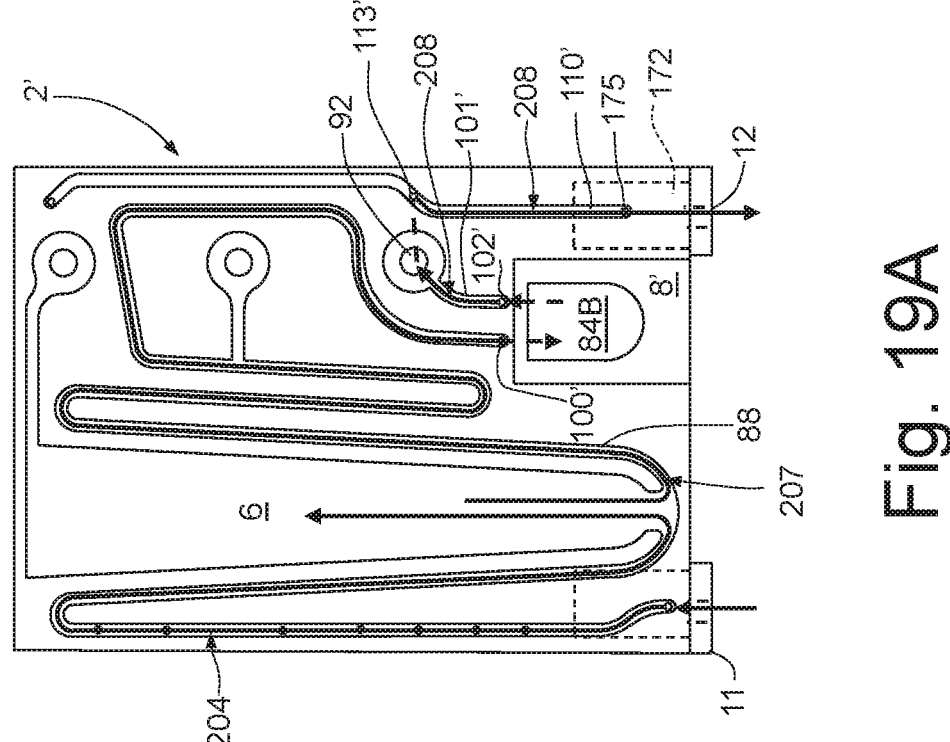

In FIGS. 19A and 19B, the extracted nucleic acids and the elution liquid are sent to the analysis chamber 8' by exploiting the suction pressure generated by the pump 25 and the force of gravity. In this step, the first and second valve holes

90, 91 are closed by the corresponding shutters 140, 141, and the third valve hole 92 is opened by causing deformation of the third shutter 142. The pump 25 is active and the generated suction pressure causes suction of the liquid on the bottom of the extraction chamber 6 and of the extracted nucleic acids (no longer attached to the magnetic beads), through the output fluidic recess 88, the product recess 99', and the fourth communication hole 100' (arrow 207). In this step, the magnetic beads are withheld in the extraction chamber 6 by the blocking actuator 43 (FIG. 12). It is noted that, in this step, closure of the second valve hole 91 prevents discharge of the extracted nucleic acids into the discharge chamber 7'. The suction pressure generated by the pump 25 also causes suction and discharge of the air in the analysis chamber 8' towards the fluidic outlet 12 of the cartridge 2' through the fifth communication hole 102', the second vent recess 101', the third valve hole 92, the fourth vent recess 114', the third through hole 113', the third vent recess 110', and the second blind hole 172 (arrow 208).

In this step, the fluidic inlet 11 is connected to the external environment and allows air to flow into the extraction chamber 6 as described above with reference to the arrow 204. Consequently, in FIGS. 19A and 19B, the flow of air from outside towards the extraction chamber 6 is once again indicated by arrow 204. The air introduced from the fluidic inlet 11 thus rises towards the top of the extraction chamber 6, facilitating displacement of the liquid on the bottom of the extraction chamber 6 towards the analysis chamber 8'.

After transferring the nucleic acids into the analysis chamber 8', the amplification of the nucleic acids and their analysis is carried out in a per se known manner.

As an alternative to what shown and described, instead of having gaskets 120 in the cavities 105, 107 (FIG. 4) or in the blind holes 170, 172 (FIG. 14), the fluidic connection to the connectors 30A, 30B may be similar to the connection of printer cartridges to the printer. In particular, on the cartridge side 2, 2' a self-closing connection element formed by a spring may press a plug on a rubber part functioning as gasket. On the instrument side, just a small cannula may be present, of dimensions compatible with the rubber part, which, during connection, presses the plug, thus compressing the spring.

In the cartridges 2 and 2', the shape and exact arrangement of the fluidic channels, the holes, and the communication openings may vary. For instance, in the cartridge 2 of FIGS. 4-6, they may be formed only in the body 80, and the first closing wall 81 may be simply a smooth plate similar to the cartridge 2' of FIGS. 13-15.

The position of the channels and recesses on the first main face and/or on the second main face 80A, 80B, 80A', 80B' of the body 80, 80' may vary and comprise a number of stretches formed either on the first main face 80A, 80A', or on the second main face 80B, 80B' of the body 80, 80' or on both of the main faces 80A, 80B, 80A', 80B'.

In the cartridge 2' of FIGS. 11-19B, the reagent holes 167 are initially closed and are opened only when the respective containers 165 are connected to the extraction chamber 6, without any need to be closed again subsequently. The same applies to the third valve hole 92 (in both of the embodiments), which is closed until the extracted nucleic acids are transferred into the collector 8, 8'.

The above holes may then be closed using one-shot valves, in an inexpensive and simple way. In particular, according to one aspect of the present description, the one-shot valves are of a material such as to be solid at room temperature and to dissolve when heated, for example using LEDs.

Described hereinafter are possible implementations of one-shot valves that may be used in a fluidic circuit for sample preparation cartridges.

For use in LOC devices, it is desirable for the one-shot valves to be inexpensive but reliable, also over time, hermetically separating two parts of a duct or of a hole. Furthermore, they have be made of materials that are compatible with the samples and the used reagents and should not contaminate the liquids.

FIGS. 20-25 show various embodiments of a one-shot valve 209, which may advantageously be used in a LOC device, for example in the cartridge 2 and 2' of FIGS. 1-19, and has the desired characteristics referred to above. For instance, the one-shot valve 209 may be used as the one-shot valves 168 of the cartridge 2 (shown in FIG. 13) and/or the third valve 22 of both of the cartridges 2 and 2' (FIGS. 5 and 13).

Figure 20A:
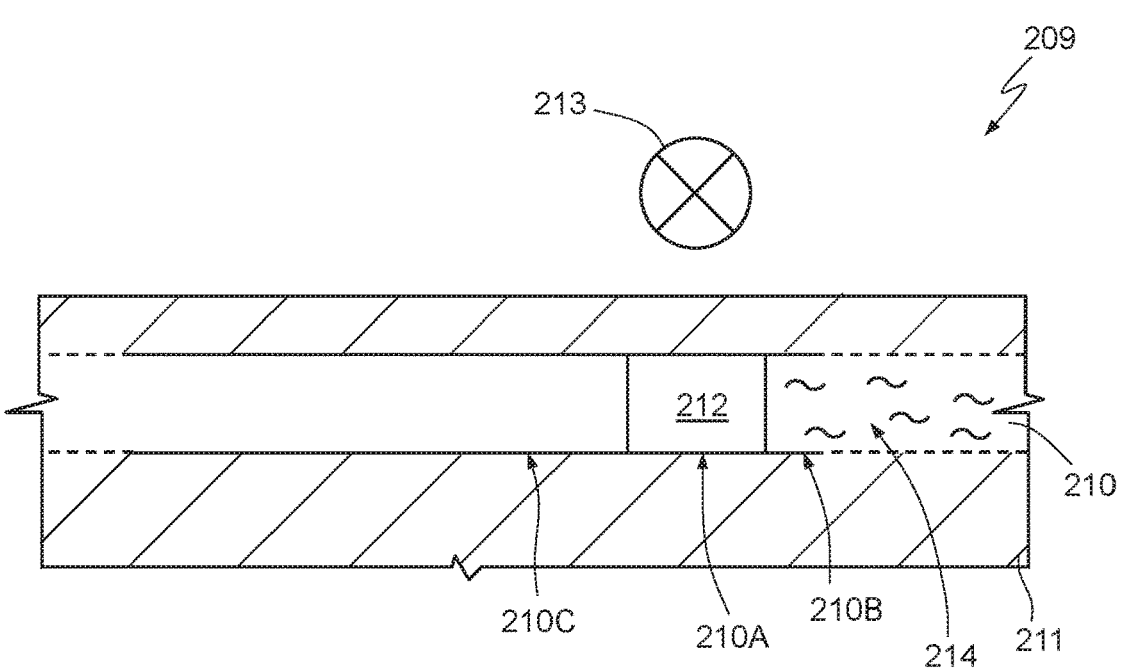
FIGS. 20A and 20B are schematic illustrations of the structure of a microfluidic valve, in the closed condition and in the open condition, respectively, according to one aspect of the present disclosure.
Figure 20B:
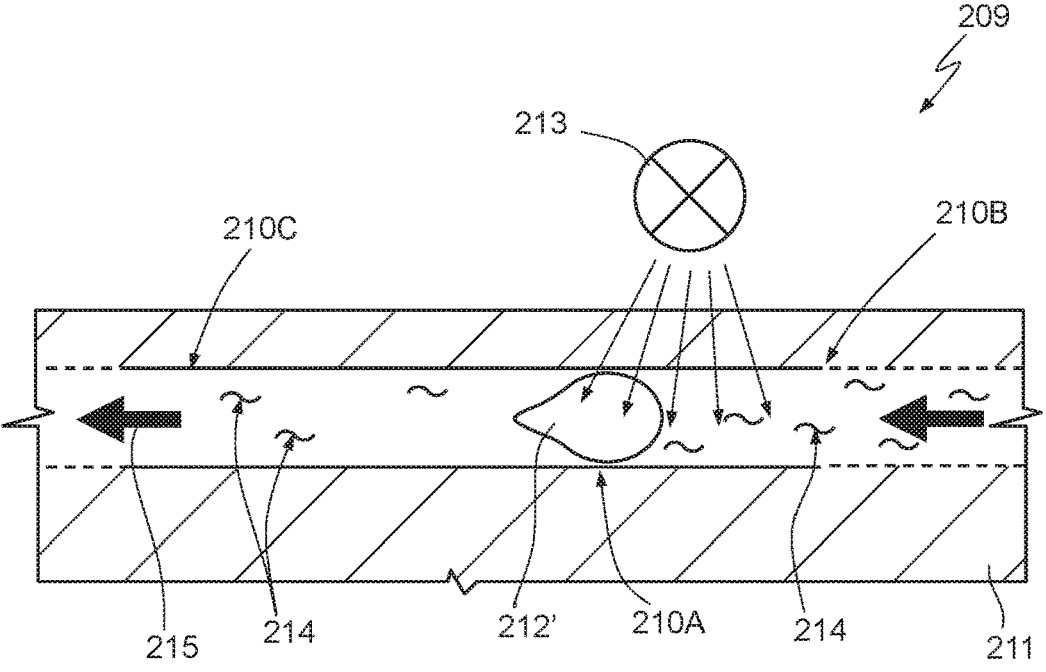

According to FIG. 20A, the one-shot valve 209 comprises a duct 210 in a valve body 211 and an obstruction mass 212.

In particular, the obstruction mass 212 is of wax or other inert material that is solid at room temperature or in any case at the operative temperature, but melts easily and in a controlled way at low temperature. For instance, instead of wax, paraffin or other solid fat may be used, such as cocoa butter, or a gel, such as hydrogel or organogel. Alternatively, the obstruction mass 212 may be formed by a piece of aluminum. In general, the obstruction mass 212 may be of a material that melts at temperatures higher than 60° C. and is inert with respect to the liquids and to the chemical reactions in the valve body 211. The materials referred to above, in particular wax, are suitable to this end, since they are inert with respect to many chemical reactions, such as those envisaged for LOC application, and thus the contact between the obstruction mass 212 and the liquid in the valve body 211 does not cause any contamination.

The obstruction mass 212, in the solid state shown in FIG. 20A, has an outer shape corresponding to that of the duct 210, and dimensions such as to obstruct the latter completely, at a section or lumen 210A thereof (also referred to hereinafter as obstruction section). The obstruction mass 212 thus separates, in the solid state, an upstream portion 210B of the duct 210 from a downstream portion 210C and forms a plug.

It is noted that the obstruction section 210A of the duct 210 may also be a hole extending through a wall and communicating two portions of duct that extend on opposite sides of the wall, as, for example, in the case of the cartridge 2, 2' of FIGS. 1-19.

In use, in order to open the one-shot valve 209, the obstruction mass 212 is heated and melted until it becomes liquid. In this way, it undergoes deformation and at least partially frees the previously obstructed obstruction section 210A (see FIG. 20B, where the obstruction mass is melted and is referred to hereinafter as melted mass 212'). To this end, a radiating source 213, for example a LED or a laser, in particular of an integrated type, is advantageously provided on the inside or on the outside of the valve body 211. When the obstruction mass 212 is of aluminum, the radiating source may be a laser source capable of forming a hole enabling passage of the liquid. Advantageously, the radiating source 213 is focused on the obstruction mass 212 to provide the desired melting energy.

In this way, the obstruction mass 212, which in FIG. 20A obstructs the duct 210, blocking a liquid (designated as a whole by 214) in the upstream portion 210B of the duct 210, in the molten condition (FIG. 20B) frees at least in part the section 210A. The liquid 214 may thus pass into the down- stream portion 210C, according to the arrow 215. To this end, the liquid 214 is subject to a force acting in the direction of arrow 215. For instance, a suction pressure generated by a suction pump (for example, the pump 25 of FIGS. 1, 2, 11, and 12) may be applied to the downstream portion 210C of the duct, or a pressure acting in the direction of the arrow 215 (not shown) may be applied to the upstream portion 210B; alternatively, another force may be used, for example the force of gravity or capillarity, with appropriate arrangement, in use, of the duct 210 in the valve body 211.

Figures 21A, 21B, 22:
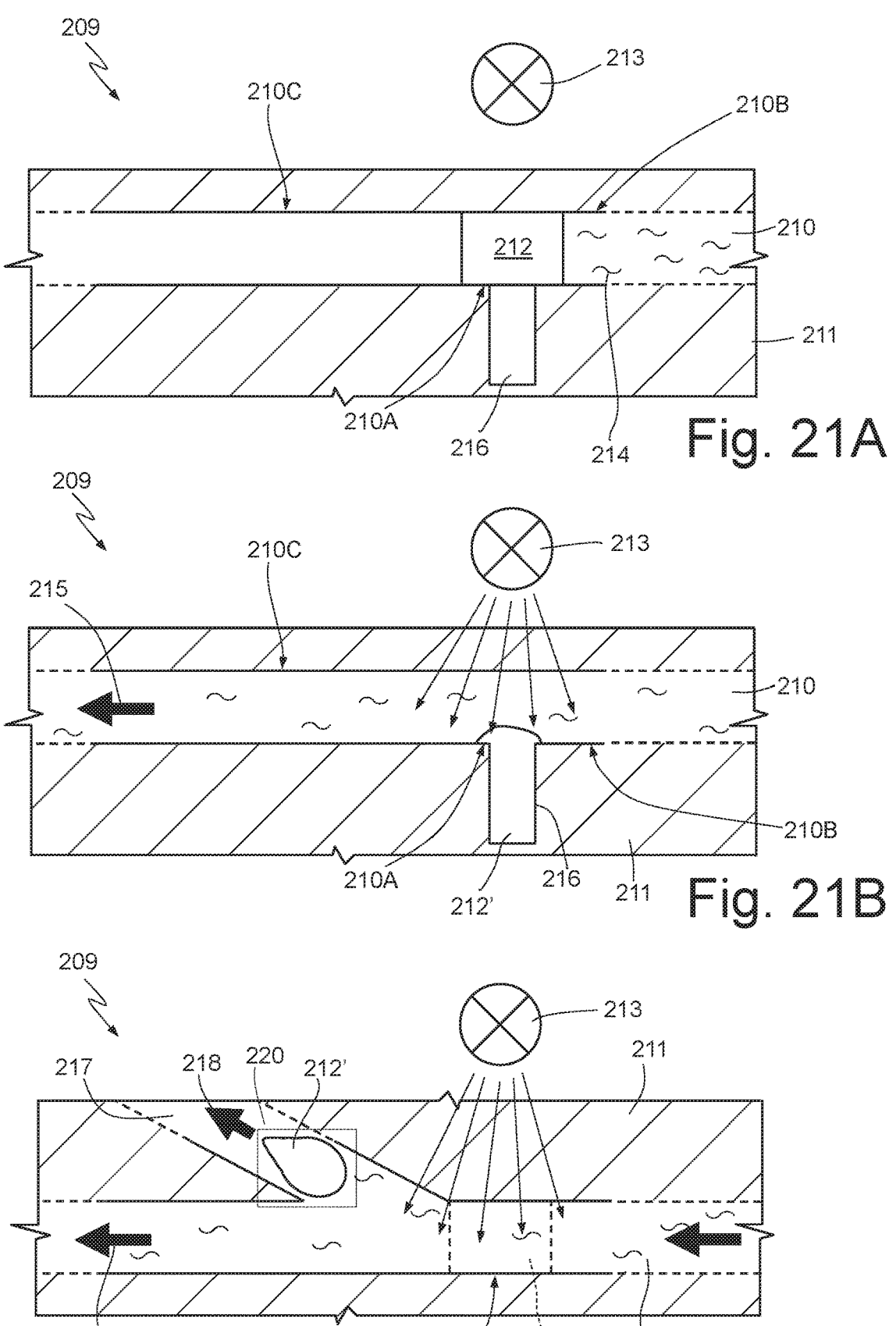
FIGS. 21A and 21B are schematic illustrations of a different embodiment of a microfluidic valve in the closed condition and in the open condition, respectively.
FIG. 22 is a schematic illustration of another embodiment of a microfluidic valve, in the closed condition (dashed line) and in the open condition (solid line)

FIGS. 21A and 21B show an implementation of the one-shot valve 209, wherein, in order to limit the contact between the melted mass 212' and the liquid 214, the duct 210 has a collection recess 216, extending transversely to the duct 210 in the obstruction section 210A. In this case, the obstruction mass 212 (in the non-molten state of FIG. 21A) has dimensions such as, and is arranged so as, to close the inlet area of the collection recess 216. In particular, it has a length, in the longitudinal direction of the duct 210, and a width, in the direction perpendicular to the drawing sheet, larger than the corresponding dimensions of the collection recess 216. The collection recess 216 may be a blind hole, arranged at a lower height (in the use position of the valve body 211) than the obstruction mass 212, or by a peripheral cavity, extending over part or all of the periphery of the obstruction section 210A of the duct 210, including a bottom area.

When, in use, a melting energy is applied to the one-shot valve 209 and the obstruction mass 212 melts and becomes fluid, it may penetrate into the recess 210 by the force of gravity or by capillarity, as shown in FIG. 21B, freeing completely or to a large extent the obstruction section 210A and opening the one-shot valve 209.

In this case, for example by applying, at appropriate instants, the force 215, movement of the liquid 214 may be controlled so as to occur only after the melted mass 212' has completely gathered in the collection recess 216 and has re-solidified, thus reducing to a minimum contact with the liquid 214.

Collection of the melted mass 212' within the collection recess 216 may be favored if the obstruction mass 212 contains magnetically sensitive material, for example a ferromagnetic material, such as iron filings, and by applying a magnetic field from outside. In this case, movement of the melted mass 212' away from the obstruction section 210A may be controlled from outside through a magnetic actuator. For instance, FIG. 22 shows a variant wherein the duct 210 has a discharge branch 217 that branches off from the duct 210, downstream or upstream of the obstruction section 210A, and here extends upwardly (in the use position of the valve body 211). Alternatively, the discharge branch 217 may be arranged, in use, at a lower height than the down- stream section 210C of the duct 210. The discharge branch 217 may be closed, as the collection recess 216 of FIGS. 21A, 21B.

A magnetic actuator 220, external to the one-shot valve 209, shown schematically in FIG. 22, may be activated simultaneously or immediately after application of radiant energy to the obstruction mass 212. As soon as the latter melts and forms the melted mass 212', no longer obstructing the obstruction section 210A, the magnetic actuator 220, which attracts the ferromagnetic beads in the melted mass 212', may be displaced along the discharge branch 217 (arrow 218), causing displacement of the melted mass 212' inside and along the discharge branch 217 as far as the tank (not shown). Instead, the liquid 214 is drawn along the duct 210 as a result of the suction pressure (arrow 215). In this way, thanks also to the force of gravity, separation of the liquid in the duct 210 and of the melted mass 212' is ensured.

Figures 23A, 23B:
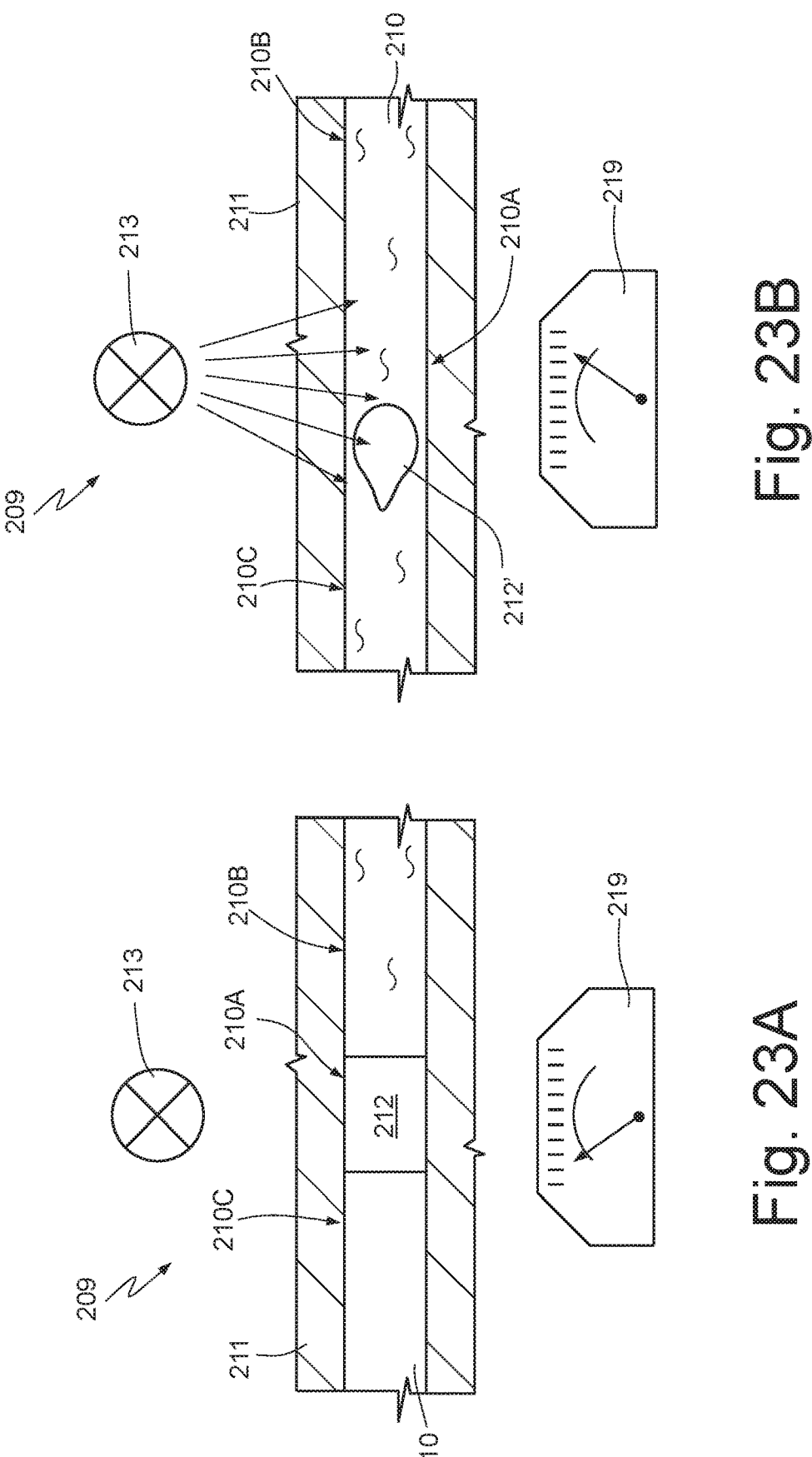
FIGS. 23A and 23B are schematic illustrations of yet another embodiment of a microfluidic valve in the closed condition and in the open condition, respectively.

FIGS. 23A and 23B show an embodiment wherein the valve body 211 is transparent, and a measuring device 219 is arranged along the channel 210 in the obstruction section 210A, on the side opposite to the radiating source 213.

For instance, the measuring device 219 may be a photo-detector element, such as a photodetector transistor or diode, and an associated circuit, which that measures the amount of current flowing in the photodetector element, in a per se known manner.

In this case, when the obstruction mass 212, which is not transparent, is arranged in the obstruction section 210A (FIG. 23A), the measuring device 219 detects only the environmental brightness (in this step, the radiating source 213 is also off). After activation of the radiating source 213, the measuring device 219 measures in any case a low amount of light, since the majority of light emitted by the radiating source 213 is intercepted by the obstruction mass 212, which is opaque. Only after the obstruction mass 212 has melt and the obstruction section 210A is freed, the light emitted by the radiating source 213 can be detected by the measuring device 219, which detects a maximum brightness condition, corresponding to the valve-open condition.

In this way, it is possible to monitor proper operation of the valve 209 both in the closed state (obstruction mass in the obstruction section 210A) and in the open state (melted mass 212' not occupying the obstruction section 210A).

In the embodiment of FIGS. 23A and 23B, the obstruction mass 212 may contain dark colorants that increase light absorption and speed up melting. In this way, both a greater brightness difference between the open and the closed conditions of the valve 209 and a faster actuation are obtained.

Figure 24:
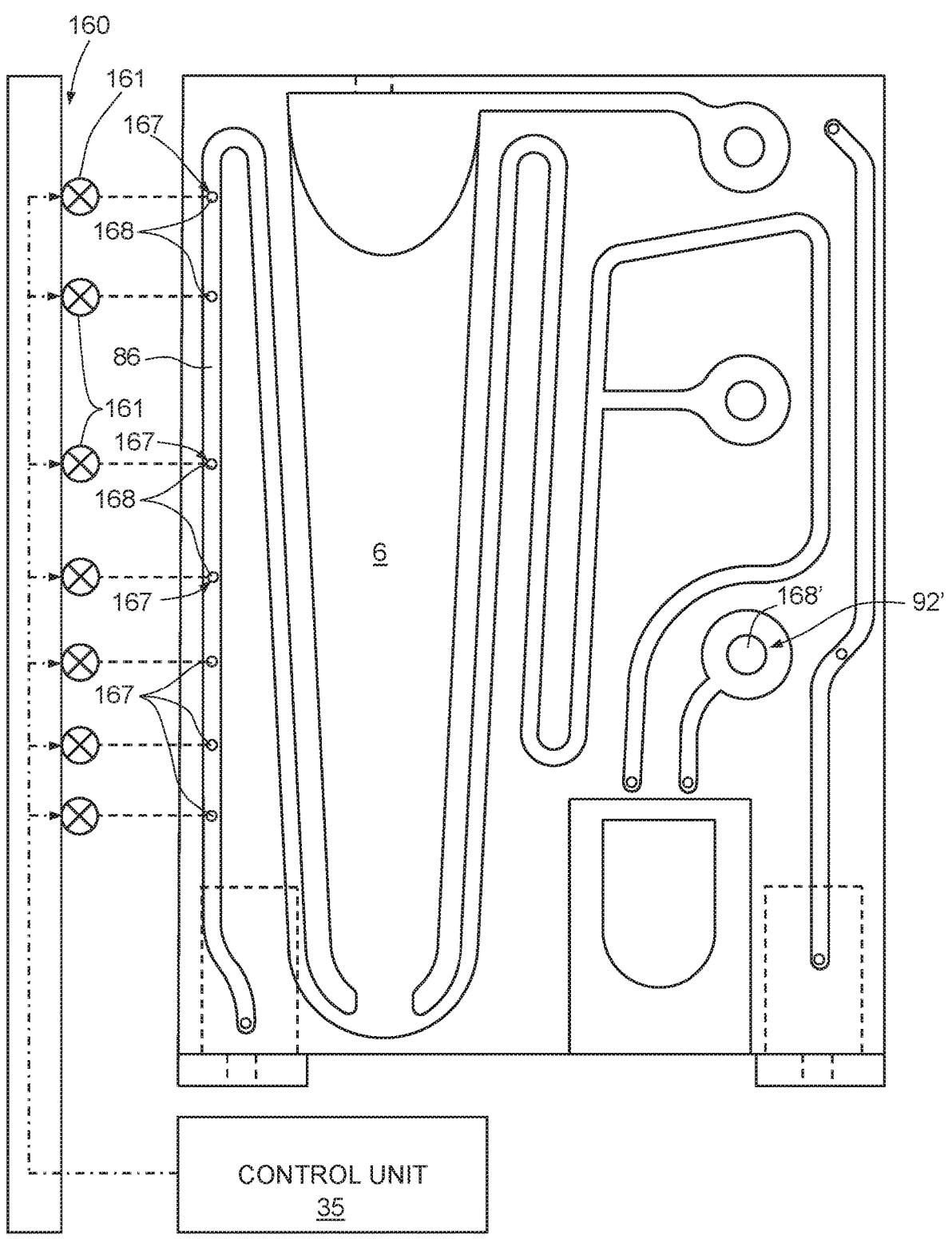
FIGS. 24 and 25 are schematic illustrations of two variants for controlling the microfluidic valves of FIGS. 20-23 in the systems of FIGS. 1 and 11.
Figure 25:
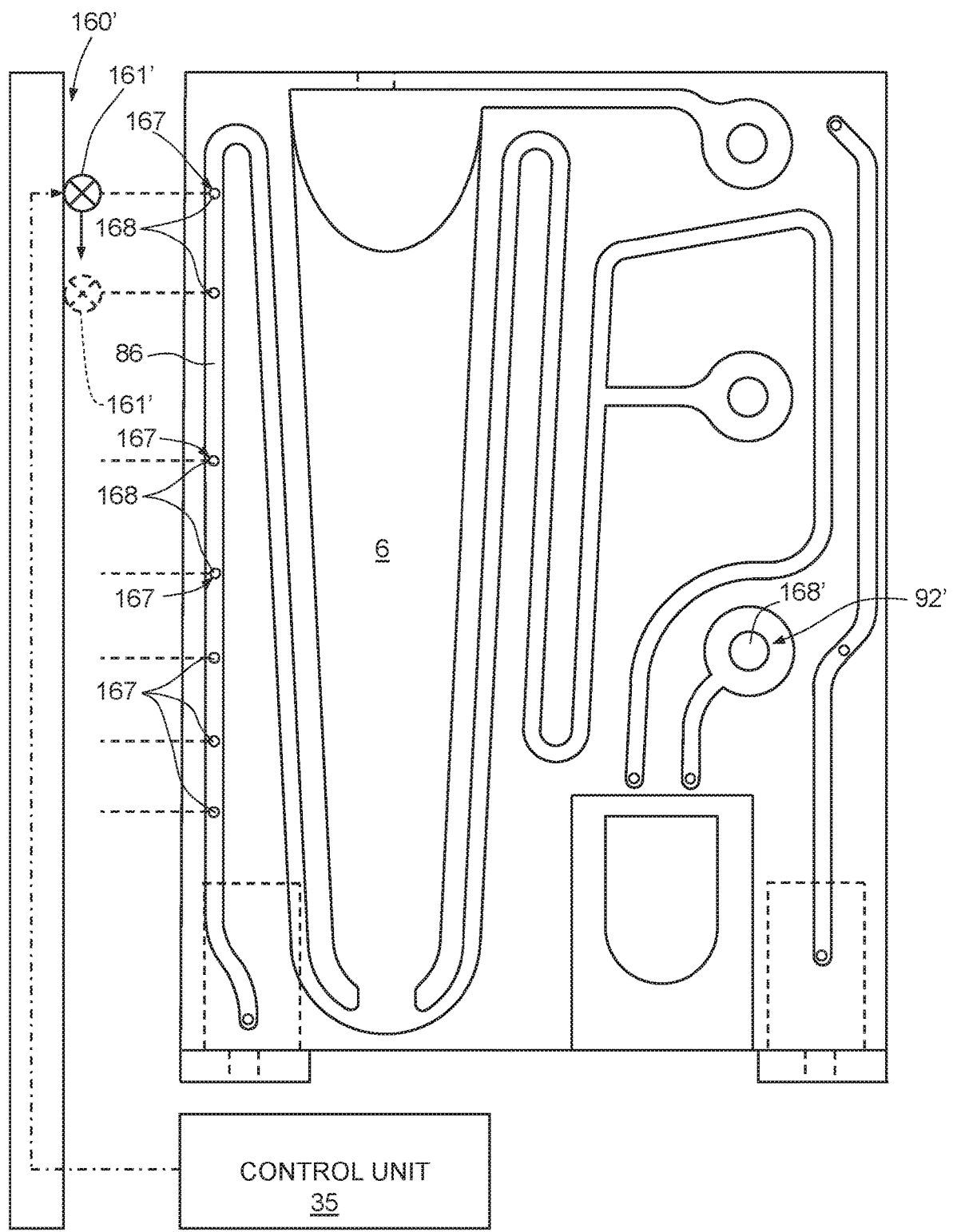

The valve 209 of FIGS. 20-25 may be applied, as has been mentioned, to a cartridge 2, 2' of the type described in FIGS. 1-19. As mentioned, in this case, the valves 209 shown and described with reference to FIGS. 20-25 form the one-shot valves 168 and/or the third valve 22; the valve body 211 is formed by the body 80, 80' of the cartridge 2, 2; the radiating source 213 is formed by the melting elements 161 (FIG. 12); the obstruction section 210A forms the reagent holes 167 or the third valve hole 92; the upstream section 210B is formed by the reagent chambers 165 or by the fourth vent recess 114, 114' (FIGS. 6 and 15, respectively); and the downstream section 210C is formed by the inlet fluidic recess 86 or by the second vent recess 101, 101' (FIGS. 5 and 14, respectively). This solution is shown in FIGS. 24 and 25, which show the arrangement of the melting elements 161, 161' on the turrets 160 and 160', respectively, for a plurality of melting elements 161 (FIG. 24) or a single melting element 161', which is vertically mobile so as to face, each time, the one-shot valve 168 to be actuated (FIG. 25).

Hereinafter possible implementations of microfluidic connectors that may be used in sample analysis cartridges are described.

The sample preparation and analysis cartridges are disposable units and, for their use, are connected to machines that generally contain the re-usable parts of the preparation and analysis system, including actuators and control equipment. Connection between a cartridge and the corresponding machine, enabling exchange of liquids and pneumatic fluids, is obtained through connectors that have the aim of enabling passage of the fluids hermetically with respect to the external environment.

For microfluidic application, it is thus desirable to have a microfluidic connector, usable for connecting a cartridge and a control machine that is simple to use, safe, fluid-tight, and may be manufactured using large-scale and low-cost industrial processes. Frequently, it is desirable for the connector to be able to ensure fluid-tightness of at least one of the two parts, even after detachment.

FIGS. 26-30 show embodiments of a connector group 221 that may advantageously be used in a LOC device, for example in the cartridges 2 and 2' of FIGS. 1-19, and that has the above desired characteristics.

Figure 26:
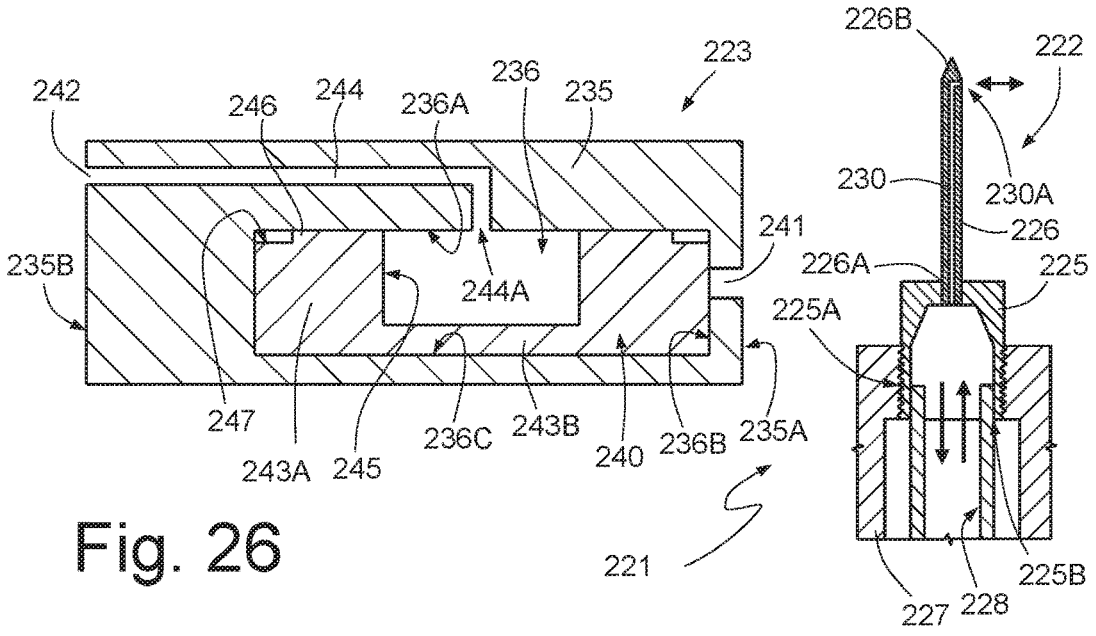
FIG. 26 is a cross-section of a connector group, according to one aspect of the present disclosure.
Figure 27:
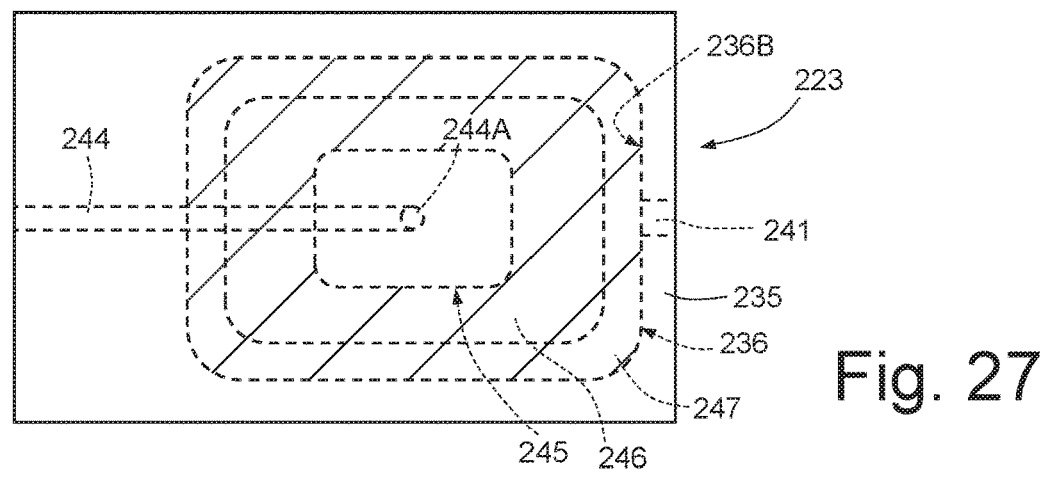
FIG. 27 shows a top plan view, with parts in ghost view, of a part of the connector group of FIG. 26.

In detail, according to FIG. 26, the connector group 221 comprises a male connector 222 and a female connector 223. They may both be either of a disposable or of a non-disposable type, even though generally the female connector 223 is of a disposable type.

In the considered example, the male connector 222 comprises a support 225, for example of plastic or steel, and a needle 226, generally of steel.

The support 225 may have any shape, according to the application. Typically, it is formed by a hollow cup-shaped body, having first mounting means 225A (for example, external screw means), for attaching it to a fixed supporting structure 227, and second mounting means 225B, bonded, for example welded, to a fluidic line 228. For instance, in the case of the machine 3 or 3' of FIGS. 1 and 11, the support 225 may be a cup-shaped plastic body, screwed on the plate 51 of the machine 3, 3' (FIG. 2) and glued or welded to a tubular duct portion that forms or is connected to the ventilation line 33, to the first fluidic duct 54, and/or to the pneumatic duct 55 (which form the fluidic line 228).

The needle 226, which has a generally cylindrical shape, is similar to hypodermic needles and thus has a smooth lateral surface, with very limited roughness so that it is unlikely to trap harmful agents. Furthermore, the needle 226 has a supporting end 226A, bonded, for example welded or glued, to the support 225, and a tip end 226B, which is sharp and pointed. The needle 226 is hollow and has an injection channel 230 longitudinally extending from the supporting end 226A up to a lateral opening 230A. The injection channel 230 thus opens longitudinally with respect to the needle 226 towards the inside of the support 225 and is in fluidic connection, through the support 225, with the fluidic line 228. The lateral opening 230A of the injection channel 230 is arranged alongside the needle 226 near the tip 226A. Thus, the tip 226A of the needle 226 is closed and not perforated.

The fluidic line 228 is generally connected to a fluid actuator (not shown), which can be operated manually or automatically, such as a piston mobile in the support 225 or an external pump that generates a positive or negative pressure within the support 225, or some other actuator.

The female connector 223 comprises a containment body 235 forming a connector chamber 236 housing a gasket 240. The female connector 223 may be of plastic, for example as discussed below with reference to FIG. 28.

In the shown embodiment, the containment body 235 has a generally parallelepipedal outer shape with two opposite lateral faces, designated by 235A and 235B in FIG. 26, which have, respectively, a needle-entry hole 241 and a fluid opening 242, typically not aligned with each other. The outer shape of the containment body 235 and the position of the needle-entry hole 241 and of the fluid opening 242 may, however, vary, according to the application; for example, the containment body 235 may form part of a more complex structure, for instance of the cartridge 2 or 2' of FIGS. 4-6 and 13-15, as discussed hereinafter.

The needle-entry hole 241 extends between the lateral face 235A of the containment body 235 and the connector chamber 236 and is shaped to facilitate introduction of the needle 226. Instead, the fluid opening 242 is connected to the connector chamber 236 with a duct 244, here L-shaped, which opens onto the connector chamber 236 at a duct opening 244A. In particular, the duct opening 244A is formed on a face of the connector chamber 236 (duct face 236A) adjacent to the face—needle face 236B—where the needle-entry hole 241 opens. Thus, the duct face 236A is not opposite to the needle face 236B, for the reasons explained hereinafter.

The gasket 240 is cup-shaped with rectangular base and rounded edges (FIG. 27) and comprises a sidewall 243A and a bottom wall 243B, which delimit a gasket cavity 245. The gasket cavity 245 is faces the duct face 236A of the connector chamber 236 and thus opens towards the duct opening 244A, whereas its bottom wall 243B rests against the face of the connector chamber 236 opposite to the duct face 236A (the bottom face 236C). In some applications, the bottom wall 243B may be missing.

According to an embodiment, the surface of the gasket 240 facing the duct face 236A of the connector chamber 236 has a projecting profile or step 246. The projecting profile 246 surrounds the gasket cavity 245 and bears upon the duct face 236A of the connector chamber 236. The rest of the surface of the gasket 240 facing the duct face 236A of the connector chamber 236 thus forms a peripheral lowered portion 247 surrounding the projecting profile 246. In this way, the gasket 240 does not rest with its entire top surface against the duct face 236A of the connector chamber 236, thereby increasing the pressure exerted by the gasket 240 on the duct face 236A (for a same force), and thus has an excellent tightness even in case of not perfectly flat surfaces of the containment body 235 or of the projecting profile 246 (for example, having a certain degree of roughness).

The material of the gasket 240 is typically rubber, for example silicone rubber, thereby the gasket 240 has a high elasticity, may be easily perforated by the needle 226, has a hardness such as to withstand multiple needle insertion and extraction cycles, has a good seal around the hole where the needle is introduced, and is chemically inert with respect to the substances injected or drawn off. Typically, the material of the gasket 240 has a value on the Shore-A scale comprised between 15 and 45 Shore A, for example 20 Shore A. Other materials suitable for the gasket 240 are, for example, fluorosilicone (with a hardness of between 30 and 80 Shore A) and neoprene (with a hardness of between 20 and 90 Shore A).

The female connector 223 may be manufactured by injection co-molding enabling molding of plastic (to form the containment body 235) and rubber (to form the gasket 240), using various channels for injection into a same mold, or a multiphase injection process, or by any other molding method known in the art, so as to form the gasket 240 directly in the containment body 235.

Figure 28:
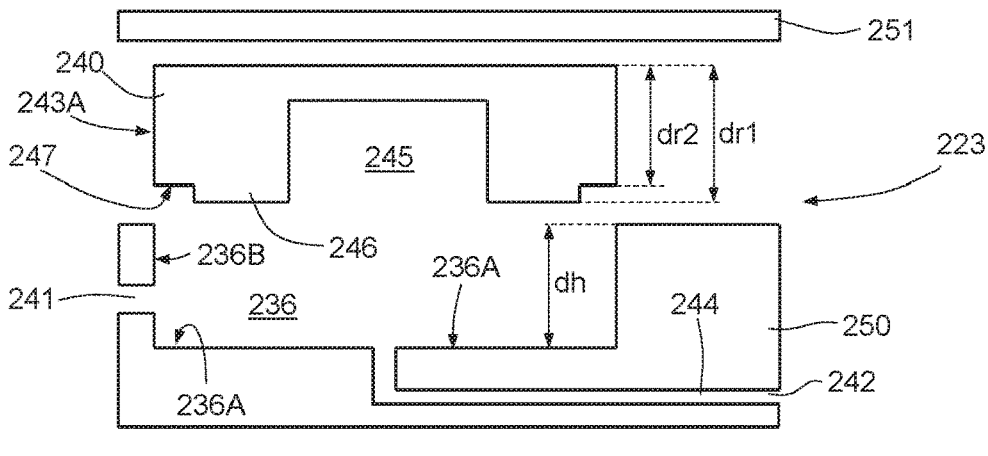
FIG. 28 is a cross-section of an assembling step of the connector group of FIGS. 26-27.

Alternatively, the containment body 235 may be made of two distinct parts, bonded together after insertion of the gasket 240, as shown in FIG. 28. Here, the containment body 235 is formed by a housing portion 250 and a lid 251. The housing portion 250 is, for example, of molded plastic material and houses the connector chamber 236, the duct portion 244 and the needle-entry hole 241. The lid 251 is, for example, formed by a plane plate, also of plastic material. The housing portion 250 and the lid 251 are bonded together using any suitable technique, for example hot rolling or a thermal and/or pressure process.

With the embodiment of FIG. 28, prior to assembling the female connector 223, the projecting profile 246 of the rubber gasket 240 may have a slightly greater height than the connector chamber 236. In particular, as shown in FIG. 28, the connector chamber 236 may have a slightly lower depth dh than the maximum height dr1 of the gasket 240 at the projecting profile 246. In this case, the height dr2 of the gasket 240 at the lowered portion 247 may be slightly lower than the depth dh of the connector chamber 236.

For instance, for a connector chamber 236 having a volume of 120-130 and the gasket cavity 245 having a volume of 10-20 dh may be 2.95 mm, dr1 may be 3 mm, and dr2 may be 2.9 mm.

For the embodiment of FIG. 28, the female connector 223 is assembled by introducing the gasket 240 into the connector chamber 236, with the top surface of the gasket 240 (formed by the projecting profile 246 and the lowered portion 247) against the duct face 236A of the connector chamber 236, and thus with the gasket cavity 245 facing the duct face 236A. In addition, part of the sidewall 243A of the gasket 240 arranges adjacent and contiguous to the needle face 236B of the connector chamber 236 to close the needle-entry hole 241. Then, the lid 251 is bonded to the containment body 235. In this step, the projecting profile 246 of the gasket 240 is slightly compressed, thus ensuring perfect adherence of the gasket 240 to the duct face 236A of the connector chamber 236 and interference seal. The presence of the lowered portion 247 enables possible deformation of the projecting profile 246 and lateral widening thereof, if desired.

In use (FIG. 29), the needle 226 of the male connector 222 is introduced into the needle-entry hole 241, which functions as insertion guide, and perforates the sidewall 243A of the gasket 240 until it penetrates into the gasket cavity 245. Then a fluid, either a liquid or a gas, may be injected by the needle 226 towards the duct portion 244 (as indicated by the arrow 248) or, vice versa, drawn from the fluid opening 242, through the duct portion 244, the gasket cavity 245, and the needle 226, as far as the support 225.

The connector group 221 is thus shaped to ensure a perfect seal during the steps of suction/injection of a fluid. In fact, the overlaying of the materials (harder material for the containment body 235 on the duct face 236A of the connector chamber 236, softer material for the gasket 240, and harder material for the containment body 235 on the bottom of the connector chamber 236) ensures hermetic sealing of the gasket 240 in a lasting way. In particular, the projecting profile 246 causes a mechanical compressive stress in the area (around the duct opening 244A of the duct 244) where hermetic sealing is required, without requiring a perfect adhesion over the entire surface of the gasket 240, which is more difficult to guarantee in a perfect way in each point of the entire surface of the connector chamber 236, in case of intrinsic defectiveness of the material, such as surface roughness.

Furthermore, the arrangement of the needle-entry hole 241 on the needle face 236B, adjacent, and not opposite, to the duct face 236A of the connector chamber 236 (at the duct opening 244A) contributes to tightness of the connector group 221 during injection and suction. It moreover facilitates manufacture of the female connector 223, in the case of production in two pieces since the gasket cavity 245 is simply closed by bonding the lid 251 to the containment body 235 (FIG. 28).

During introduction of the needle 226, thanks to the closed shape of its tip 226B and the transverse arrangement of its lateral opening 230A, the needle 226 does not cause detachment of any portion of the gasket 240 (thus preventing the risk of core drilling) and thus does not create swarf that might enter the needle 226 or penetrate into the fluidic circuit connected to the connector group 221 and block the fluid flow.

With the solution shown in FIGS. 24-27, the female connector 223 is intrinsically sealed since the rubber of the gasket 240 is self-sealing and thus ensures tightness even when the female connector 223 is separated from the male connector 222 (when the needle 226 is extracted). When it is desired to ensure tightness on the male connector 222 after extraction of the needle 226, it is possible to arrange a microfluidic valve of any type upstream of the needle 226, as represented with a dashed line and designated by 254 in FIG. 29.

As referred to above, the connector group 221 may be used in the system 1 and 1' according to FIGS. 1-19. In particular, the connector group 221 may form the connection element 30A and the fluidic inlet 11 or the connection element 30B and the fluidic outlet 12, with the corresponding gaskets 120, of the system 1 or 1' of FIGS. 1 and 11.

Figures 29, 30:
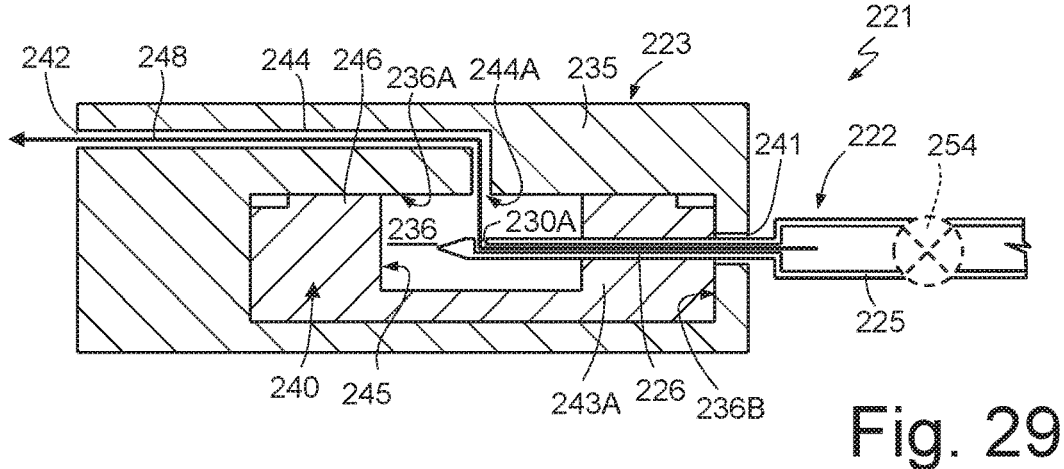
FIG. 29 shows the microfluidic connector group of FIG. 26 in a use condition.
FIG. 30 shows the microfluidic connector group of FIGS. 26-29 applied to the cartridge 2' of FIGS. 13-15.

For instance, FIG. 30 shows the cartridge 2' used in the system of FIG. 11 and shown in detail in FIGS. 13-15. In this case, the containment body 235 is formed by the cartridge 2', the connector chamber 236 is formed by one of the blind holes 170, 172, the gasket 240 forms the gasket 120 of FIG. 13, the duct 244 forms the inlet fluidic recess 86 or the third vent recess 110', and the duct opening 244A of the duct 244 forms the inlet hole 171 or the first communication hole 175. Furthermore, the support 225 may be formed by the plate 51 (FIG. 2), and the needle 226 may form one of the needles 58 of the connection element 30A or 30B. Furthermore, the housing portion 250 (FIG. 28) may be formed by the body 80' of the cartridge 2', and the lid 251 may be formed by the first closing wall 81 (FIG. 13).

Likewise, for the cartridge 2 of FIGS. 4-6, the connector chamber 236 forms the chamber-like recesses 105, 107, the needle-entry hole 241 forms the cavities 104, 106, and the duct opening 244A of the duct 244 forms the through holes 87, 108.

Hereinafter, possible implementations of containers for gathering samples, also defined as test tubes, are described.

Microfluidic devices of a LOC type, to be able to carry out sample analysis, have an inlet for introducing a sample to be treated and analyzed. In these devices, it is desirable that loading is safe and avoids any possibility of cross-contamination, i.e., any type of contamination of the sample by the operator performing the loading and any type of contamination of the operator by the material of the sample. It is moreover desirable that loading is simple and does not require particular skills or attention by the operator to enable execution of a wide range of analyses, without any need for skilled persons.

To this end, it is advantageous to use a container that is easy to attach to the microfluidic device, enables easy introduction of samples, is transportable or portable, prevents any contamination, enables introduction of small amounts of liquids to be analyzed, entailing minimum invasiveness for the patient, and has a low cost.

FIGS. 31-37 show various embodiments of containers 260 that may advantageously be used in a LOC device, for example in the cartridge 2, 2' of FIGS. 1-19, and that have the desired characteristics referred to above. For instance, the container 260 may co-operate with the sample inlet 10 of FIG. 4 or FIG. 9, as explained in detail hereinafter.

According to FIG. 31, the container 260 comprises a tubular body 262 and a lid 263 and is designed to be attached to a container support 261.

The tubular body 262 is typically of plastic, for example polyethylene terephthalate, and is substantially vial-shaped, with a tubular wall 262A, a bottom end 262B having a tapered shape, and an open top end 262C. Here, the terms "bottom" and "top" refer to the use position of the container 260.

The bottom end 262B is closed by a perforable wall 262D, which may be a single piece with the tubular wall 262A and is configured to be easily perforated. In this case, the perforable wall 262D is of the same material as the tubular wall 262A, but thinner. For instance, typical thicknesses of the tubular wall 262A and of the perforable wall 262D are, respectively, 1 mm and from 0.1-0.3 mm. Alternatively, the perforable wall 262D may be of a softer material than the tubular wall 260A, for example rubber.

The tubular body 262 has a blocking structure here formed by a first seal ring 264 slid on the tubular wall 262A. The first seal ring 264 is of elastomeric material, for example Viton, and may co-operate with a corresponding stop 265 on the container support 261, as explained below. In this case, the blocking structure 264 also functions as a sealing structure and prevents, in the event of leakage during or after perforation of the perforable wall 262D, part of the analyzed sample from possibly escaping into the external environment.

Alternatively, the blocking structure may be made in any other way, for example as peripheral projection that hooks onto a corresponding attachment portion on the container support 261 or that snaps into a cavity or behind a projection on the container support 261.

Moreover, the tubular body 262 has a guide structure 266, for proper insertion of the container 260 into the container support 261. Here, the guide structure 266 of the container 260 is formed by a peripheral ribbing (which, for reasons of simplicity, is again designated by 266) that projects from the tubular wall 262A near the bottom end 262B, and thus lower down (in the use position) than the first seal ring 264. The peripheral ribbing 266 may be just one and extend over all or over a major part of the circumference of the tubular wall 262A, or be formed by a plurality of portions (at least two) arranged radially at a distance from each other.

The peripheral ribbing 266 has a certain elasticity to be able to undergo deformation and overcome the stop 265 on the container support 261 (as explained below). The ribbing may have a triangular or trapezoidal cross-section, with a bottom surface 266A (closer to the bottom end 262B) with oblique orientation in order to facilitate introduction thereof into the container support 261, and a top surface 266B (facing the top end 262C of the tubular wall 262) that is substantially perpendicular to the tubular wall 262 in order to block the tubular body 262 vertically in the container support 261 after insertion, as explained in greater detail hereinafter. Alternatively, the peripheral ribbing 266 may be relatively stiff, and the stop 265 may be more elastic. According to another possibility still, both the peripheral ribbing 266 and the stop 265 may be elastic.

The tubular body 262 further has lid attachment means 263, here formed by a thread 269 external to the tubular wall 262A and arranged near the top end 262C. The top end 262C of the tubular body 262 also has a lid-guide structure 270, here formed by a guide tooth, which extends in the tubular wall 262A. The guide tooth 270 may be just one and have a circumferential extension, or be formed by a number of parts, as is clear to the person skilled in the art.

The lid 263, which is typically of plastic material, for example the same plastic material as the tubular body 262 (polyethylene terephthalate), comprises a base portion 263A, a screwing portion 263B, and a plug portion 263C. In detail, the base portion 263A has a flat cylindrical shape and is typically designed to close the top end 262C of the tubular body 262, the screwing portion 263B has the shape of a cylindrical wall projecting peripherally from the base portion 263A, and the plug portion 263C extends centrally from the base portion 263A on the same side as the screwing portion 263B. The screwing portion 263B internally has a structure for fixing to the tubular body, here a counter-thread 271, designed, in use, to be screwed on the thread 269 of the tubular body 262. Thus, the screwing portion 263 has an internal diameter slightly greater than the external diameter of the tubular wall 262A and, in the closed condition of the container 260, extends outside the tubular wall 262A. The plug portion 263C has a cylindrical shape, here full, with a slightly smaller diameter than an internal diameter of the tubular wall 262A so as enable it to be fitted in the top end 263C of the tubular body 262 when the lid 263 is screwed thereon.

In addition, the plug portion 263C has a greater height (in the longitudinal direction of the tubular body 262) than the screwing portion 263B, for the reasons explained below. Furthermore, the plug portion 263 carries a second seal ring 272 slid on the plug portion 263 that has an external diameter substantially equal to or slightly greater than the internal diameter of the tubular wall 262A so as to seal hermetically the inside of the tubular body 262.

The container support 261 is designed to receive the bottom end 263B of the tubular body 262 and fluidically connect the inside of the container 260 to a fluidic circuit, as shown in FIGS. 32A and 32B.

The container support 260 is here formed by a cylindrical wall 275 with a circular base extending from a connection portion 277 fixed to, for example integral to, a LOC device, such as the cartridge 2 or 2' of FIGS. 4-6 and 13-15, at the sample inlet 10, and has a container-introduction end 275A. The container support 261 may be a single piece with the connection portion 277 or may be manufactured separately and bonded, for example glued or fluidically connected by any type of stable sealed connection. Near the connection portion 277, the container support 261 has an own guide structure 276 intended to couple with the guide structure of the container 260. In the considered example, the guide structure 276 of the container support 261 is formed by an internal thread (which, for reasons of simplicity, is once again designated by 276), intended to engage the peripheral ribbing 266 of the container 260. Furthermore, near its container-introduction end 275A, the cylindrical wall 275 of the container support 260 has the stop 265 referred to above that is designed to co-operate with the first seal ring 264, for blocking the container 260 in use (FIGS. 32A and 32B). The stop 265 may comprise, for example, an internal peripheral projection, formed near the container-introduction end 275A of the cylindrical wall 275. The stop 265 advantageously has an inclined top surface 265A to facilitate passage of the peripheral ribbing 266 of the tubular body 262 and of the first seal ring 264 during introduction of the container 260, and a bottom surface 265B, perpendicular to the cylindrical wall 275, to prevent exit of the first seal ring 264 after it has overcome the stop 265. In this step, as mentioned, the peripheral ribbing 266 of the tubular body 262 and the first seal ring 264 undergo elastic deformation, to overcome the stop 265.

As an alternative to what shown, the guide structure 276 of the container support 261 may be arranged near the container-introduction end 275A, and the stop 265 may be arranged between the guide structure 276 of the container support 261 and the connection portion 277.

The connection portion 277 has, at the center of the container support 261, a perforation structure 278 projecting towards the inside of the cylindrical wall 275 of the container support 261. The perforation structure 278 is hollow, has a pointed shape, and is in fluidic connection with a fluid-communication line 279 formed in the connection portion 277.

In use, prior to bonding the container 260 to the container support 261, the tubular body 262 is filled with a sample to be analyzed. Filling may be carried out in different ways: for example using an external pipette or as described below with reference to FIGS. 33-35. When it is filled using a pipette (not shown), after filling, the lid 263 is screwed on the tubular body 262. In this case, since, during screwing, the plug portion 263C fits and extends into the tubular wall 262A, it causes an overpressure within the container 260, which facilitates subsequent transfer of liquid. In this step, the second seal ring 272 seals the sample in the container 260 (FIG. 32A) from the external environment.

Then, the container 260 is inserted and screwed into the container support 261, here through the engagement of the peripheral ribbing 266 of the tubular body 262 with the internal thread 276 of the container support 261. Screwing ensures a correct guide and exact positioning of the container 260, and in particular of the perforable wall 262D, which, during screwing, is thus easily perforated by the perforation structure 278 (FIG. 23B). At the end of insertion of the container 260, the first seal ring 264 blocks the container 260 in position inside the container support 261, preventing extraction thereof, and ensures that the sample does not spill out, as explained above.

The liquid in the container 260 may thus flow into the fluid-communication line 279, as indicated by arrow 280, thanks to the overpressure generated by the plug portion 263C, as explained above, and possibly aided by gravity.

Figure 33:
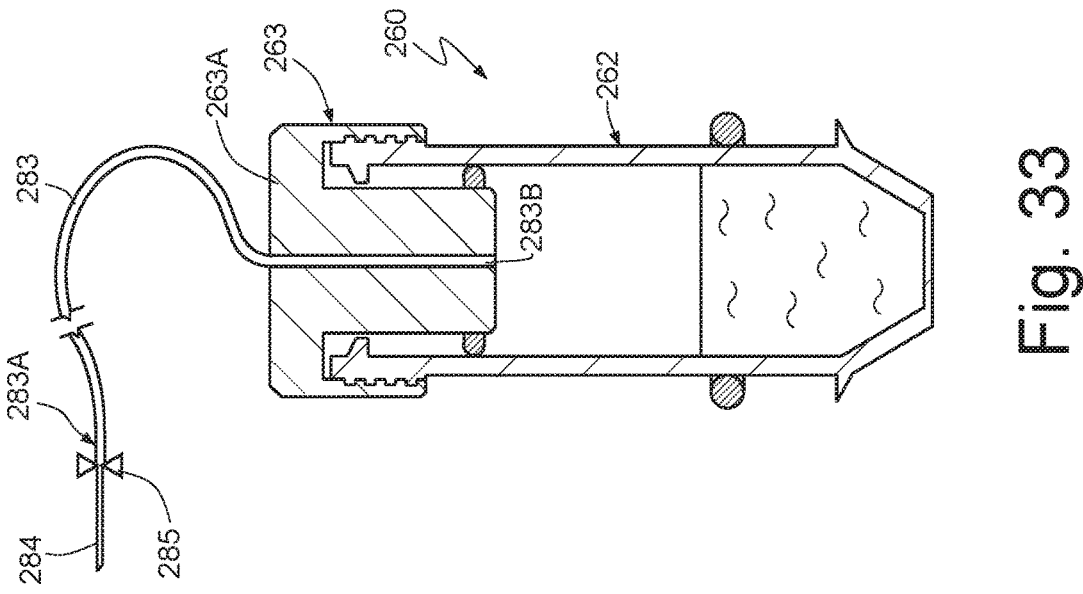

FIG. 33 shows a container 260 enabling a different method for loading the sample, which may advantageously be used for sampling blood from a patient. Here, the lid 263 is connected to a catheter 283, or other cannula or tube. In particular, the catheter 283 has a first end 283A connected, for example, to a sampling needle 284, possibly through a valve needle 285 (for example, of a type common for blood sampling), and a second end 283B extending through the base portion 263A and the plug portion 263C of the lid 263 and in fluidic connection with the inside of the container 260.

In this way, once the sampling needle 284 has been positioned in a blood vessel of a patient and the valve needle 285 has been opened, the difference in pressure between the inside of the container 260 and the blood vessel draws in the blood. Next, after closing the valve needle 285, the container 260 is fitted into the container support 261, perforating the perforable wall 262D and enabling the blood to flow in the fluid-communication line 279, as has been described above with reference to FIGS. 32A and 32B. Alternatively, the container 260 may be inserted into the container support 261 prior to sampling.

With the solution of FIG. 33, it is advantageous that the container 260 does not require opening of the lid 263 to load the sample, to the advantage of sterility of the system.

Figure 34:
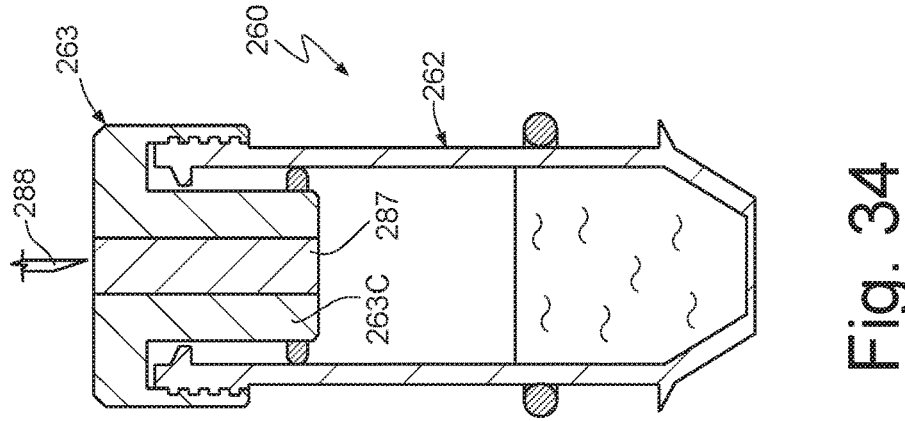

FIG. 34 shows another way for loading the container 260. Here, the lid 263 is not monolithic, but the plug portion 263C has a core 287 of a perforable and re-closable material, such as rubber, in particular silicone rubber. The core 287 extends throughout the height of the plug portion 263B and through the base portion 263A.

The core 287 can thus be easily perforated by a filling needle 288 for injecting the sample into the container 260. Then, the filling needle 288 is extracted. However, the elastic material of the core 287 ensures reclosing of the injection hole, keeping the inside of the container 260 sealed from the external environment.

Figure 35:
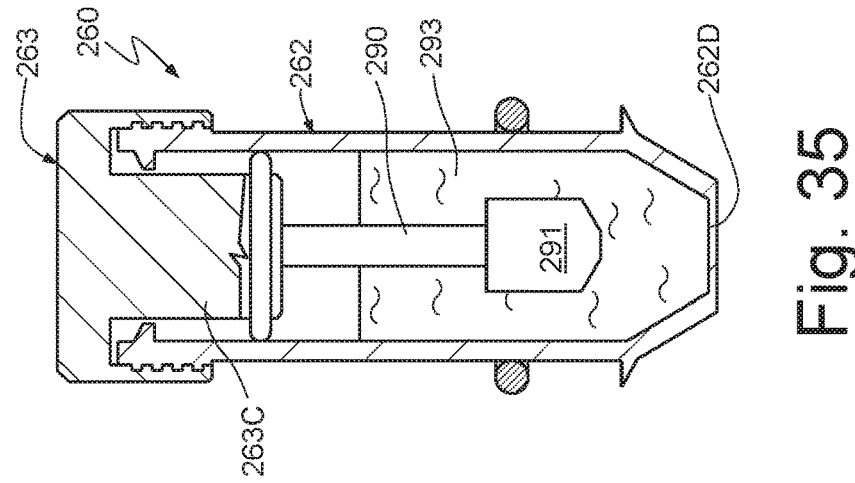
FIGS. 33-35 show various embodiments of the container of FIG. 31.

The container 260 of FIG. 35 enables sampling and transferring a sample also of a solid type. Here, the plug portion 263C of the lid 263 carries a rod 290 ending with a swab 291 of a type commonly used for sampling solid material. Moreover, an elution liquid 293 is present within the container 260.

In this case, after sampling the solid material with the swab 291, the lid 263 is screwed on the tubular body 262, causing immersion of the taken solid sample in the elution liquid 293. The solid material, thus dissolved in the elution liquid 293, may be transported by the elution liquid 293 to the fluid-communication line 279 (FIG. 32) after perforation of the perforable wall 262D.

Figures 36, 37:
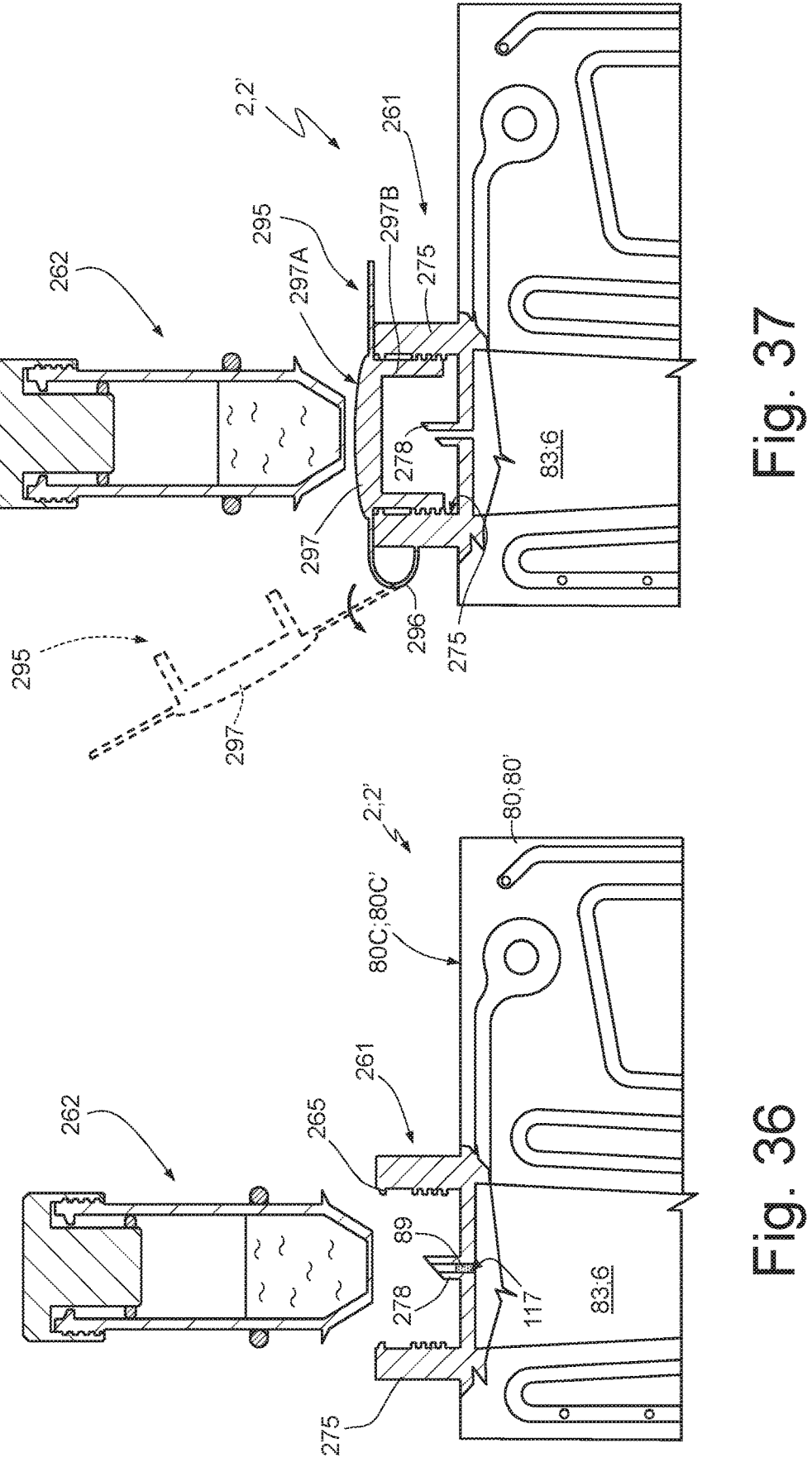
FIG. 36 shows the container of FIG. 31 applied to the cartridge 2 or 2' of FIG. 5-7 or 13-15.
FIG. 37 shows the container of FIG. 31 applied to a variant of the cartridge 2 or 2' of FIG. 5-7 or 13-15.

FIG. 36 shows the container 260 of FIG. 31 applied to the cartridge 2 or 2' of FIG. 5-7 or 13-15. Here, the cylindrical wall 275 of the container support 261 projects from the top face 80C, 80C' of the body 80, 80', as the perforation structure 278. In addition, the cylindrical wall 275 and the perforation structure 278 are one piece with the body 80, 80'. Here, the inside of the perforation structure 278 is directly connected to the extraction recess 83 through the introduction opening 117, closed by the plug element 89. In a not shown manner, the cylindrical wall 275 of the container support 261 may be equipped with the guide structure 276 of the container support 261, as for the container 260 of FIG. 31.

In the embodiment of FIG. 37, the container support 261 has a support plug 295, of an incorporated type, shown with a solid line in a closed position and with a dashed line in the open position. The support plug 295, which may be of the type used in test tubes, is here one piece with the cylindrical wall 275 of the container support 261. Alternatively, the support plug 295 may be slid on or otherwise coupled to the cylindrical wall 275 of the container support 261. The support plug 295 comprises a stem 296, which extends from the cylindrical wall 275, and a cap 297. The stem 296 is flexible and forms a hinge that enables opening and closing of the incorporated plug by simply flipping over the cap 297, as shown in FIG. 37 with a solid line (closed position) and with a dashed line (open position). The cap 297 has a closing portion 297A, which, in the closed position of the incorporated plug 295, extends transversely to the cylindrical wall 275 of the container support 261, closing the container-introduction end 275A of the latter, and an engagement portion 297B, projecting from the closing portion 297A and with a cylindrical shape, designed to be inserted into the cylindrical wall 275 of the container support 261 and to engage with interference fit the cylindrical wall 275 of the container support 261, for example at the stop 265 or internal thread 276 of the cylindrical part 275, by exploiting the elasticity of the material. To this end, the engagement portion 297B of the cap 297 has an external diameter equal to or slightly greater than, an internal diameter of the cylindrical wall 275 at the stop 265 or than the internal thread 276, to be blocked by one of these, in a closed position of the support plug 295.

The incorporated plug 295 may thus be easily manually opened while inserting the container 260.

In the case of application to the cartridge 2 or 2', since the container 260 has no air inlet to compensate for the outlet of liquid, the pump 25 (FIGS. 1 and 11) is sized so as to enable emptying of the container 260. Alternatively, the pump 25 may carry out a sequence of suction and insufflation steps to facilitate transfer of all the liquid from the container 260 to the inside of the chamber 6 (inside the extraction recess 83).

According to another embodiment, air compensation exploits the lateral opening 118 of the cartridge 2 (FIGS. 5-7). The same process may be applied for the cartridge 2' (FIGS. 13-15).

Advantageously, the container 260 is readily usable, has reduced costs, is robust, and ensures the desired sterility level. The container support 261 may be easily provided on a connection portion 277, such as a microfluidic cartridge.

Possible implementations of magnetically controlled valves are described hereinafter.

Microfluidic devices comprise fluidic paths integrated in the device and formed by channels, openings, holes, etc., which are opened and closed according to the treatment steps. To this end, microvalves may generally be used that can be controlled from outside.

It is thus desirable for these valves to be simple, inexpensive, and reliable, ensure the possibility of being easily integrated in the microfluidic device, and be compatible with the liquids treated.

FIGS. 38-42 show various embodiments of a magnetic valve 300 that may advantageously be used in a LOC device, for example in the cartridges 2 and 2' of FIGS. 1-19 and has the desired characteristics referred to above. For instance, the magnetic valve 300 may form the valves 20-22 shown in FIGS. 1-19.

In detail (FIG. 38A), the magnetic valve 300 comprises a valve body 301 and a shutter 302 and co-operates with an actuator 303. The magnetic valve 300 and the actuator 303 form a valve group 304.

The valve body 301 forms a fluidic path 305, here comprising a first path portion 306 and a second path portion 307. The path portions 306, 307 are here arranged transversally, for example perpendicular, with respect to each other. In particular, here, the second path portion 307 ends at the first path portion 306 at an opening 307A, to form a T-coupling 309. Here, the first path portion 306 is a duct, has rectangular or square section and defines a wall 306A facing the second path portion 307. The second path portion 307 may be a duct or a hole leading to another duct, and have a section of any shape, for example circular, rectangular, or square.

The wall of the valve body 301 forms, around the opening 307A, a peripheral projection 308 that extends towards the inside of the first path portion 306.

The shutter 302 is formed by a magnetically deformable membrane arranged inside the first path portion 306 at the coupling 309. The shutter 302 is thus arranged in front of the opening 307A of the second path portion 307 and is configured to close the opening 307A when the shutter 302 is in the undeformed condition and to free at least one part of the opening 307A when the shutter is in the deformed condition.

In detail, the shutter 302 is here formed as a single piece of elastically deformable ferromagnetic material, typically of soft bicomponent rubber incorporating ferrite particles or powder, iron filings, and, in general, powder of materials that are susceptible to a magnetic field. For instance, in case of ferrite, it may be 66% of the total weight.

Figure 38A:
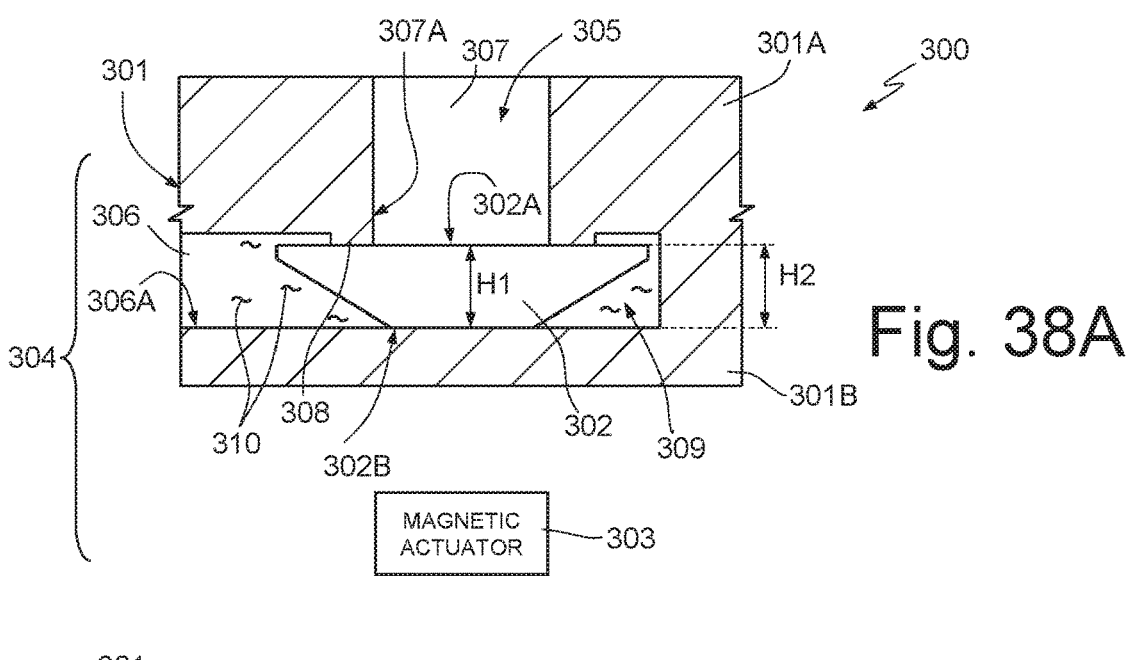
FIGS. 38A and 38B show cross-sections of a valve group comprising a magnetic valve that may be controllably opened and closed, according to one aspect of the present disclosure, in the closed condition and in the open condition, respectively.
Figure 39A:
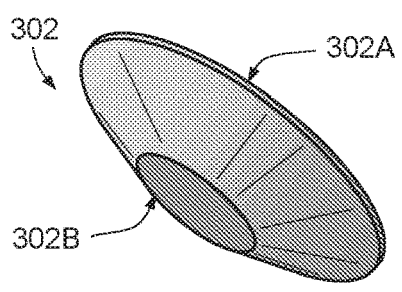
FIGS. 39A and 39B are perspective views from above and from below, respectively, of a part of the magnetic valve of FIG. 38A, in the undeformed condition.
Figure 39B:
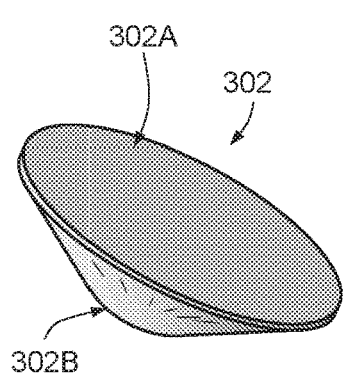

In the embodiment of FIGS. 38A, 39A, and 39B, in the undeformed condition, the shutter 302 is substantially frustoconical with a major base 302A and a minor base 302B;

moreover, a cylindrical portion of small height forms the major base 302A. The shutter 302 is moreover arranged with the major base 302A against, and in contact with, the peripheral projection 308 and with the minor base 302B against, and in contact with, the wall 306A of the first path portion 306. The major base 302A of the shutter 302 has a greater diameter than the opening 307A, if the latter has a circular shape. In any case, the major base 302A of the shutter 302 has a greater area than the opening 307A, and a shape and position such as to cover and completely close the opening 307A.

Furthermore, the height H1 of the shutter 302 (height of the frustoconical portion) is equal to, or slightly greater than, the height H2 of the first path portion 306 (or the dimension of the first path portion 306 in the considered section, in a perpendicular direction to the wall 306A of the first path portion 306). In this way, thanks to the elasticity of the shutter 302, in the undeformed condition, the shutter 302 is slightly pressed within the fluidic path 305 and reliably closes the opening 307A. The fluidic connection between the first and second path portions 306, 307 is consequently interrupted, and a fluid, for example a liquid, 310 in the first or in the second path portion 306, 307 (in FIG. 38A, in the first path portion 306) can thus not flow into the other path portion 307, 306.

Advantageously, in the embodiment of FIGS. 38-39, where the first path portion 306 is located upstream and the second path portion 307 is located downstream of the fluidic path 305, the fluid 310 pushes against the conical wall of the shutter 302, and the pressure of the fluid 310 favors adhesion of the shutter 302 against the opening 307A. The adhesion effect is increased when an external force is applied on the fluid 310 in the fluidic path 305 in order to push the fluid 310 towards the second path portion 307 or draw it into the second path portion 307.

The actuator 303 is of a magnetic type and generates a magnetic field B, when activated. For instance, the actuator 303 may be formed by a coil electromagnet activated when it is traversed by a current. Alternatively, the actuator 303 may be formed by a permanent magnet moved to and away from the valve body 301 for respectively controlling opening and closing of the valve 300. The actuator 303 faces the valve body 301 in proximity of the wall 306A to be closer to the minor base 302B than to the major base 302A of the shutter 302, or in any case is brought into this position when activated.

Figure 38B:
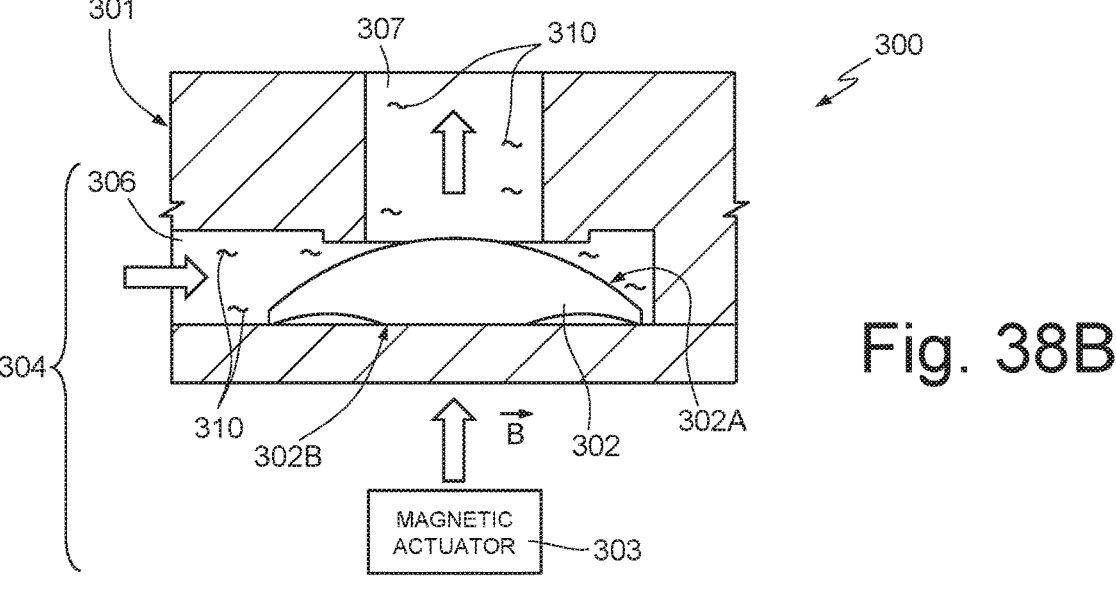
Figure 40:
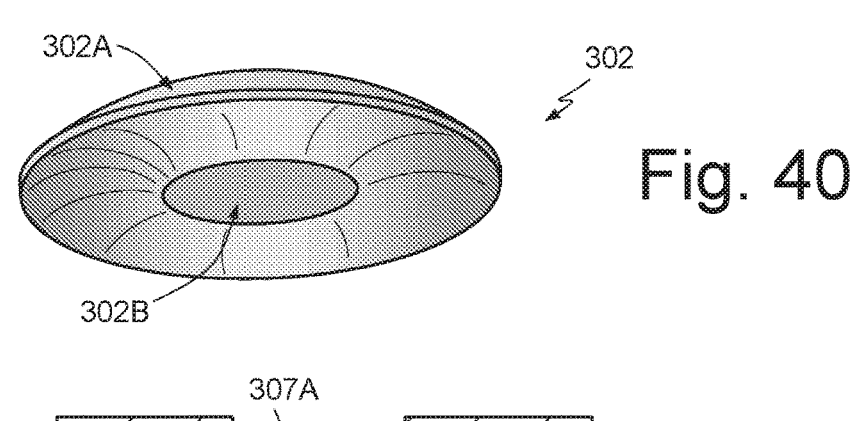
FIG. 40 is a perspective view from below of the magnetic valve of FIG. 38B, in the deformed condition.

When the actuator 303 is activated (turned on or moved to the coupling 309 of the valve 300), the thereby generated magnetic field B attracts the ferrite particles or powder and causes deformation of the shutter 302, as shown in FIGS. 38B and 40. In practice, the conical portion of the shutter 302 forms a circular "wing" (on the sides, in FIG. 38B) that is attracted by the actuator 303 and turns over towards the minor base 302B of the shutter 302, detaching from the peripheral projection 308 and freeing the opening 307A. The fluid 310 in the first duct portion 306 can thus flow towards the second duct portion 307 in the direction indicated by the arrows of FIG. 38B.

When the actuator 303 is deactivated (turned off or moved away), thanks to the elasticity of the material of the shutter 302, it returns into its undeformed configuration, thus closing again the opening 307A.

With the embodiment of FIGS. 39 and 40, excellent valve closing and ease of actuation are thus obtained. In particular, thanks to its symmetry, the shutter 302 exerts a uniform sealing action on its entire contact surface (peripheral ribbing 308) in the closed condition, providing a maximum effectiveness and sealing reliability. Furthermore, when the shutter is deformed by the actuator 303, it undergoes deformation in a symmetrical way, preventing internal stresses caused by stiffness differences due to geometrical reasons.

Alternatively, the shutter 302 may have a frustopyramidal shape, a frustoprismatic shape, or a more complex shape.

Figure 41:
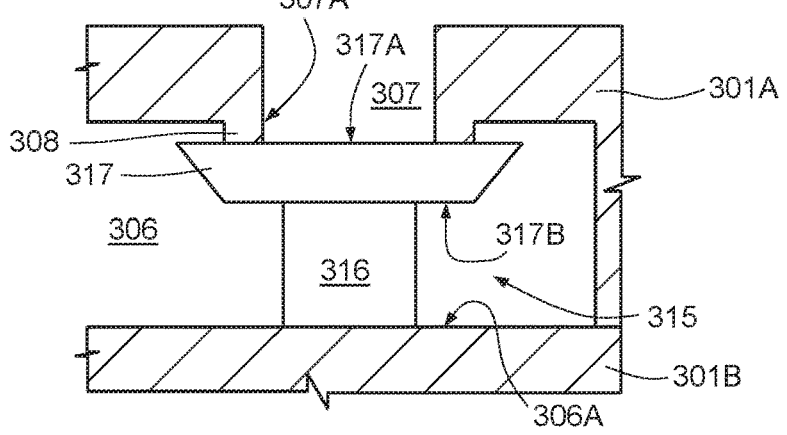
FIGS. 41-43 show variants of the magnetic valve of FIGS. 38-40.
Figure 42:
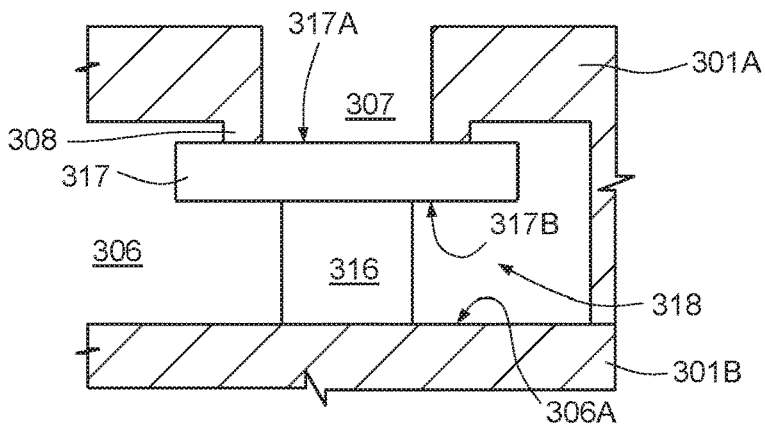
Figure 43:
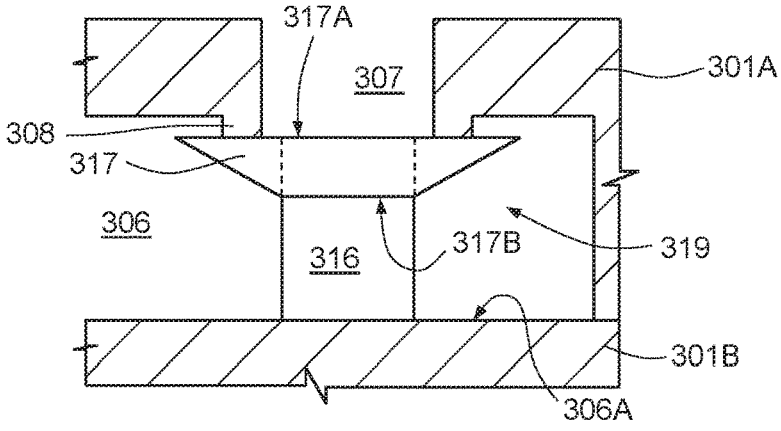

FIGS. 41-43 show shape variants of the shutter 302, designated by 315, 318, and 319, respectively, which may be useful in particular conditions, for example in case of a first path portion 306 of a large width. The shutters 315, 318 and 319 are formed by two parts: a stem portion 316 and a shutter portion 317, bonded together. The stem portion 316 and the shutter portion 317 may be of a different material. For example, the stem portion 316 may be non-ferromagnetic and/or non-elastic material, such as plastic, metal, or a polymer and may thus be deformable or not. The shutter portion 317 is, instead, of ferromagnetic elastic material, as described above for the shutter 302.

In all of FIGS. 41-43, the base portion 316 of the shutter 315, 318, 319 rests against, for example is bonded to, the wall 306A of the first path portion 306, and the shutter portion 317 rests against the peripheral ribbing 308 with its major base 317A that closes the opening 307A.

In detail, the shutter 315 of FIG. 41 has a frustoconical-shaped shutter portion 317, as in FIGS. 39A and 39B, with its major base 317A in contact with the opening 307A and its minor base 317B having a greater area than the base portion 316. Alternatively, the open/close portion 317 of the shutter 315 may be frustopyramidal-regular prism-shaped.

The shutter 318 of FIG. 42 has a parallelepiped-cube- or cylinder-shaped shutter portion 317, with a greater area than the base portion 316.

The shutter 319 of FIG. 43 has a cone-, pyramid-, or prismatic ring-shaped shutter portion 317, with a central hole through which the base portion 316 is inserted.

In all the solutions of FIGS. 39-43, the valve body 301 may be a single piece and the shutters 302, 315, 38 and 319 may be pressed into the valve body 301. Alternatively, the valve body 301 may be made up of two parts: a first part 301A housing the first and second path portions 306, 307 (where the first path portion 306 is open at the side intended to form the wall portion 306A of the first path portion 306); and a second part 301B closing the first path portion 306, forming the wall portion 306A. For instance, the second part may be a chip or a film. In this way, insertion of the shutter is facilitated, and the shutter 302, 315, 318, and 319 is slightly compressed when the two parts of the valve body are bonded together.

As referred to above, the connector group 221 may be used in the system 1 and 1' according to FIGS. 1-19. In particular, the shutter 302, 315, 318, or 319 may form the magnetic bodies 140-142.

Figure 44:
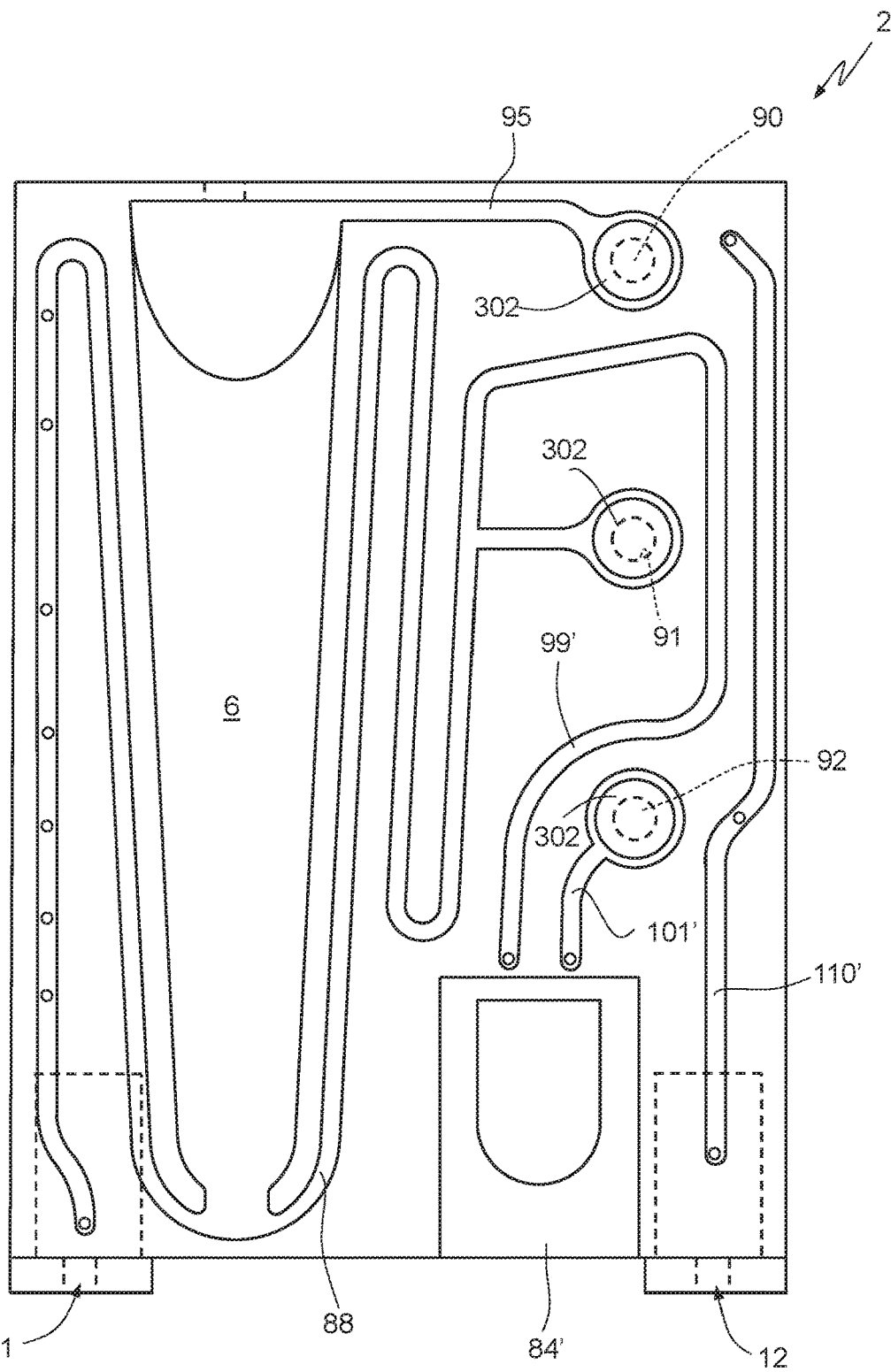
FIG. 44 shows the magnetic valve of FIGS. 40-42 applied to the cartridge 2' of FIGS. 13-15.

For instance, FIG. 44 shows the cartridge 2' used in the system of FIG. 11 and shown in detail in FIGS. 13-15. In this case, the valve body 301 may form the main body 80', and the second closing wall 82; the shutter 302/315/318/319 forms the magnetic bodies 140-142, as referred to above; the first path portion 306 forms the first vent recess 95, the output fluidic recess 88, and the second vent recess 101; and the second path portion 307 forms the first, second, and third valve holes 90-92. The same applies to the cartridge 2 used in the system of FIG. 1 and shown in detail in FIGS. 4-6, with the difference that the first path portion 306 forms the first vent recess 95, the output fluidic recess 88, and the second vent recess 101. Thus, in a not shown manner, the valve holes 90-92 of the cartridges 2 and 2' may have a respective peripheral projection 308 (not shown).

For the cartridges 2 and 2', closing of the second path portion 307 (valve holes 90-92) is favored by the suction pressure applied downstream of the valve holes 90-92, as described in detail in FIGS. 7-10 for the cartridge 2 and in FIGS. 16-19 for the cartridge 2'.

When incorporated in the cartridge 2 or 2', the shutter 302 (the shutter portion 317) has a diameter of the major base 302A of 4-7 mm, typically about 6 mm, a diameter of the minor base 302B of 1.5-4 mm, typically about 2.3 mm, and an overall height of 1-mm, typically about 1.3 mm, and the cylindrical portion (forming the major base) has a height of 0.1-0.3 mm, typically about 0.2 mm.

In the shown embodiment, the magnetic valve 300 forms a normally closed valve, opened by deformation of the shutter or shutter portion 302, 317. It thus enables a duct/hole/channel/recess to be closed in a reliable, simple, and inexpensive way and to be controlled using a simple magnetic actuator. With the shown arrangement, with the major base 302B facing the downstream duct portion (second path portion 307), the fluid pressure and possible forces acting on the fluid favor tightness. The presence of the peripheral projection 308 in turn favors hermetic seal, since the compression of the elastic material forming the shutter 302 (or the shutter portion 317) generates a concentrated force in a small area (area of contact between the shutter 302 or shutter portion 317 and the peripheral projection 308).

Even though FIGS. 38-44 show a magnetic valve 300 arranged at the T-coupling 309 between two path portions 306, 307, with an appropriate geometry of the coupling portion, the magnetic valve 300 is able to reliably close even two fluidic path portions arranged at an angle other than 90° or even aligned.

Possible implementations of a system for stirring and mixing liquids are described hereinafter and may be used in portable microfluidic devices, such as cartridges for analysis of biological samples, to which reference is made to hereinafter, without any loss of generality.

In cartridges for the analysis of biological samples, due to their small dimensions and their use outside specialized laboratories and by persons without particular know-how and skills, the problem exists of enabling the intended reactions in the chambers for performing analysis of biological samples in a reliable way, in short times, and with sure results.

To this end, it is useful to have solutions that enable effective mixing of the liquids in the reaction chambers, notwithstanding the small dimensions of the chambers.

Figure 45:
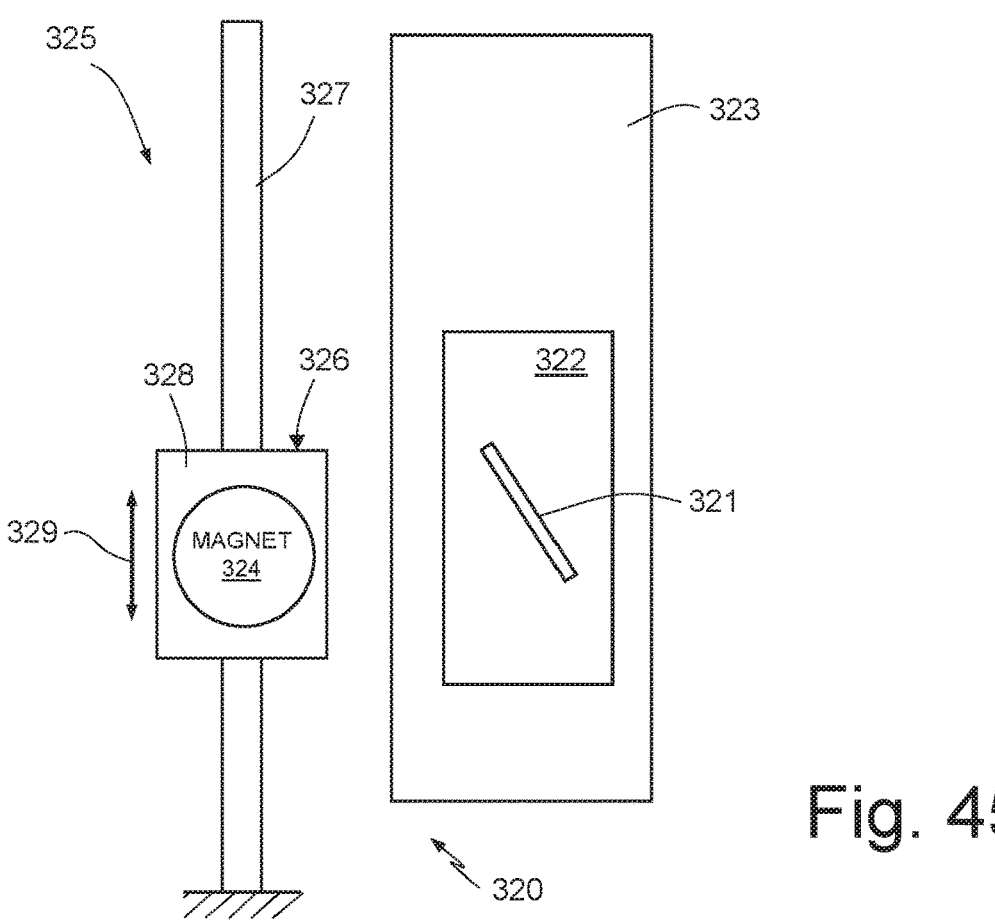
FIG. 45 is a schematic side view of a system for mixing liquids in a microfluidic device.
Figures 46A, 46B:
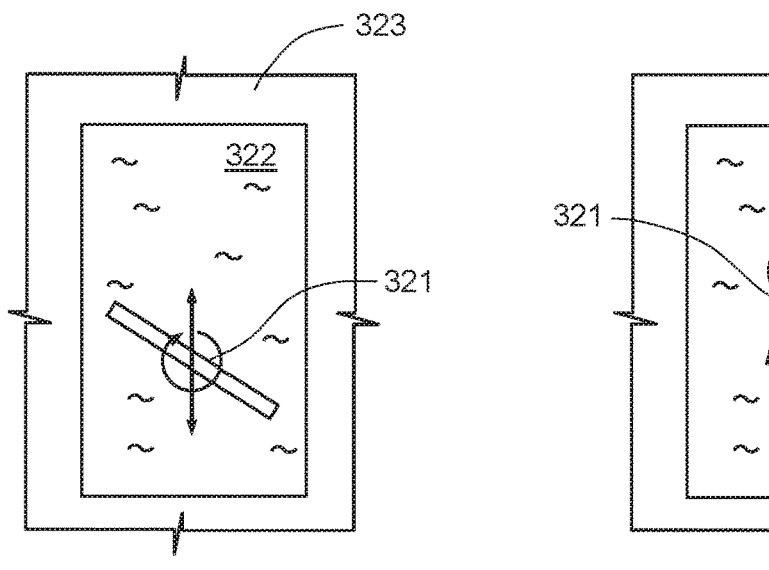
FIGS. 46A and 46B are front views of a portion of the system of FIG. 45 in two different operative steps.
Figure 47:
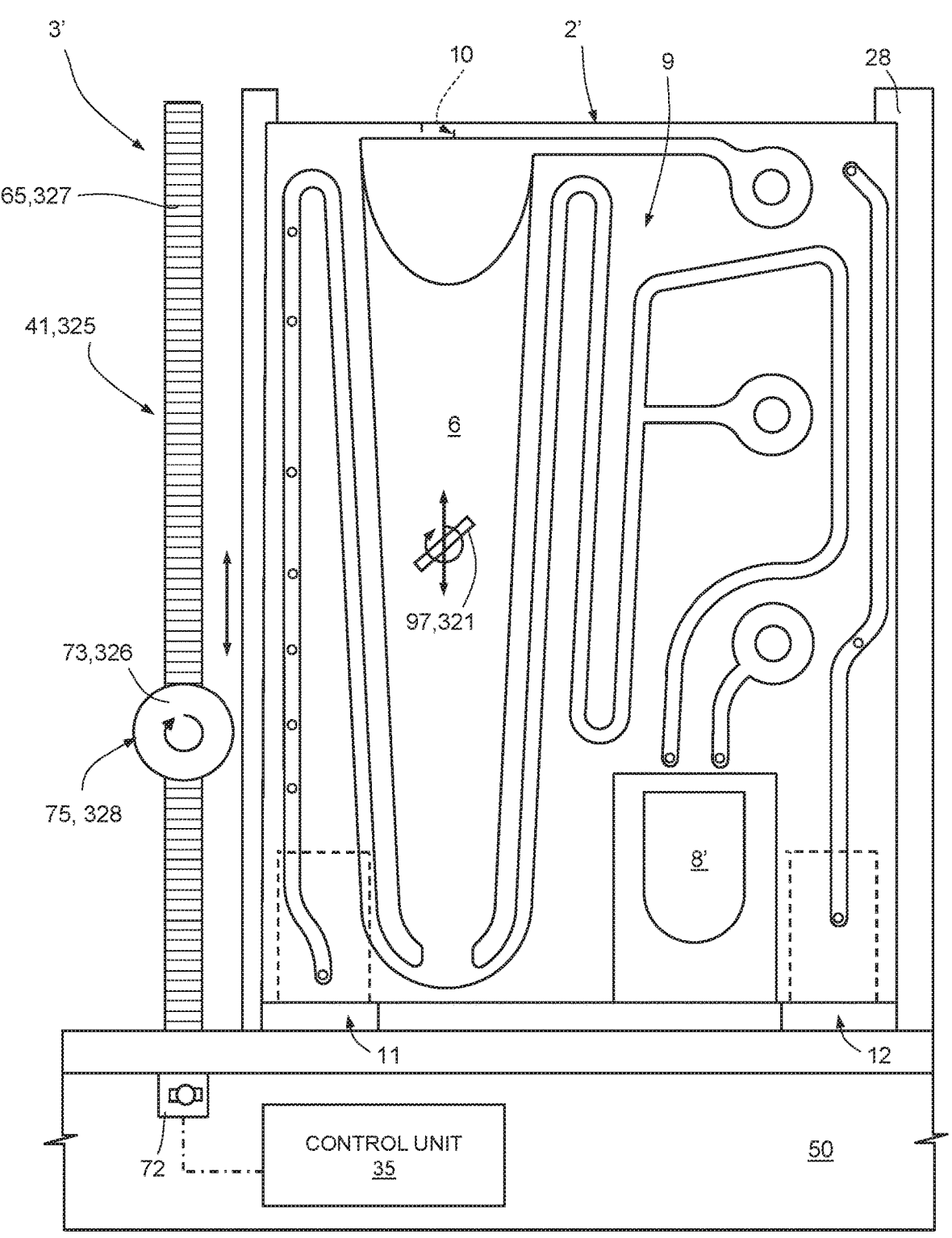
FIG. 47 shows the mixing system of FIG. 45 applied to the cartridge 2 of FIGS. 5-7.

FIGS. 45-47 show an embodiment of a stirring and mixing group 320 having the desired characteristics referred to above and advantageously usable in a microfluidic device during treatment of a liquid sample. For instance, the stirring and mixing group 320 may be used in the cartridges 2 and 2' of FIGS. 1-19, as discussed hereinafter.

According to FIG. 45, the stirring and mixing group 320 comprises a magnetic generator 325 and a microfluidic device (cartridge) 323 having a reaction chamber 322 accommodating a ferromagnetic anchor 321. The ferromagnetic anchor 321 is of ferromagnetic material; for example, it may be completely of stainless steel, or plastic-coated iron, or of any other non-oxidable ferromagnetic material or any other oxidable ferromagnetic material coated with non-oxidable material and inert to the reaction that takes place in the reaction chamber 322.

The ferromagnetic anchor 321 is shaped as a cylindrical rod having a length such as to be able to move inside the reaction chamber 322.

The ferromagnetic anchor 321 is subject to a magnetic field generated by the magnetic generator 325, arranged outside the microfluidic device 323. Typically, the magnetic generator 325 comprises a magnetic element 326 configured to generate a rotating magnetic field. Here, the magnetic element 326 is formed by a permanent magnet 324 mounted on a d.c. motor 328, which can turn horizontally so as to drive the permanent magnet 324 in rotation. Furthermore, the magnetic element 326 of FIG. 45 can be translated along the reaction chamber 322. In the shown example, the reaction chamber 322 has a larger extension in a vertical direction. In this case, the magnetic element 326 is mobile vertically, as indicated by arrow 329. For instance, the magnetic element 326 may be carried by a support 327, for example a worm, coupled to an electric motor (not shown) driving the worm in rotation and enabling translation of the magnetic element 326 along the support 327.

In this way, the permanent magnet 324 can rotate and displace vertically.

In use, when it is desired to obtain mixing inside the reaction chamber 322, the magnetic generator 325 is operated to generate the rotating and translating magnetic field and cause rotation and translation of the ferromagnetic anchor 321 inside the reaction chamber 322, as shown in FIGS. 46A and 46B.

As mentioned above, the stirring and mixing group 320 may advantageously be used in the system 1 and 1' according to FIGS. 1-19. In particular, the microfluidic device 323 may be the cartridge 2 or 2', the reaction chamber 322 may be the extraction chamber 6, the ferromagnetic anchor 321 may be the anchor 97, the magnetic generator 325 may be the anchor actuator 41, the permanent magnet 324 may be the second magnetic element 73, the d.c. motor 328 may be the third motor 75, and the support 327 may form the second turret 65. Moreover, as explained with reference to FIGS. 1 and 2, the second turret 65 may be a worm extending vertically, driven in rotation by the second electric motor 72 arranged in the base 50 and co-operating with a counterthread formed on the casing of the third electric motor 75. The second electric motor 72 is controlled by the control unit 35.

In this case, for a cartridge 2 or 2' having dimensions of 75 mm×50 mm×10 mm, with the extraction chamber 6 having a volume of approximately 1.2 ml and a minimum width of 0.8 mm, the ferromagnetic anchor 321 may have a cylindrical shape, with a length of about 7 mm, a diameter of about 1.5 mm, and a weight of less than 0.1 g. The magnetic element 326 may rotate at a maximum nominal speed of rotation of up to 140 r.p.m., even though the speed in general is not constant and depends upon the friction with the liquid in the reaction chamber and possible magnetic beads (as described above for the treatment of the molecules separated in the extraction chamber, with reference to FIGS. 9 and 18A, 18B).

Figure 48A:
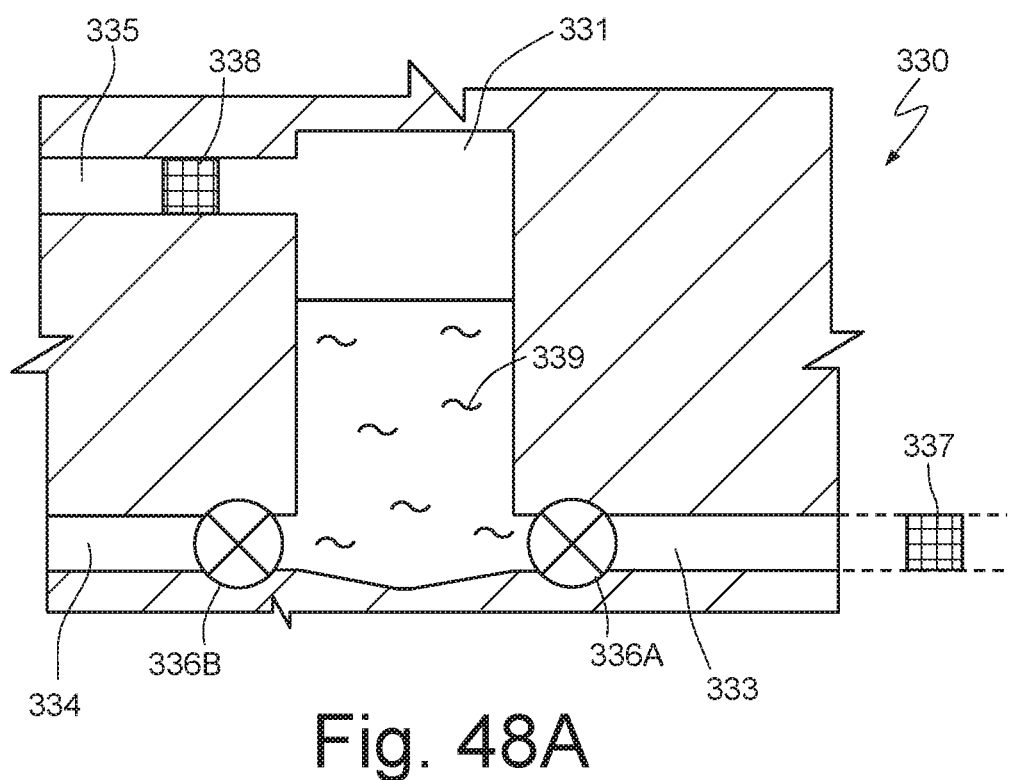
FIGS. 48A and 48B schematically show a cross-section of a microfluidic device during two operative steps.
Figure 48B:
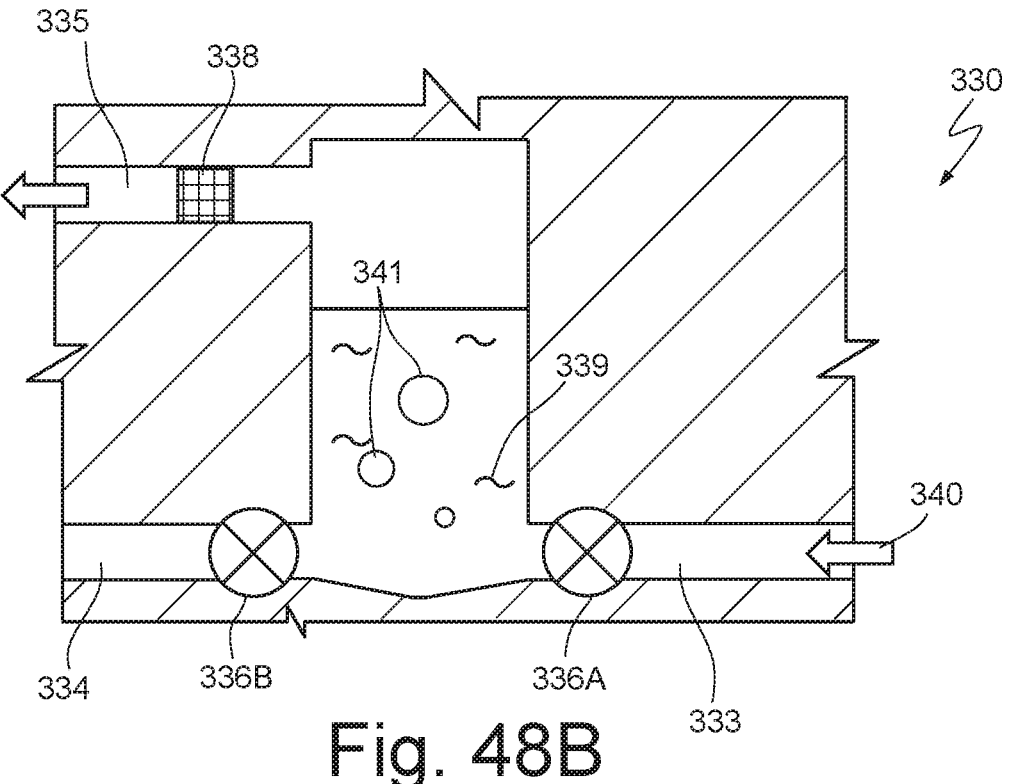
Figure 49:
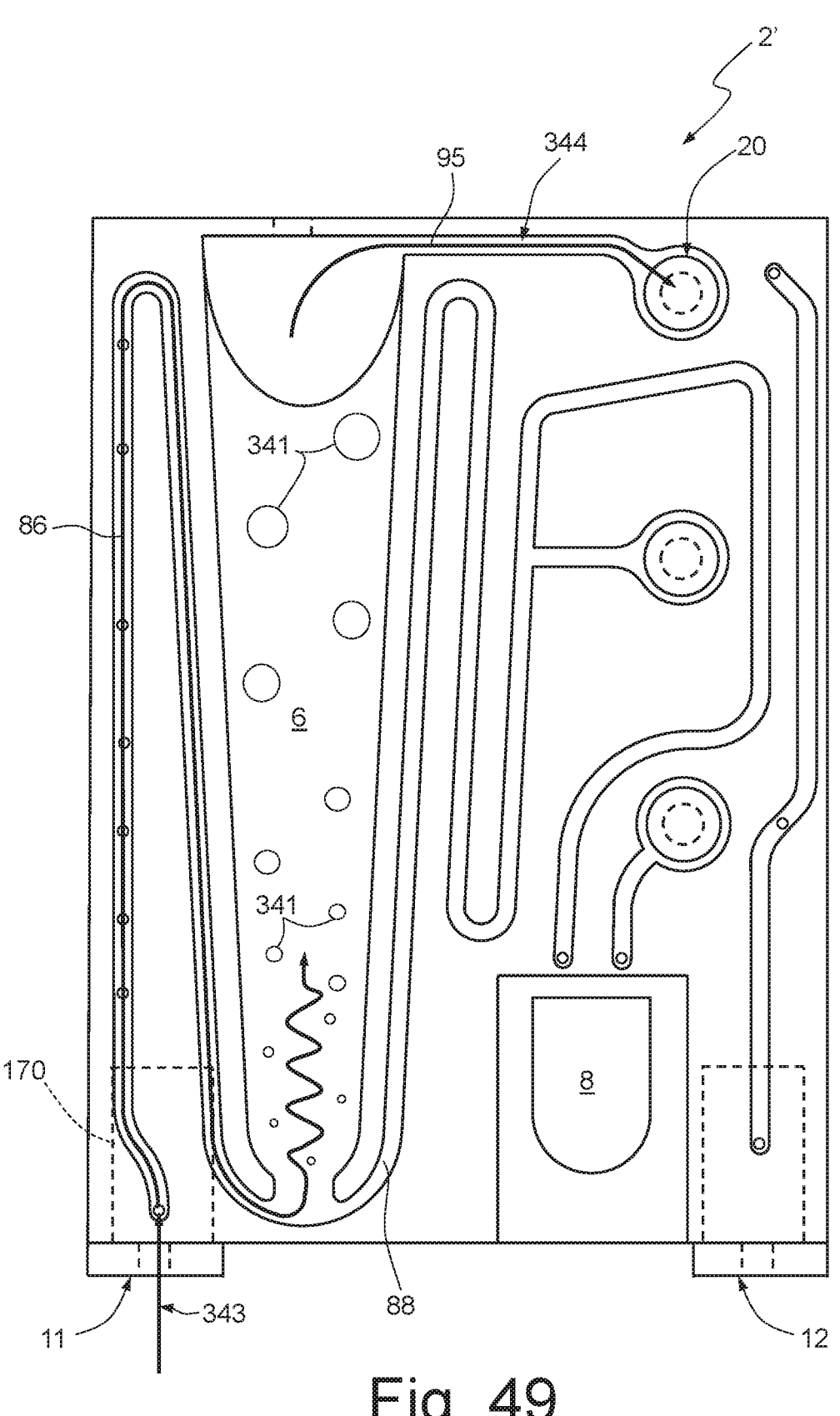
FIG. 49 shows the mixing system of FIGS. 48A and 48B applied to the cartridge 2' of FIGS. 13-15.

FIGS. 48-49 represent another reliable, rapid, and effective solution to obtain stirring and mixing of a liquid in a microfluidic device. This solution may moreover advantageously be used in the cartridges 2 and 2' of FIGS. 1-19, in addition to and/or instead of the solution described with reference to FIGS. 45-47.

Specifically, according to FIGS. 48A and 48B, air, preferably filtered, is bubbled into a reaction chamber 331 of a microfluidic device 330.

In detail, in the microfluidic device 330 of FIGS. 48A and 48B, the reaction chamber 331 is connected to an inlet channel 333, an outlet channel 334, and a vent channel 335. In the shown example, the inlet channel 333 and the outlet channel 334 are arranged near a bottom end of the reaction chamber 331, on opposite sides thereof, and are equipped, respectively, with a first valve 336A and a second valve 336B. The vent channel 335 is connected to a top end of the reaction chamber 331. A first air filter 337 may be arranged upstream of the inlet channel 333 (typically, on the ventilation line 33 of the control machine 3, 3' of FIGS. 1 and 12). A second air filter 338 may be arranged on the vent channel 335, within the cartridge 2, 2'. The first and second filters 337, 338 may be filters of the HEPA (High-Efficiency Particulate Air filter) type. In particular, the first filter 337 has the function of filtering possible pollutants or contaminants upstream of the extraction chamber 6 (FIGS. 1-19) and of the reaction chamber 331. The second filter 338 has the function of preventing potentially dangerous material, such as parts of viruses, from being released into the external environment.

A further valve (not shown) may be provided on the vent channel 335.

In use, initially, the first valve 336A is opened and the second valve 336B is closed. Next, a liquid (designated as a whole by 339) is introduced into the reaction chamber 331 through the inlet channel 333 (FIG. 48A). Then (FIG. 48), by keeping the first valve 336A open and by applying a suction pressure of, for example, $5 \cdot 10^{-2}$ atm to the vent channel 335, air 340 is returned into the reaction chamber 331 through the inlet channel 333. In this way, the air 340 tends to swirl upwards, forming bubbles 341. The bubbles 341 move upwards, causing remixing of the liquid 339.

After traversing the entire volume of liquid 339 in the reaction chamber 331, the air 340 exits from the reaction chamber 331 through the vent channel 335. Here, the air 340 is filtered by the second filter 338 and can thus be discharged towards the outside, without any risk of contamination.

At the end of the treatment in the reaction chamber 331, the second valve 336B is opened, while the first valve 336A is kept open, to enable outflow of air and emptying of the reaction chamber 331.

The mixing solution described above is particularly effective when applied to the cartridge 2 or 2' of FIGS. 1-19. FIG. 49 shows, for example, application to the cartridge 2'. In particular, the microfluidic device 330 may form the cartridge 2 or 2', the reaction chamber 331 may form the extraction chamber 6, the inlet channel 33 may be formed by the inlet fluidic recess 86, the outlet channel may be formed by the output fluidic recess 88, and the vent channel 335 may be formed by the first vent recess 95. Here mixing air 340 is supplied through the fluidic inlet 11, as indicated by arrow 343, and flows off into the first vent recess 95 towards the waste chamber 7, 7' (not visible) through the first fluidic valve 20, as indicated by the arrow 344.

In this way, a very effective system is obtained at very low costs (since it requires only a pumping system and fluidic connections already present in the systems 1 and 1' of FIGS. 1-19).

For instance, mixing via continuous air bubbling of FIGS. 48A, 48B, and 49 is particularly advantageous during the flushing with alcoholic solutions. In this case, tests performed by the present applicant have demonstrated that by blowing air in a continuous way at a flow rate of 60-70 μl/s for example for two minutes results in a highly effective flushing. Furthermore, air bubbling has proven particularly effective if carried out in a discontinuous way during detachment of the extracted nucleic acids from the magnetic beads, as described above with reference to FIGS. 9 and 18A and

18B. In particular, during detachment, air can be supplied for 10 s, with a flow rate of 30 μl/s, followed by 10 s of interruption.

Hereinafter, possible implementations of a solid-reagent containment unit are described and may be used in microfluidic devices, such as sample analysis cartridges containing molecules to be analyzed, for example nucleic acids.

In portable microfluidic devices performing analysis of nucleic acids obtained from biological samples, an area is present, also referred to as analysis chamber, that is loaded both with the nucleic acids (or generic molecules extracted from a sample to be analyzed) and reagents allowing the analysis (referred to hereinafter as assay reagents).

It is convenient for the assay reagents to be preloaded into the microfluidic device to enable easier use thereof. The term "preloading" indicates the introduction of the reagents into the device during assembly thereof, i.e., prior to its use. With this strategy, the end operator during use merely has to introduce the sample to be analyzed into the device, with one simple operation, without having to prepare complex reaction mixtures to be introduced into the microfluidic device.

However, many reagents used for biochemical analyses (for example, the reaction mixtures for real-time PCR, which include perishable reagents, such as enzymes and fluorophores) have to be stored at a low temperature (between −20° C. and +4° C.) if in a classic liquid form. It would be far from practical to preload these reagents in liquid form, because the device should then be transported and stored at low temperature, with consequent costs and logistic difficulties. Furthermore, liquid reagents are difficult to confine, and could thus displace during transport/storage, thereby causing problems in the analysis. These displacement problems would increase further when the device has multiple analysis chambers having a common connection prior to start the analysis. In the latter case, during transport/storage of the microfluidic device, liquid displacement between the various analysis chambers may occur, with consequent mixing of different reagents, which could affect the results.

It is, instead, convenient to preload the assay reagents in solid form, i.e., dehydrated, for two reasons. First, the perishable reagents thus become stable also at room temperature, since the practically total absence of water determines a considerable deceleration of the reaction kinetics, including those of the degradation processes of the reagents. Thus, in this way, the need is avoided to maintain a cold chain for the device during entire transport and storage thereof. Furthermore, the solid reagents are intrinsically more stable also from the "mechanical" standpoint; any displacements of the reagents from their own location become less likely, above all if the analysis chamber or chambers is/are designed with an appropriate shape or shapes (as will be described hereinafter).

The reagents may be introduced into the device already in solid form, or in liquid form and then be dehydrated (for example, via lyophilization) in situ immediately after. Next, the device is assembled in dry, controlled atmosphere to prevent any undesired re-hydration of the solid reagents by air humidity, which would jeopardize both chemical and mechanical stability thereof.

In general, once assembly of the device is concluded with the solid reagents on board, it is sealed within a package at controlled atmosphere that does not allow penetration of humidity from the external air. Furthermore, albeit using a humidity-proof package, in many cases it is desirable for the containment structure to be resistant to humidity to reduce further the probability of undesirable re-hydration of the solid reagents. Such re-hydration could occur accidentally during transport/storage, but also while introducing the sample into the portable microfluidic device for use thereof. In this step, in fact, the protective package is opened, and undesirable re-hydration may occur even in a very rapid way. Moreover, if the sample is processed in the microfluidic device prior to analysis (for example, if a preventive purification of DNA/RNA is obtained), the time between opening of the package and start of the analysis increases, and thus the probabilities of undesirable re-hydration increase.

Finally, it is desirable for the solid reagents not to be able to displace within the containment structure either during packaging or during storage and transport, or during handling of the microfluidic device when it is used.

FIGS. 50A-50D show manufacturing steps of an embodiment of a unit for containing solid, particular dried reagents, hereinafter referred to as reagent unit 350, which satisfies the above requirements.

Figures 50A, 50B, 50C, 50D, 50E:
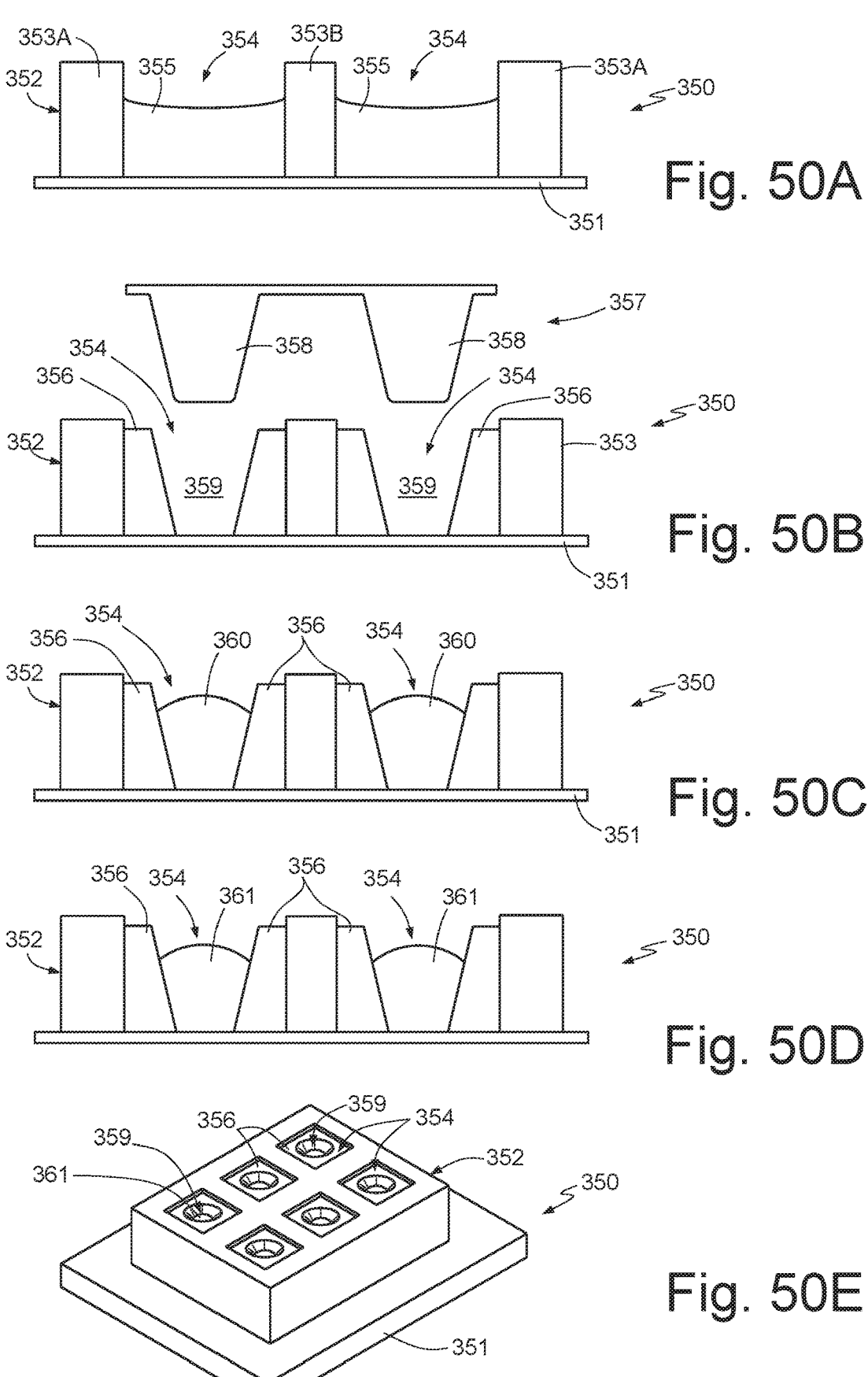
FIGS. 50A-50D are cross-sections of a solid-reagent containment unit, according to a further aspect of the present disclosure, in successive manufacturing steps.
FIG. 50E is a perspective view of the unit of FIG. 50D.

According to FIG. 50A, the reagent unit 350 is manufactured starting from a support 351 bonded, for example glued, to a frame body 352. In the embodiment shown in FIGS. 50A-50D, the frame body 352 comprises a frame 353A with rectangular base and a plurality of delimiting walls or diaphragms 353B, which delimit from each other a plurality of analysis cells 354 (two whereof are visible in FIG. 50A). Alternatively, the frame body 352 may comprise just the frame 353A, as discussed hereinafter with reference to FIG. 58. The support 351 may be of any material, for example silicon, and form an integrated-circuit chip, and the frame body 352 may also be of any material, for example molded polycarbonate. The analysis cells 354 are thus open on one side and have a base of any shape, for example square or rectangular.

According to FIG. 50A, a holding material 355, for example wax and more in particular a paraffin, is introduced into the cells 354 in the liquid state. The holding material 355 may be introduced using an automatic pipettor or by hand pipetting, by virtue of its low melting point. For instance, paraffin "Paraffin wax," produced by Sigma-Aldrich, product code 76228, having a melting point of 44-46° C. and "Paraffin wax" produced by Sigma-Aldrich, product code 327204, having a melting point of 53-57° C., may be used. Other materials may be used instead of wax, provided that they have a similar behavior as regards the application considered and thus:

are inert with respect to the reagents treated in the reagent unit 350;
   do not interfere with the reactions taking place in the reagent unit;
   have a melting point such as not to interfere with the intended analysis processes (as discussed hereinafter with reference to FIGS. 57A-57C);
   do not melt during transport/storage; and
   have a low volatility in the temperature range of interest.
   Preferably, moreover, the holding material 355 has the following characteristics:
   it is less dense than the solutions of the treated reagents; and
   it is transparent at the wavelengths of interest (if a treatment step, for example detection, of an optical type is provided for).
   For instance, in addition to paraffin, other waxes may be used, such as bees wax, or polymers such as polycaprolactone, or solid fats, such as cocoa butter, or a gel, such as hydrogel or organogel.

In general, the holding material 355 is an adhesion material that can be embossed at lower temperatures than its own melting point. For instance, it can be embossed at temperatures lower by 5-10° C. than its own melting point. Furthermore, the holding material 355 has a melting point lower than 62° C., preferably lower than 60° C., even more preferably lower than 58° C.

Then, the holding material 355 is allowed to cool until it solidifies. Next (FIG. 50B), a hot-embossing step is carried out using a first mold 357 in order to provide a reagent cavity 359 in each analysis cell 354.

Figure 53A:
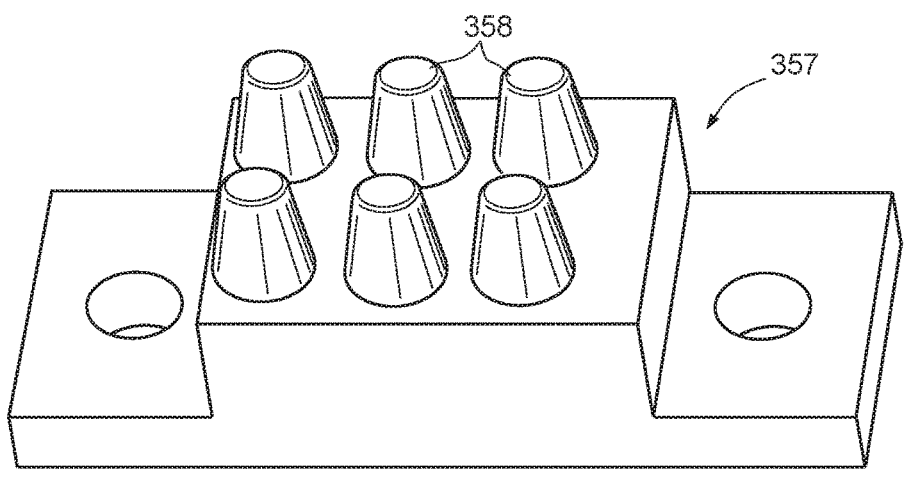
FIGS. 53A-53C are perspective views of different embossing tools used in the steps of FIGS. 50B and 52A.

In particular, for the embossing six analysis cells 354 arranged side-by-side two by two in three rows, the first mold 357 shown in FIG. 53A may be used. Here, the first mold 357 comprises six first embossing elements 358 having a projecting frustoconical shape, one for each analysis cell 354. For instance, each first embossing element 358 may have a base with a diameter of 2.5-3 mm, in particular 2.8 mm, and the generatrices of the conical shape may have an angle of approximately 10° with respect to the vertical.

The embossing temperature depends upon the used holding material; in particular, it is set approximately 5-10° C. lower than the melting point of the material. For instance, in case of paraffin, which, as mentioned, has a melting point of 44°–46° C., the embossing temperature is chosen in the range 35-40° C., for example 38° C., so as to not cause melting of the holding material, but only softening thereof.

As a result of the embossing operation, the reagent cavity 359 in each analysis cell 354 here has a frustoconical shape, delimited by retention walls 356 formed by the displaced holding material, and extends throughout the thickness of the retention walls 356 (it is a through cavity).

In FIG. 50C, a liquid reagent 360 (comprising one or more reagent substances, according to the application of the reagent unit 350) is added in the reagent cavities 359 and then (FIG. 50D) dehydrated, for example lyophilized, in a known manner, to form a dried reagent 361 within the reagent cavity 359.

The reagent unit 350 thus prepared (see also FIG. 50E) can then be put in a sealed package that acts also as barrier as regards humidity, for storage and transport.

During transport and storage of the reagent unit 350, and while opening its package for use, the retention walls 356 may exert an adhesion action on the dried reagent 361, keeping it in position in the cells and preventing it from exiting the analysis cells 354.

Figure 51:
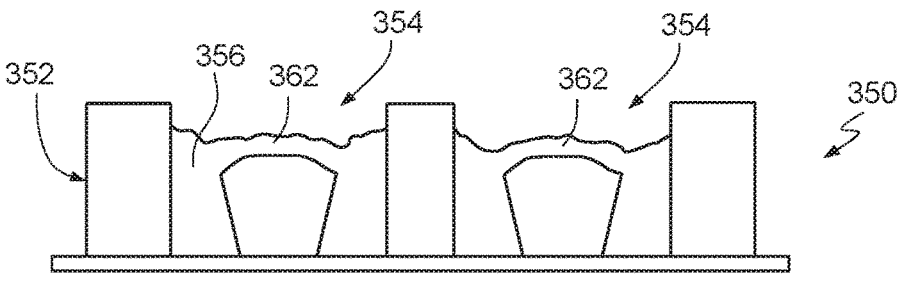
FIG. 51 is a cross-section of the solid-reagent containment unit of FIGS. 50A-50D in a possible subsequent manufacturing step.

According to a different embodiment, after dehydration, the reagent unit 350 is heated to a temperature close or equal to the melting point of the holding material of the retention walls 356. In this situation, as shown in FIG. 51, the retention walls 356 partially melt to form a sort of crust or plug wall 362 on top of the dried reagent 361. The dried reagent 361 is thus surrounded by a structure (formed by the support 351, the retention walls 356 and the plug wall 362) that envelops it on all sides, protects it, and isolates it from the external environment. Since the material of the retention walls 356, and thus of the plug wall 362, is inert, does not react with the dried reagent 361 during heating, storage, and analysis.

Figure 52A:
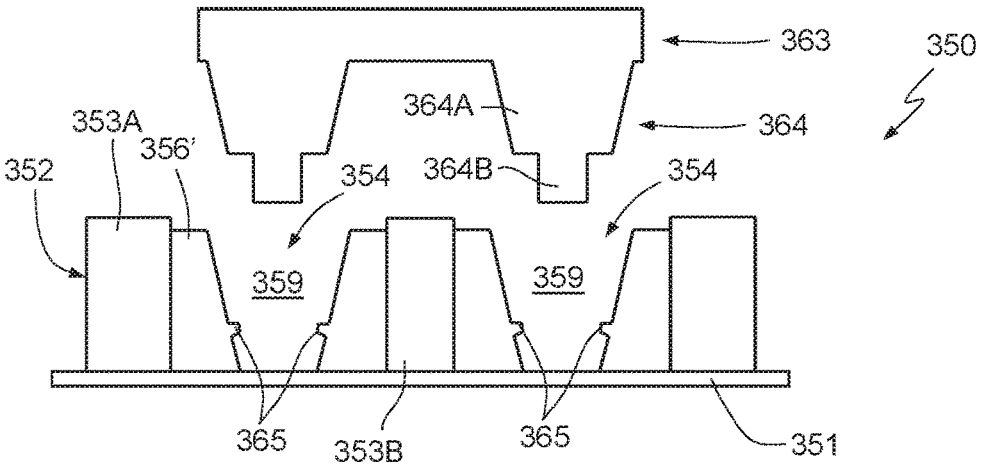
FIGS. 52A-52B are cross-sections of a variant embodiment of the solid-reagent containment unit in two successive manufacturing steps.
Figure 52B:
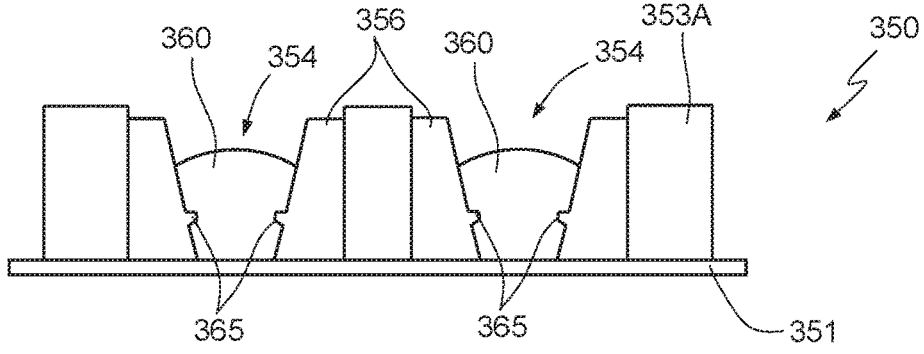

To improve adhesion of the dried reagent 361 (some dehydrated reagents have lower properties of adhesion to wax) it is possible to create mechanical retention structures along the retention walls 356, as shown in FIGS. 52A and 52B.

In detail, according to this embodiment, after forming the retention walls 356 according to FIGS. 50A and 50B (and thus using the first mold 357), these walls 356 are treated so as to form a sort of step or detent 365 projecting towards the inside of each reagent cavity 359. To this end (FIG. 52A), the reagent unit 350 is subject to a second embossing step, using a second mold 363, for example of the type shown in FIG. 53B or 53C. In detail, the second mold 363 comprises a plurality of second embossing elements 364, one for each analysis cell 354, analogously to the first mold 357. The second embossing elements 364 of the second mold 363 are formed by two mold portions: a first mold portion 364A (for example, having a frustoconical shape) having a minor base, with a first area, and a second mold portion 364B projecting from the first mold portion 364A and defining a tip or abutting surface intended to rest against the support 351 of the reagent unit 350. The second mold portion 364B has, for example, a cylindrical shape and a base, with a second area smaller than the first area. The first mold portion 364A has the function of forming the detent 365, whereas the second mold portion 364B has only a stop function during emboss-ing. Thus, the first area of the first mold portion 364A is also larger than a cross-section area of the first embossing elements 358 of FIGS. 50B and 53A arranged at the same distance from the abutting surface of the first embossing elements 358. The base area of the second mold portion 364B is smaller than the abutting surface area of the first embossing elements 358 of FIGS. 50B and 53A. For instance, the first mold portion 364A may have a major base of 3-3.4 mm, in particular 3.2 mm, and a minor base of 2.3 mm-2.7 mm, in particular 2.5 mm, and the second mold portion 364B may have a base area of 0.8-1.2 mm, in particular 1 mm. The generatrix of the conical shape of the first mold portion 364A may have an angle of approximately 10° with respect to the vertical.

Figure 53B:
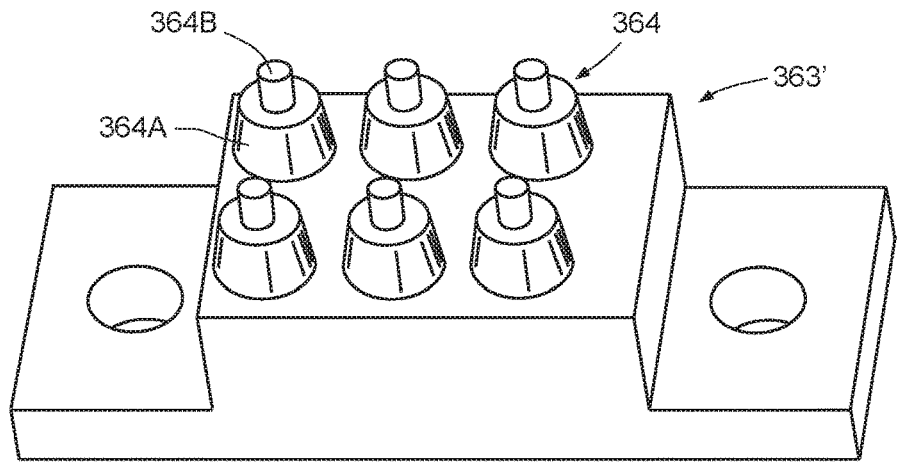
Figure 53C:
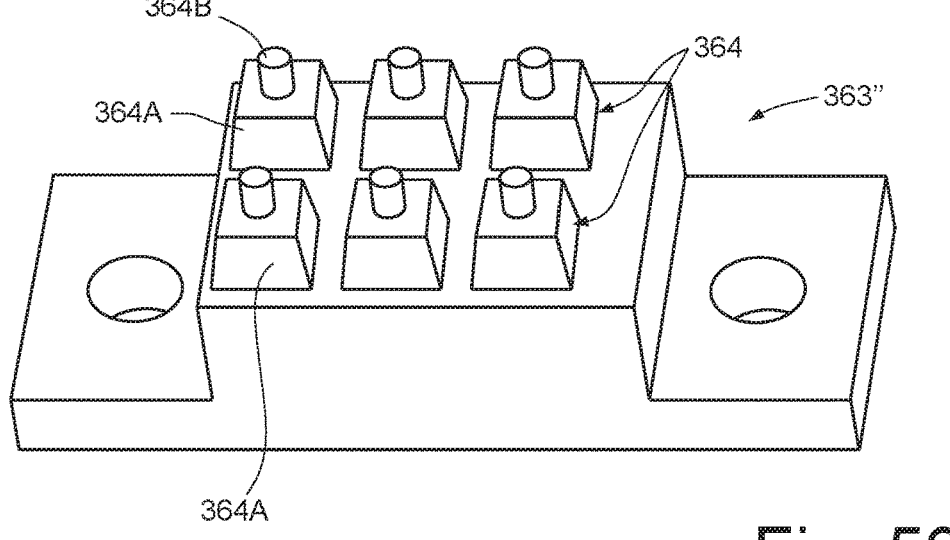

In FIG. 53B, the first mold portion 364A of the second mold (designated by 363') has a conical shape. In FIG. 53C, the first mold portion 364A of the second mold (designated by 363") has a frustopyramidal shape. The second mold portions 364B of the second molds 363' and 363" are both cylindrical. However, the shown shapes are merely exem-plary, and other shapes are possible, provided that they have a first, wider, mold portion and a second, narrower, mold portion, to form a recess, and the first portion 364A of the second mold 363 has at least one dimension larger than the first mold 357 at the same distance from the tip abutting surface of the molds 357, 363.

Due to the larger base area of the first mold portion 364A at the minor base of the first mold 357 at the same height, during the second embossing step, the retention walls 356 are partially squeezed, and part of the material forms the detent 365 extending peripherally towards the inside of the reagent cavity 359 (FIG. 52A).

Then (FIG. 52B), the liquid reagent 360 is introduced into the reagent cavity 359, and the step described with reference to FIG. 50D is carried out, thereby lyophilizing the liquid reagent 360.

The detent 365 thus formed contributes to mechanically blocking the dried reagent 361 and to reliably prevent exit thereof from the reagent cavity 359. Obviously, also in the case of the analysis cell 354 of FIG. 52B, it is possible to provide a plug wall 362, as has been described with refer-ence to FIG. 51 for obtain sealing towards the outside.

Figures 54A, 54B:
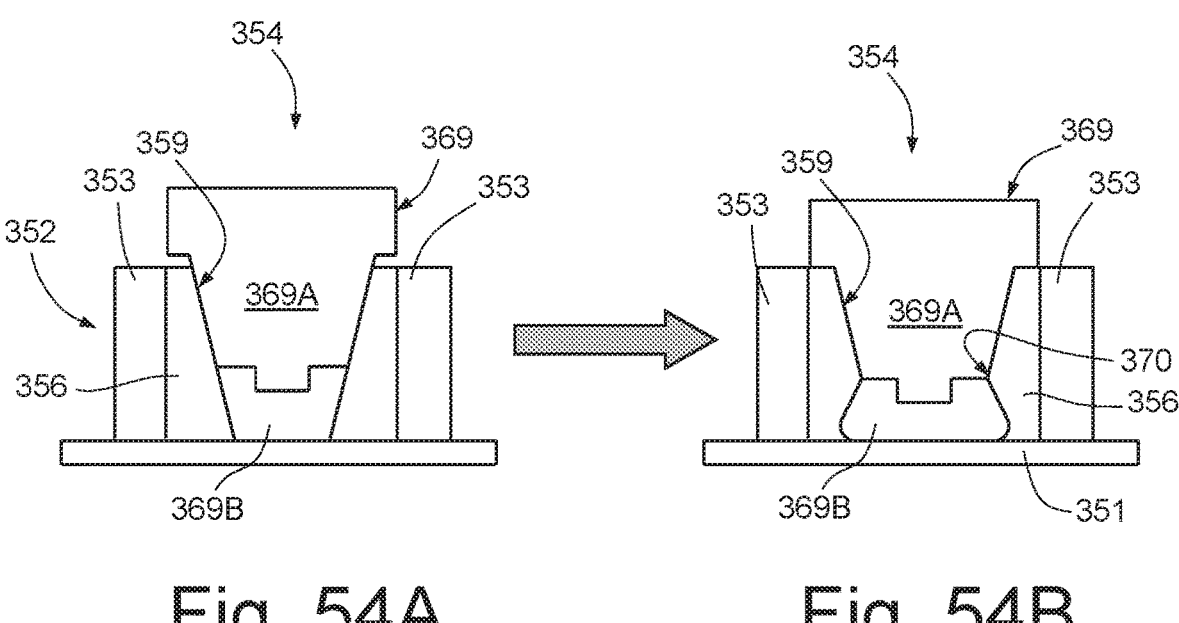
FIGS. 54A and 54B are cross-sections of another embodiment of a solid-reagent containment unit, in successive manufacturing steps.

FIGS. 54A and 54B show a variant of the process for forming the reagent cavities 359. In this case, during embossing, a deformable mold 368 is used (FIG. 55) having embossing elements 369 with a flexible tip so as to be able to cause deformation and widening during the embossing step. For sake of simplicity, FIGS. 54A and 54B show just one analysis cell 354, but the reagent unit 350 may contain any number of analysis cells 354, for example six, as described previously.

Figure 55:
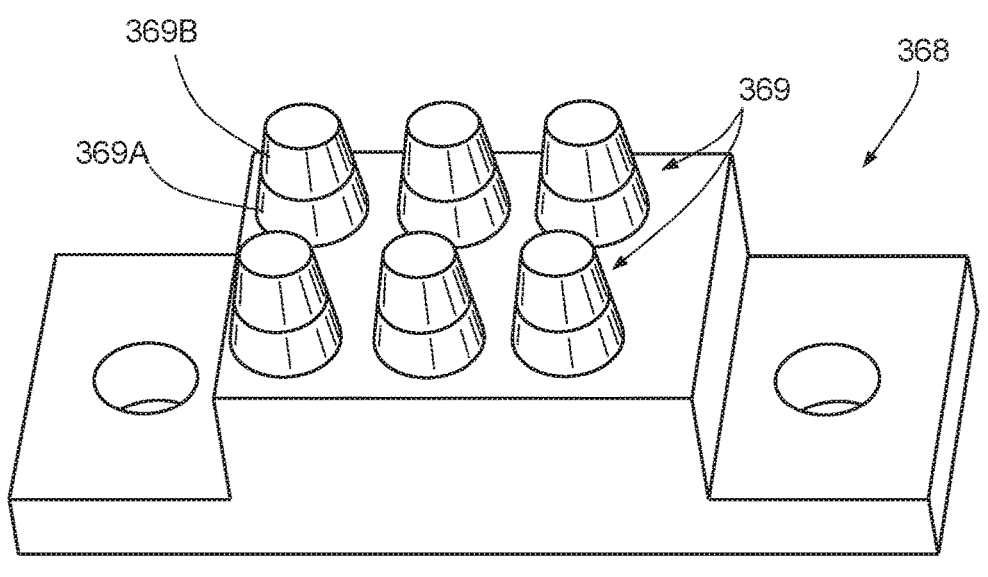
FIG. 55 is a perspective view of an embossing tool used for forming the unit of FIGS. 54A and 54B.

In detail (FIG. 54A), after introducing the holding mate-rial 355 in liquid form and hardening it, the analysis cells 354 are embossed using the deformable mold 368 of FIG. 55. The embossing element 369 here has a generally frus-toconical shape, with a first portion 369A defining the major base, of a first material, which is harder, for example plastic or metal, and a second portion 369B protruding from the first portion 369A and forming the tip or minor base of the embossing element 369, of an elastically deformable mate-rial, for example silicone rubber.

In FIG. 54A, the embossing element 359 is introduced into the analysis cell 354 with a pressure such as not to cause deformation of the second portion 369B of the deformable mold 368. Then a first embossing of the holding material 355 is carried out, and the reagent cavity 359 initially has a frustoconical shape.

Then (FIG. 54B), the embossing element 369 is further pressed against the support 351, causing deformation and lateral widening of the second portion 369B of the emboss-ing element 369 transversely to the embossing direction. Widening of the second portion 369B causes squeezing and displacement of the holding material 355 away from the support 351 so that the reagent cavity 359 assumes an hourglass shape and forms an intermediate neck 370 of minimum area.

The neck 370 here forms a retention structure, which acts on the solid reagent 361 after introducing the liquid reagent and dehydration, as for the detent 365 of FIG. 52B.

Obviously, also for the analysis cell 354 of FIG. 54B it is possible to provide a protective plug 362, for sealing towards the outside.

Figure 56A:
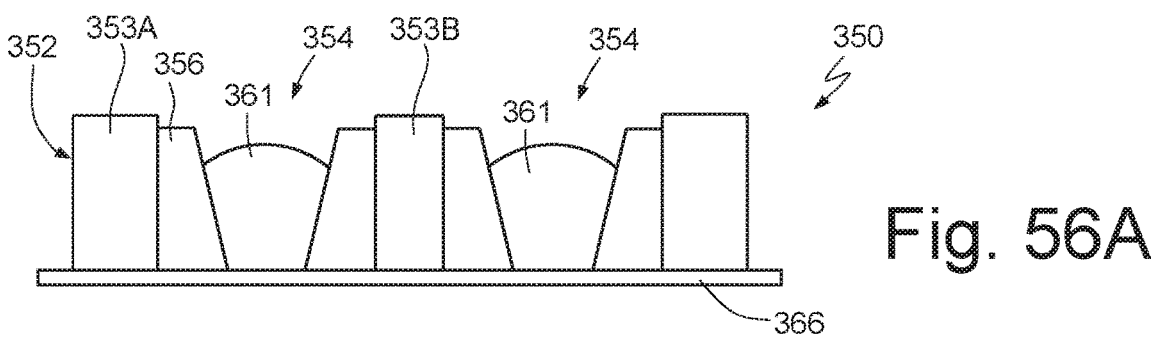
FIGS. 56A-56D are cross-sections of a different embodiment of a solid-reagent containment unit, in successive manufacturing steps.
Figure 56B:
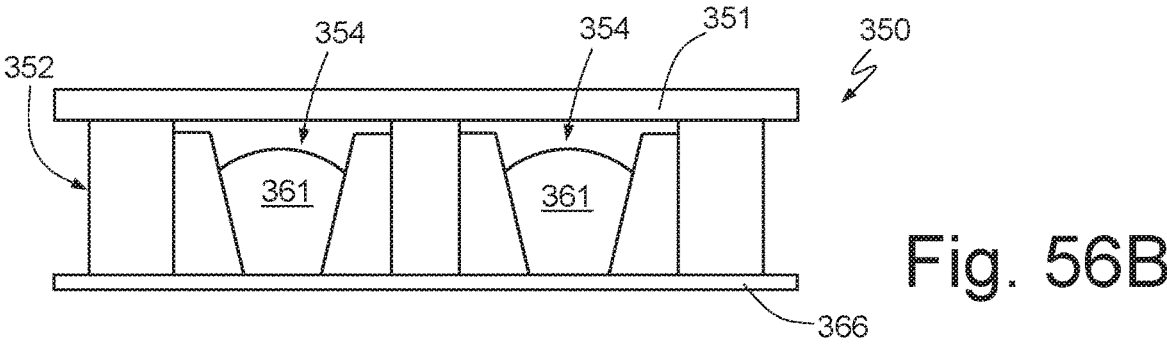

According to the embodiment of FIGS. 56A-56D, ini-tially an adhesive tape 366 is applied that can be removed prior to packaging the reagent unit 350. In detail, FIG. 56A shows the reagent unit 350 after dehydration, and thus containing the dried reagents 361.

Next (FIG. 56B), the support 351 is attached, for example glued, to the frame body 352 on the top side (the side opposite to the adhesive tape 366), thus closing the analysis cells 354 at the top. The support 351 may be a silicon chip, for example integrating heaters and/or electrical or elec-tronic components useful during analysis.

Figure 56C:
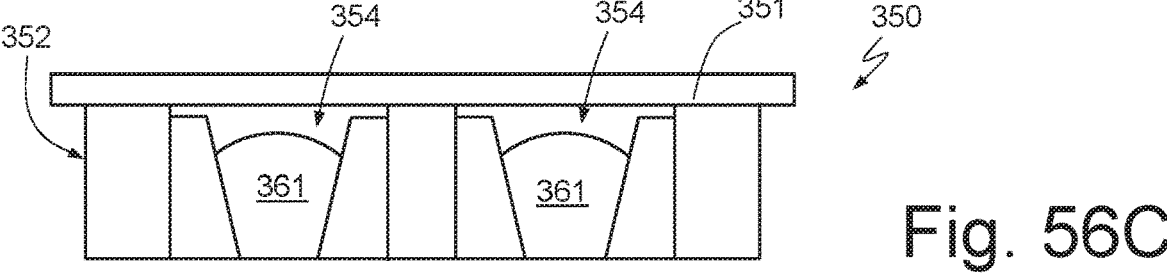
Figure 56D:
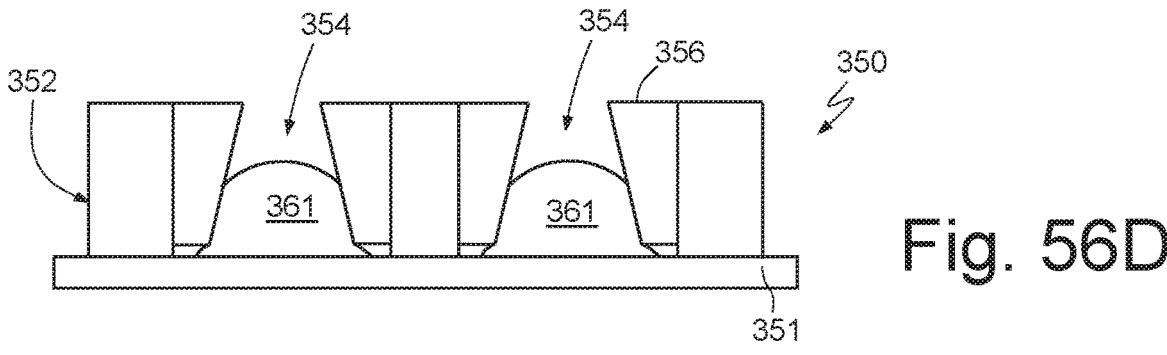

In FIG. 56C, the adhesive tape 366 is stripped off. The dried reagents 361 do not drop, since they are compact and by virtue of the narrowed opening of the analysis cells 354. In FIG. 56D, the reagent unit 350 is turned over. In this step, the dried reagents 361 may slide towards the support 351, but cannot exit the analysis cells 354 due to the narrowed opening of the analysis cells 354, on the side that now faces the external environment, due to the presence of the reten-tion walls 356, as well as, possibly, of the detent 365 (FIG. 52B) or of the neck 370 (FIG. 54B). Then, the reagent unit 350 may be packaged. Alternatively, the adhesive tape 366 may not be removed, and forms a further physical barrier to the displacement of the dried reagents and to the external humidity. In this case, the adhesive tape, if necessary, is removed during use by the end operator.

In all previous embodiments, the reagent unit 350 is introduced into a microfluidic device, for example, a por-table cartridge, to perform the analysis. Insertion may be made prior to packaging, i.e., in the assembly step, and the reagent unit 350 is bonded to the microfluidic device for example by gluing or mechanical fixing. Alternatively, the reagent unit 350 is introduced into the microfluidic device after opening the package by the end user who performs the analysis, and is blocked in situ by simple fitting.

Figures 57A, 57B, 57C, 58, 59:
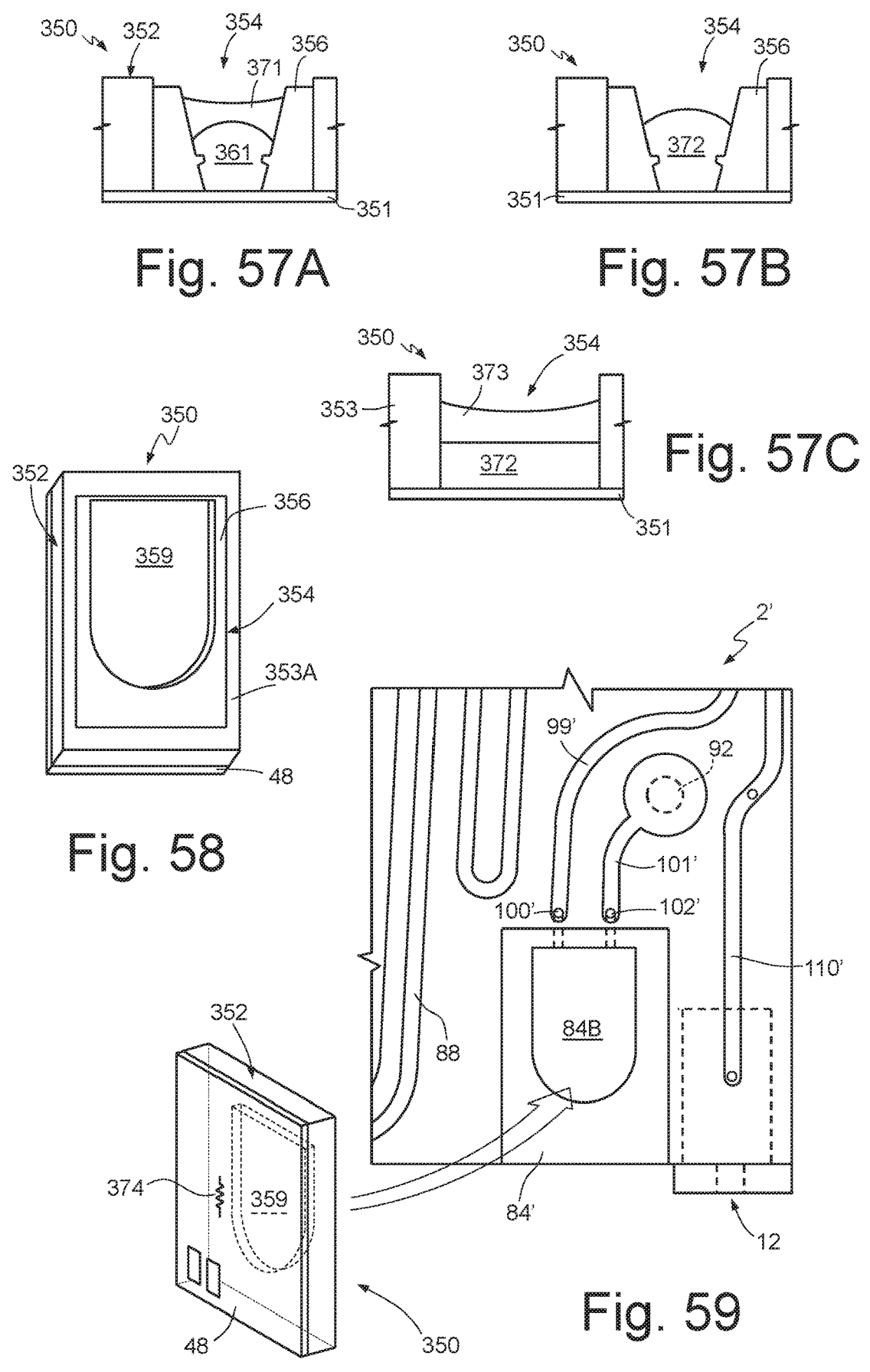

FIGS. 57A-57C show steps of re-hydration of the dried reagent 361, for its preparation to perform a biochemical analysis.

In detail (FIG. 57A), when it is desired to perform an analysis of molecules, for example nucleic acids, the analysis cell 354 is supplied with a sample to be analyzed, in liquid form, designated by 371. After a few seconds, the sample to be analyzed 371 re-hydrates the dried reagent 361 (FIG. 57B) to form a reagent-sample mixture 372; the analysis may then be carried out, according to the provided procedures. During analysis, if so provided (as for real-time PCR), the reagent unit 350 may be heated. This heating is at times obtained at a temperature higher than the melting point of the material of the retention walls 356 (for example, wax, as discussed above). In this case, the retention walls 356 (FIG. 57B) may melt and, due to the lower density of their material as compared to the reagent-sample mixture 372, the former rises at the surface of the mixture 372, to form a closing surface 373 that prevents evaporation of the reagent-sample mixture 372. Here, the mixture 372 is contained between the support 351, the delimiting diaphragms 353, and the closing surface 373.

In any case, since the material of the retention walls 356 and thus of the closing surface 373 (for example, wax) has been chosen according to the criteria described in detail previously, it does not interfere with the analysis.

FIG. 58 shows a reagent unit 350 that may be used in the cartridge 2 or 2' of FIGS. 1-19. The reagent unit 350 of FIG. 58 is of a type with single analysis cell 354. Here, the support 351 is formed by the chip 48 that integrates the heating and temperature-control element, represented schematically in FIG. 59 by a resistor 374. The frame body 352, here comprising just the frame 353A, is bonded to the chip 48. The frame 353A delimits internally a single analysis cell 354, accommodating a retention wall 356 that delimits a bag-shaped reagent cavity 359, which is the same and of the same size as the analysis opening 84B (FIG. 59). The reagent cavity 359 may be obtained, as described with reference to FIGS. 50A-50D, using a mold with a single embossing element similar to the elements 358 of FIG. 50B, but bag-shaped.

FIG. 59 shows insertion of the reagent unit 350 in the analysis recess 84' of the cartridge 2' of FIGS. 14-15, namely, with the reagent cavity 359 facing the analysis opening 84B. In practice, the reagent cavity 359 and the analysis opening 84B form the analysis chamber 8'.

In this way, when the extracted molecules and the elution liquid are fed to the analysis chamber 8' (as described with reference to FIGS. 19A and 19B), they may mix with the dried reagent (here not shown) contained in the analysis cell 354 for performing the analysis.

FIGS. 60-64 show a variant of the reagent unit 350 that contains a plurality of analysis cells 354 and may be applied to the cartridge 2 or 2' of FIGS. 1-19.

In detail, in the reagent unit 350 of FIG. 60, the frame body 352 comprises just the frame 353A and delimits six analysis cells 354 defined completely in the wax or other similar holding material. In practice, a retention structure 375 is arranged therein and has a generally parallelepipedal shape, corresponding both to the retention walls 356 and to the delimiting diaphragms 353 of FIGS. 50-52, 54, 56. The reagent cavities 359 are formed in the retention structure 375. Moreover, a fluidic channel 376 is formed in the retention structure 375, connects together the reagent cavities 359 and extends on a first face 375A of the retention structure 375 (FIG. 62).

A through hole 377 connects the fluidic channel 376 of the retention structure 375 to a second face 375B of the retention structure 375 (FIG. 62).

The retention structure 375 may be obtained using the mold 378 shown in FIG. 61. In detail, the mold 378 has six embossing elements 379 with a frustoconical shape, to form the reagent cavities 359; a projection 380 for forming the through hole 377; and a projecting structure 381 for forming the fluidic channel 376.

In a not shown manner, the reagent cavities 359 in the retention structure 375 may be subject to a second embossing to form teeth similar to the detents 365 of FIGS. 52A-52B. Alternatively, the mold 378 may be modified as in FIG. 55 to have reagent cavities 359 with the shape shown in FIG. 54B.

The reagent unit 350 of FIG. 60, after reagent insertion and dehydration, is bonded to the chip 48 (including possible resistors 374) in the manner shown in FIG. 62, thus with its first face 375A. Then the chip 48 closes the reagent cavities 359 at their major base. To this end, the process described with reference to FIGS. 56A-56D may, for example, be used.

Figure 63:
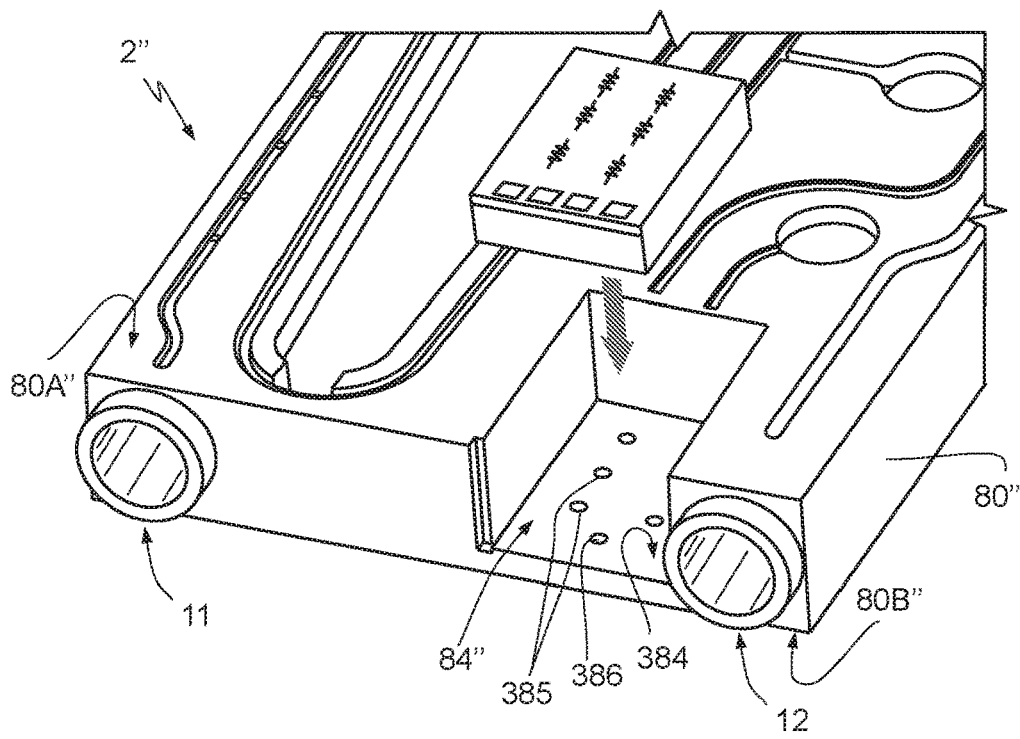
FIG. 63 is a perspective view of the containment unit of FIG. 62 applied to a variant of the cartridge 2 or 2' of FIGS. 4-6 and 13-15.
Figure 64:
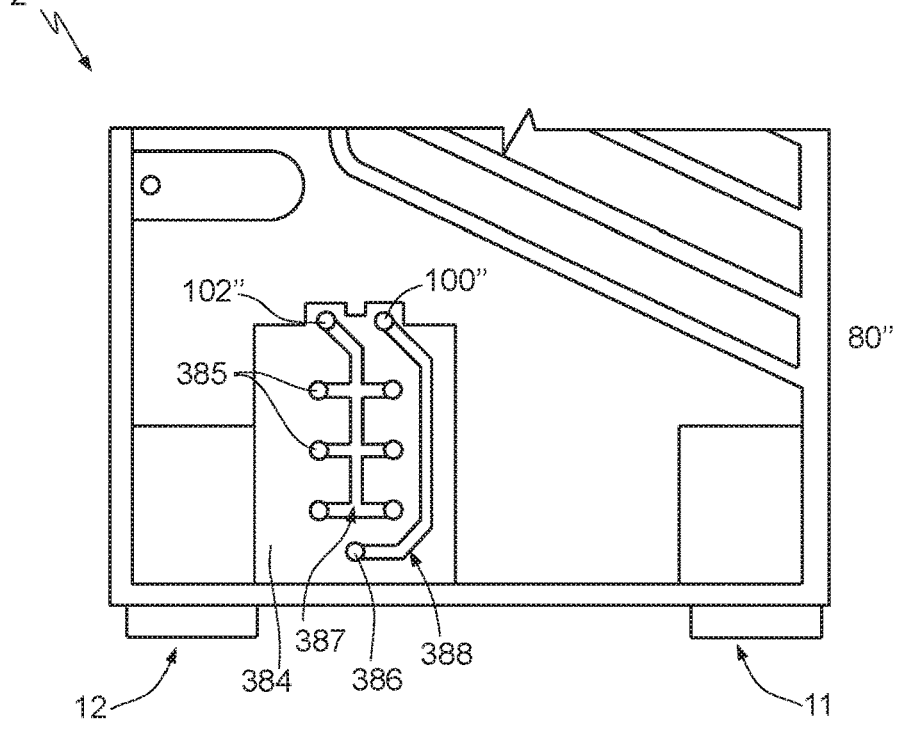
FIG. 64 is a rear view of a part of the cartridge of FIG. 63.

The reagent unit 350, thus fixed to the chip 48, may be mounted in a cartridge 2", as shown in FIGS. 63 and 64. The cartridge 2" has a base structure similar to the cartridges 2 and 2', and thus similar parts are designated by the same reference numbers and the different parts are denoted with prime signs. The cartridge 2" differs substantially from the cartridges 2 and 2' of FIGS. 4-5 and 13-15 in that the analysis recess (here designated by 84", on the first face 80A" of the body 80") does not have the through opening 84B, but is closed by an analysis wall 384 having a plurality of first through holes 385 and one second through hole 386. In detail, the recess 84B of FIGS. 63, 64 has shape and dimensions corresponding to those of the reagent unit 350 so that the latter may be inserted with the second face 375B of the retention structure 375 directed toward the wall 384 of the analysis recess 84". The first holes 385 in the wall 384 of the analysis recess 84" are equal in number to the reagent cavities 359 (here six) and are arranged so as to face, and be in fluidic connection with, the reagent cavities 359 after inserting the reagent unit 350 in the analysis recess 84". The second through hole 386 in the wall 384 of the analysis recess 84" is arranged so as to face, and be in fluidic connection with, the through hole 377 in the retention structure 375.

Moreover, the wall 384 of the analysis recess 84" has, on the second face 80B" of the body 80" of the cartridge 2", a first connection channel 387 connecting the first through holes 385 to a first communication hole 102" similar to the holes 102B and 102' of FIGS. 5-6 and 14-15. The second face 80B" of the body 80" of the cartridge 2" further has a second connection channel 388 connecting the second through hole 386 in the wall 384 of the analysis recess 84" to a second communication hole 100" similar to the holes 100B and 100' of FIGS. 5-6 and 14-15.

In practice, the second connection channel 388 enables connection of the reagent cavities 359 to the extraction chamber 6 and thus loading of the reagent cavities 359 with the extracted molecules and the elution liquid in the steps described with reference to FIGS. 10 and 19A, 19B. Furthermore, the first connection channel 387 enables venting of the reagent cavities 359 while they are being loaded with the extracted molecules and the elution liquid, in the same step.

It is noted that, in this embodiment, the silicon chip, directly facing the reagent cavities 359, has treated areas that have hydrophobic properties on the outside of the reagent cavities 359, to be able to withhold the reagent/sample mixture 371 (FIG. 57B). In fact, the chip 48 is covered, in a known and not shown manner, by a silicon-oxide layer having intrinsic hydrophilic properties. Consequently, when, upon thermal cycles and/or the heating as described with reference to FIG. 57C, the walls separating the reagent cavities 359 (formed by the retention structure 375) melt, eliminating the physical barrier between the reagent cavities 359, the hydrophilic areas surrounded by the hydrophobic areas enable the reagent/sample mixture 371 to be held in position.

For instance, the hydrophobic treatment may be obtained by depositing by lamination an appropriate dry film, for example SINR® manufactured by Shin Etsu, and subsequent lithographical defining to remove it from the areas underlying the reagent cavities 359. Alternatively, a non-dry material may be used, arranged directly in the desired areas by silk-screen printing or direct printing using piezoelectric print heads.

It is noted that, in FIGS. 63-64, the first connection channel 387 allows air to exit when the sample to be analyzed is introduced. The first connection channel 387 may be rendered hydrophobic in the manner referred to above to prevent the reagent/sample mixture 371 from exiting. In an alternative embodiment, if a vent channel connects the reaction chamber(s) to the external environment, a filter, for example an EPA filter, may be provided on the vent to prevent any accidental exit or contamination of the surrounding environment.

Hereinafter, possible implementations of an analysis unit are described, capable of automatically loading a preset amount of a sample containing molecules to be analyzed, for use in microfluidic devices, such as cartridges for analysis of nucleic acids.

As is known, in portable microfluidic devices performing analysis of molecules, for example nucleic acids obtained from biological samples, it is frequently desirable to be able to automatically mix precise amounts of reagents with equally precise amounts of samples to be analyzed.

For instance, in the containment unit 350 described above with reference to FIGS. 50-64, enabling preloading of the reagents in dehydrated form into the containment unit, it is desirable that the sample to be analyzed is supplied to the analysis cells 354 in an automatic way and in a preset stoichiometric proportion with respect to the preloaded reagents. In this way, it is possible to fully exploit the advantages provided by the described containment unit 350, in particular its considerable simplicity of use, the obtainable remarkable reduction in the handling time and minimization of errors.

In general, it is desirable to have a method for mixing of preset amounts of a liquid (for instance, a primary biological sample or a pre-treated biological sample) with solids (typically, dehydrated reagents) preloaded in a controlled amount in an analysis cell.

FIGS. 65A-65D refer to a simplified embodiment of an analysis unit 390 and of a method for loading samples. In particular, these figures refer to the loading of a treated sample containing extracted nucleic acids and an elution liquid, into an analysis cell containing reagents specific for the desired analysis reaction (hereafter referred to as "assay-specific reagents"), for example, for analysis of DNA, without the present disclosure being limited to this application. FIGS. 65A-65D show the analysis unit 390 in the use position; thus the indications such as "up," "down," "top," and "bottom" and the like refer to the shown use position.

Figures 65A, 65B, 65C, 65D:
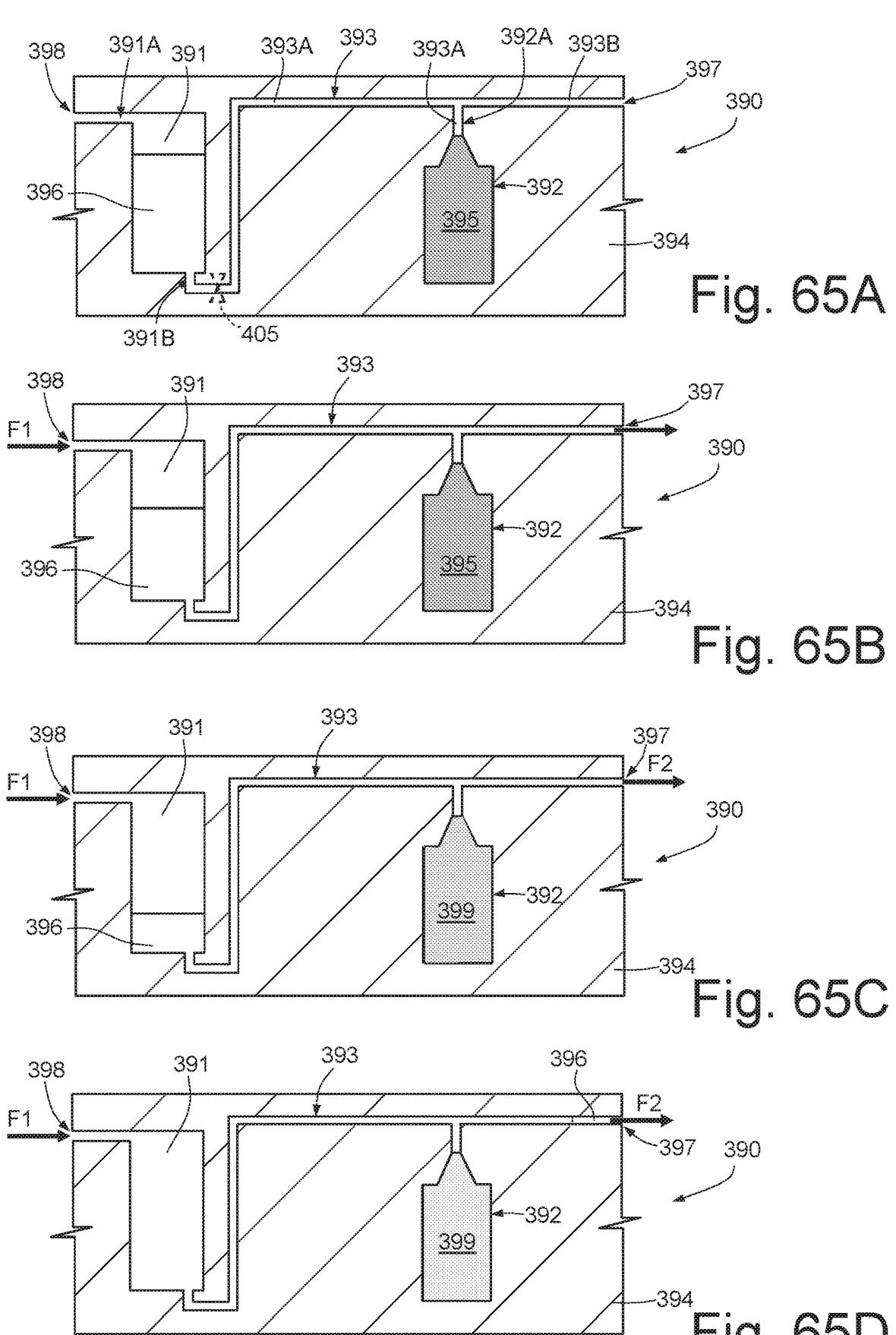
FIGS. 65A-65D are schematic illustrations of an analysis unit according to yet another aspect of the present disclosure, in successive filling steps.

In detail, as shown in FIG. 65A, the analysis unit 390 comprises an analysis body 394 accommodating a first chamber 391 and a second chamber 392; the first and second chambers 391, 392 are connected together by a supply channel 393 extending also in the analysis body 394.

The first and second chambers 391, 392 have respective inlets 391A, 392A arranged near the respective top ends, and the first chamber 391 has an outlet 391B arranged near a bottom end thereof. The supply channel 393 here extends between the outlet 391B of the first chamber 391 and an outlet end 397 of the supply channel 393. Furthermore, the supply channel 393 has a branch 393A connected to the inlet 392A of the second chamber 392. The branch 393A here extends vertically. The inlet 391A of the first chamber 391 is connected to an inlet 398 of the analysis unit 390.

A valve 405 may be provided on the supply channel 393.

It is noted that, in a manner not shown, a vent channel may be provided, connected to the second chamber 392 to let out air when the sample to be analyzed is introduced. The vent channel may be rendered hydrophobic to prevent also liquid from coming out. If the vent channel is connected to the external environment, to prevent any accidental exit or contamination of the surrounding environment, a filter, for example an EPA filter, may further be provided on the vent channel.

The second chamber 392 contains dried reagents 395, for example a mixture of reagents for performing real-time PCR, previously preloaded, in particular during the step described with reference to FIGS. 50C-50D and on the basis of the methodology described below. The first chamber 391 contains a sample to be analyzed 396 in liquid form, for example a biological sample or a derivative thereof, in particular the extracted nucleic acids and the elution liquid, as described with reference to FIGS. 1-19. The sample to be analyzed 396 is generally in excess with respect to the amount to be mixed with the dried reagents 395; the amount thereof might not be known precisely. The second chamber 392 thus forms an analysis chamber, where analysis of the sample to be analyzed 396 is carried out.

In FIG. 65B, a first force F1 is applied. The first force F1 may be exerted, as a thrust force, by an external pump (not shown), connected to the inlet 398 of the analysis unit 390, and/or may be a passive force (for example, exploiting capillarity) acting from the outlet 391B and/or may derive from a negative pressure (suction pressure) applied on the outlet end 397 of the supply channel 393 and transferred to the first chamber 391 through the supply channel 393.

The first force F1 causes the sample to be analyzed 396 to exit from the first chamber 391 through the outlet 391B thereof and fill the supply channel 393. By capillarity, the sample to be analyzed 396 also enters the second chamber 392.

When the sample to be analyzed 396 penetrates into the second chamber 392, it comes into contact with the dried reagents 395, which start to absorb it by hydrophilia (FIG. 65C), to form a sample/reagent mixture 399. The amount of sample to be analyzed 396 entering the second chamber 392 depends upon the amount of liquid that can be absorbed by the dried reagents 395 and is predetermined at the design stage, as discussed in detail hereinafter.

If so desired (FIG. 65D), the first chamber 391 and the supply channel 393 may be emptied by applying a second force F2 on the outlet end 397 of the supply channel 393. Alternatively, the second force F2 may be applied at the inlet 398 of the analysis unit 390. The second force F2 may be an active force, for example a positive or negative pressure generated by an external pump. The second chamber 392 is not emptied.

The analysis unit 390 of FIGS. 65A-65D may advantageously be used with the cartridge 2, 2' described with reference to FIGS. 1-19 and with the containment unit 350 described with reference to FIGS. 50-59. In particular, the first chamber 391 may be formed by the extraction chamber 6 (FIGS. 1-19), the second chamber 392 may be formed by the collector 8, 8' or by the analysis cell 354 in the reagent unit 350 of FIGS. 58-59, and the inlet 398 of the analysis unit 390 corresponds to the inlet fluidic recess 86. In this case, the analysis body 394 is formed by a number of parts, i.e., by the bodies 80-82 or 80'-82', which house the first chamber 391 (FIGS. 4 and 13), and by the reagent unit 350, accommodating the second chamber 392. The supply channel 393 may be formed by the output fluidic recess 88, by the product recess 99, 99', and by the through holes 100A, 100'.

Figures 66A, 66B, 66C, 66D:
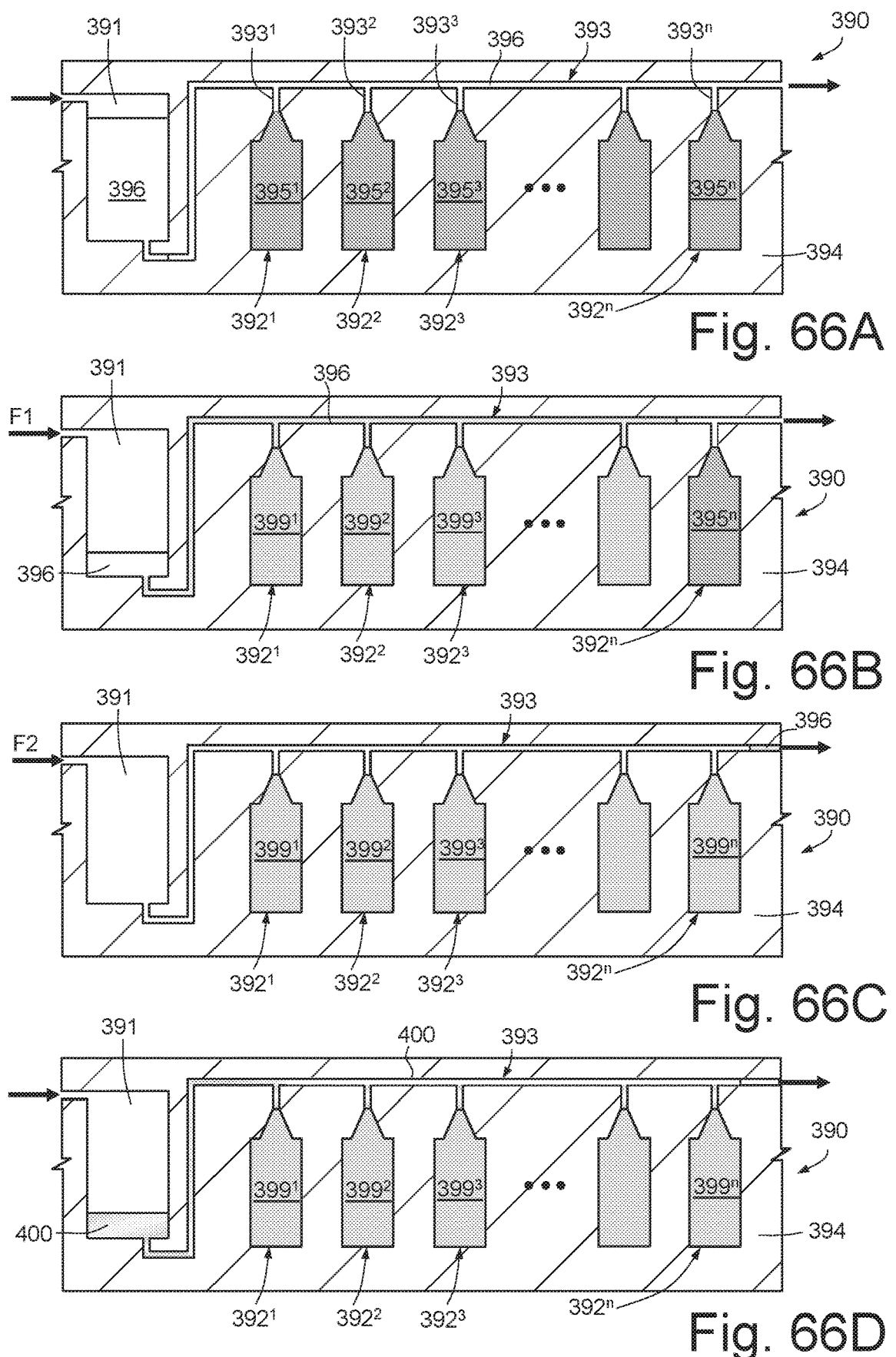
FIGS. 66A-66D show schematically a different analysis unit, in successive filling steps.

FIG. 66A shows a different embodiment of the analysis unit 390. In detail, the analysis unit 390 of FIG. 66A differs from the analysis unit 390 of FIG. 65A in that it comprises a plurality of second chambers or wells 392¹, 392², 393³, . . . , 392'', connected to the supply channel 393 through respective branches 393¹, 393², 393³, . . . , 393''.

Different dried reagents 395¹, 395², 395³, . . . , 395'' may be preloaded in the second chambers 392¹, 392², 393³, . . . , 392''. In this way, the analysis unit 390 can carry out different reactions starting from a same sample to be analyzed 396.

In FIG. 66B, the second chambers 392¹, 392², 393³, . . . , 392'' are loaded with the sample to be analyzed 396 contained in the first chamber 391; they are loaded in sequence on the basis of their arrangement along the supply channel 393, i.e., according to their distance from the first chamber 391, by applying the first force F1.

After loading the sample to be analyzed 396 (FIG. 66C), the supply channel 393 may be emptied by applying a second force F2, of an active type. A different sample/reagent mixture 399¹, 399², 399³, . . . , 399'' is thus contained in each second chamber 392¹, 392², 393³, . . . , 392'' present.

Then (FIG. 66D), the second chambers 392¹, 392², 393³, . . . , 392'' may be isolated from each other using an inert liquid non-mixable with the sample/reagent mixture 399, designated by 400, for example by loading mineral oil or liquid paraffin, or by melting some material, such as a low-melting paraffin wax, forming the walls of the second chambers 392', 392'', 392''', . . . , 392'', in a not shown manner.

The analysis unit 390 of FIGS. 66A-66D may be applied to the cartridge 2'' of FIGS. 60-64 using the containment unit 350 described with reference to FIGS. 50-57C. In this case, the first chamber 391 may be formed by the extraction chamber 6 (extraction recess 83), the second chambers 392¹, 392², 393³, . . . , 392'' correspond to the analysis cells 354 or to the reagent cavities 359, and the supply channel 393 corresponds to the fluidic channel 376 of FIG. 60, to the through hole 377, and to the recesses and holes 88, 388, and 100'' of FIGS. 63-64. In addition, in this case, for example, isolation between the second chambers 392¹, 392², 393³, . . . , 392'' may be obtained by melting the retention structure 375.

Figure 67:
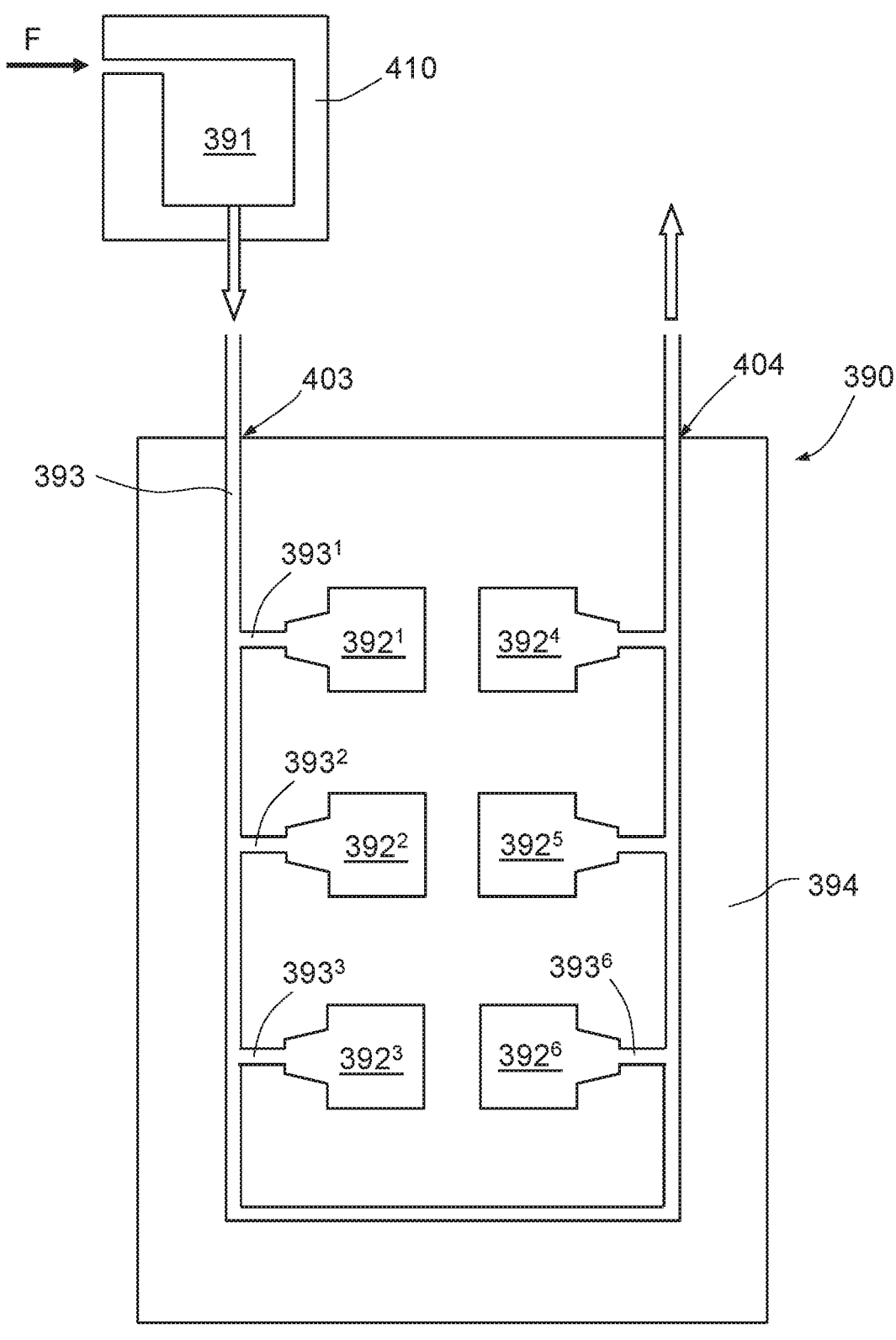
FIG. 67 shows a variant of the analysis unit of FIGS. 65 and 66.

FIG. 67 is a schematic illustration of an analysis unit 390 having a different arrangement of the second chambers 392. Here, moreover, the first chamber 391 is arranged in a separate unit 410. The analysis unit 390 of FIG. 67 has six second chambers 392¹, 392² 392³, . . . , 392⁶, even though the number may vary, and they are arranged in two vertical rows. The supply channel 393 thus has two branches series-connected, extending vertically, one of them defining an inlet 403 and the other defining an outlet 404 of the analysis unit 390.

Here, the second chambers 392¹, 392² 392³, . . . , 392⁶ are connected to the supply channel 393 through branches 393¹, 393², 393³, . . . , 393⁶ with horizontal extension.

For the rest, the analysis unit 390 is similar to the analysis unit 390 of FIGS. 65 and 66, and loading of the sample to be analyzed 396 (here not represented) is the same as described above with reference to these figures.

For instance, the analysis unit 390 may be formed by the reagent unit 350 of FIGS. 60-64, and the separate unit 410 may be formed by the cartridge 2'' shown in FIGS. 63 and 64.

In all of FIGS. 65-66, the second chambers 392, 392¹- 392'' may have a volume of for example 5-30 μl.

Obviously, the arrangement and the number of second chambers 392¹-392'', their volume, their connection to the supply channel 393, and their sequence on the supply channel 393 may vary as desired, according to the need.

To absorb the liquid sample to be analyzed, the capillarity of the branch or branches 393A, 393¹, . . . , 393'' is exploited, as mentioned above. The dimensions (radius and length) of these branches, and possibly also of the supply channel 393 (if it is desired to use only the capillarity as force F1) are appropriately calculated, according to the criteria referred to below.

For an estimate of the order of magnitude, Jurin's law is used, which describes the height of the meniscus of a liquid in a capillary tube, the top opening whereof is exposed to some known pressure and wherein gravity counters the rise of the meniscus (worst case). Even though the conditions of application are different, with some approximations it is possible to obtain a rough size estimate during design of the branches 393A, 393¹, . . . , 393'' and possibly of the supply channel 393.

In this estimate, the pressure of thrust or suction (force F1 of FIGS. 65B, 66A) is neglected, and it is assumed that the pressure in the capillary tube is constant.

In these conditions, the height of the liquid is given by:

$$h = \frac{2\gamma\cos\theta}{\rho g r} \tag{1}$$

where γ is the surface tension (in J/m² or N/m), θ is the contact angle between the surface of the liquid and the wall of the supply channel 393/393¹, . . . , 393'', p is the density of the liquid, g is the acceleration of gravity, and r is the radius of the supply channel 393/393¹, . . . , 393''.

If the liquid is water, Eq. (1) becomes:

$$h_{H_2O} = \frac{1.48\times10^{-5}}{r} \; [\mathrm{m}]$$

According to this model, with a supply channel 393/393¹, . . . , 393'' of radius r=1 mm, the height of the meniscus, and thus the useful length of the supply channel 393/393¹, . . . , 393'' for exploiting the capillarity is approximately 1.5 cm. This value represents in any case a rough estimate, and the design of the analysis unit 390 is made by including an empirical characterization.

In particular, in case of the analysis unit 390, the supply channel 393/393[1], . . . , 393" has a rectangular cross-section, typically with a base of 1 mm and a height of 0.5-1 mm. The maximum length of the supply channel 393/393[1], . . . , 393" is thus in the region of a few centimeters, compatible with the dimensions of the analysis unit 390, which allows just the force of capillarity (if so desired) to be exploited in the type of device here considered.

According to one aspect of the present disclosure, in all the analysis units 390 shown, the reaction reagents 395 in the second chambers 392 are contained in an alveolar reaction mass.

The alveolar reaction mass has a roughly spongy structure and has the aim of:

helping the dried reagents to remain in position during transport and storage of the analysis unit 390;

enabling loading of predetermined amounts of sample to be analyzed (the so-called "self-aliquoting"); and preventing or at least reducing cross-contamination between different dried reagents in different chambers and wells after re-hydrating the dried reagents with the sample to be analyzed, which is possible by virtue of the connection between the various chambers or wells.

For instance, when the analysis unit 390 is formed by or is incorporated in the cartridge 2, 2' or 2", the alveolar mass adheres to the support 351 and remains in position even after the retention structure 356, 375 has melt, as described with reference to FIGS. 57C and 60-65.

Because of the presence of the alveolar reaction mass, in the design stage the volume of the second chamber or chambers 392 is calculated taking into account not only the amount of sample to be analyzed that is to be absorbed, but also the possible swelling of the alveolar mass.

The alveolar reaction mass enables absorption of a preset amount of sample to be analyzed, provides greater stability to the dried reagents, holding them within the second chamber or chambers, and favors attraction of the sample to be analyzed, in liquid form.

This is all the more useful when the analysis unit 390, 390' forms the reagent unit 350 shown in FIGS. 63, 64, where the retention structure 375 melts during the thermal cycles. In this way, in fact, each reaction site is precisely defined, ensuring repeatability of the reaction, proper control of temperature, and correct analysis (detection step).

The alveolar reaction mass is typically obtained by lyophilization, which includes steps of freezing, primary drying and secondary drying the assay-specific reagents.

The alveolar mass is formed by one or more excipients having the aim of forming a matrix that receives the reagents to be dehydrated. The excipients are, for example, chosen in the group comprising: agarose, calcium alginate, polyacrylamide, hydroxyethyl cellulose, polyethylene glycol, and zeolites. In general, the excipient or excipients in question meets/meet the following requisites:

stable structure both during re-hydration and possibly as the temperature varies;

limited re-swelling; and hydrophilia, and more precisely capacity to absorb both the assay reagents and the sample.

The amount of liquid (sample to be analyzed) entering the second chambers 392 and absorbed by the alveolar mass depends upon:

the concentration of the excipient forming the alveolar mass in the initial solution that is lyophilized; the greater the amount of excipient, the greater the amount of dehydrated molecules of the excipient that can undergo hydration with the sample to be analyzed; in addition, as the amount of the excipient increases, the resistance of the alveolar mass increases, the alveolar mass can thus absorb a greater amount of sample to be analyzed without dissolving;

the degree of crosslinking, if the excipient is a polymer capable of crosslinking; crosslinked polymers are in general stiffer, and this fact may be useful in this application; the increase in the degree of crosslinking and thus of the stiffness of the alveolar mass enables the latter to absorb the sample to be analyzed without dissolving and with a lower re-swelling;

the ratio between the volume of the analysis chamber and the volume of the dried excipient: if the alveolar mass swells during re-hydration, this ratio becomes important; in fact, the absorption of liquid (sample to be analyzed) is interrupted when the alveolar mass occupies the entire volume of the reaction chamber during re-hydration.

It follows that, once the three parameters referred to above, which can be controlled, are fixed, the amount of sample to be analyzed that can be absorbed by the alveolar mass becomes "stoichiometric" in a precise and repeatable way.

The above amount may be calculated empirically by performing an experiment using a video camera with high frame rate and high resolution, so as to film re-hydration, step after step (for example, by adding 1 µl at each step), of the dried alveolar mass. When the alveolar mass stops absorbing the liquid sample, a part of the liquid starts to form a "shell" that surrounds the alveolar mass, and possibly this starts to lose its own shape (according to the characteristics of the mass). It has been shown by experiments of the present applicant that these phenomena are clearly visible and enable the exact amount of sample to be analyzed absorbed by the alveolar mass to be determined.

For instance, an alveolar mass obtained by lyophilization of 20 µl of an aqueous solution of agarose at 4% of mass of solute per volume of solution (w/V) absorbs 15 µl of water in a reaction chamber having a volume of 21.5 µl.

The alveolar mass may be produced using a multi-stage lyophilization process.

For instance, and in a non-limiting way, the process for producing the alveolar mass may comprise two steps:

1. first lyophilization of a solution containing the excipient or excipients and possible lyoprotectants (i.e., molecules that, combined with the excipients, prevent or substantially reduce chemical and physical instability of the reagents that are introduced in the subsequent step 2a during their lyophilization and subsequent storage); for instance, sugars, amino acids, methylamines, etc. may be used as lyoprotectants; in this step, an intermediate alveolar mass is formed; and 2a. introduction of a solution of assay-specific reagents, for example a mixture of real-time-PCR-specific reagents plus possible lyoprotectants, in the intermediate alveolar mass, and re-hydration of the excipient or excipients (plus possible lyoprotectants) lyophilized/ obtained in step 1 by the assay-specific reagents (plus possible lyoprotectants); and 2b. second lyophilization.

The first lyophilization may comprise, for example, four sub-steps:

a) preparation of a liquid solution of a precursor of the desired excipient (including possible lyoprotectants) monomeric or already in the polymeric form; for instance, an aqueous solution of agarose may be prepared, with a concentration of 2-10% in mass of solute per volume of solution (w/V);

b) freezing at a temperature of −40° C. to −80° C., for two hours;

c) primary drying (sublimation) for a time of 6-24 hours, at a very low pressure, for example 0.1 mbar; and d) secondary drying (desorption), which may last up to half of the duration of the previous step c). The secondary drying may be carried out, for example, at the pressure of 0.1 mbar by heating the plates of the lyophilizer at 30° C.

The second lyophilization (2b) may be carried out in a similar manner to what described for the first lyophilization.

At the end of the second lyophilization, an alveolar mass is obtained, which incorporates the assay-specific reagents.

The alveolar mass thus obtained may be introduced into the second chambers 393, 393$^{1}$-393$^{n}$; it is able to absorb a precise volume of re-hydration liquid (sample to be analyzed), as explained above.

Lyophilization in two separate steps is particularly advantageous since it enables maximum freedom of choice of the excipients (plus possible lyoprotectants) and of the reagents for the analysis, which may be developed, produced, and purchased independently, using protocols not shared between the manufacturer of the cartridge and the assay manufacturer. Furthermore, it enables a high final concentration (both of the assay-specific reagents and of the excipients plus possible lyoprotectants) to be obtained with values that cannot be achieved in a single lyophilization step.

As an alternative to the above, in some applications and for some assay reagents it is possible to carry out just one lyophilization wherein both the excipients intended to form the alveolar mass and the assay-specific reagents are dehydrated simultaneously.

When the reaction unit 390 forms the cartridge 2 or 2' of FIGS. 4-6 and 13-15, the intermediate alveolar mass or the alveolar mass may be produced directly within the analysis chamber 8, 8', prior to coupling, for example bonding or force fitting the body 80, 80' in the second closing wall 82, 82'. To this end, first the liquid solution of the excipient (as resulting from step a) described above) or the liquid solution of the assay-specific reagents is loaded in the analysis chamber 8, 8' using an automatic pipettor or by hand pipetting, and then lyophilization is carried out.

For the reaction unit 390, formed by the containment unit 350 of FIGS. 50-64, lyophilization(s) may be performed directly in the containment unit 350.

With the solution of FIGS. 64-66, it is possible to obtain an inexpensive and precise loading of a sample to be analyzed in an analysis chamber containing dried reagents in a simple way. The presence of the dried reagents in alveolar form enables loading to be obtained in precise amounts. The possible treatment to obtain the dried reagents in alveolar form using two lyophilization steps enables an increase in the concentration of dried reagents (excipient or excipients, possible lyoprotectants, and reagents for the analysis) and thus enables a high chemical and physical stability of the alveolar mass and a higher analysis efficiency. Furthermore, the described solution enables the manufacturer of the cartridge 2, 2', 2'' and the assay manufacturer not to share their own know-how, which is at times not public.

According to yet another aspect of the present disclosure, when the cartridge 2, 2' of FIGS. 1-19 integrates an analysis chamber 8, 8' wherein the analysis of the treated sample is carried out as described above, as in the case of the cartridge 2'' of FIGS. 63-64, the control machine 3, 3' is able to identify and automatically handle the intended type of analysis, as described hereinafter. It is noted that, even though hereinafter, for sake of simplicity, reference is made to the cartridge 2 and to the control machine 3, the following explanation also applies to the cartridge 2' of FIGS. 13-19 and to the cartridge 2'' of FIGS. 63 and 64, as well as to the machine 3' of FIGS. 11-12.

In particular, to enable automatic handling of the analysis, data regarding the analysis for which the cartridge 2 is designed are stored on the cartridge 2, also considering the specific reagents for the sample contained in the analysis chamber 8.

Figure 68:
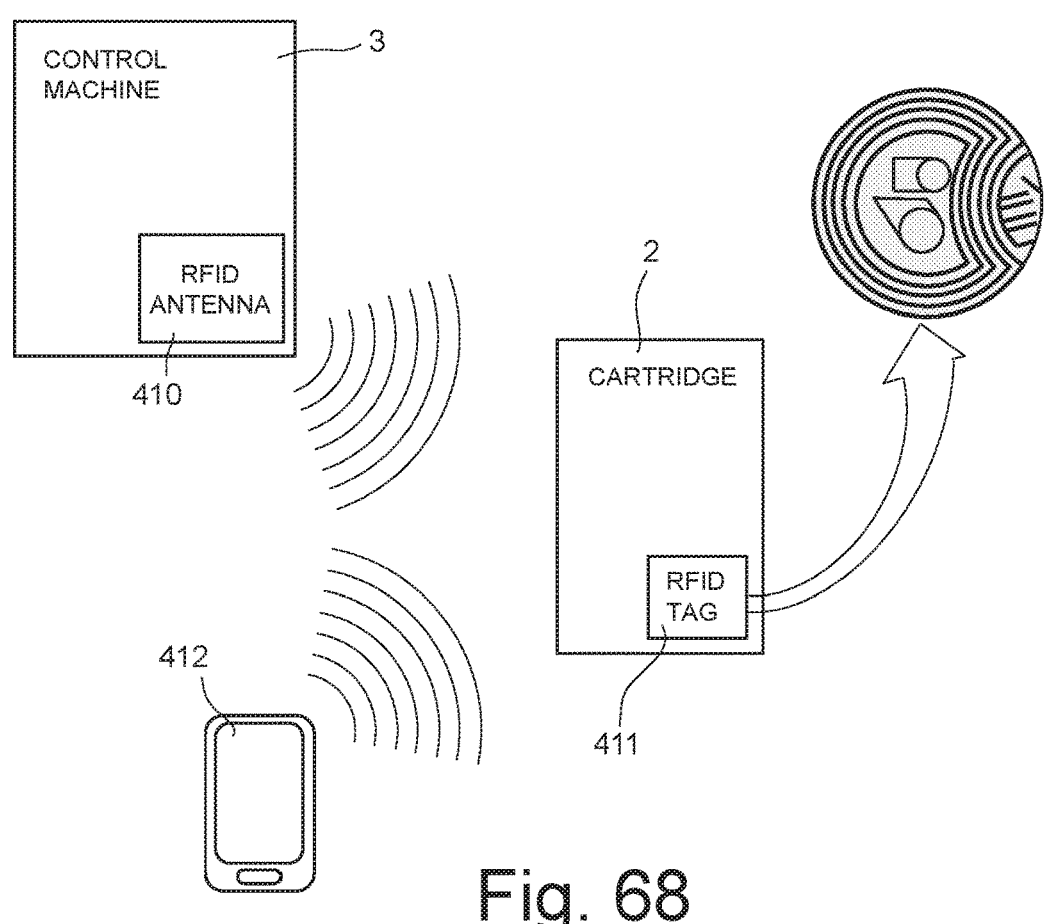
FIG. 68 shows schematically a communication mode used in the present system and toward the outside world.

To this end (FIG. 68), the machine 3 comprises a radiofrequency antenna 410 coupled to the control unit 35, and the cartridge 2 has an RFID (Radio-Frequency Identification) tag 411. The RFID tag 411 is typically of a passive type and is arranged on the casing 5 or co-molded with the casing 5 and comprises an antenna and a writing substrate, as known (and not shown).

In particular, the RFID tag 411 contains information on the type of cartridge 2, including:

number of analysis chambers or wells 8, 354, 359 contained in the cartridge 2 or in the containment unit 350/analysis unit 390 of FIGS. 50-67;

type of analysis to be performed in the cartridge 2;

expiry date of the cartridge 2; and traceability data, regarding, for example, production and functionalization of the cartridge 2.

The RFID tag 411 may be read by the control machine 3, using its own radio-frequency antenna 410 or using a mobile device 412, for example a cellphone, through a common NFC (Near-Field Communication) interface.

Figures 69, 70:
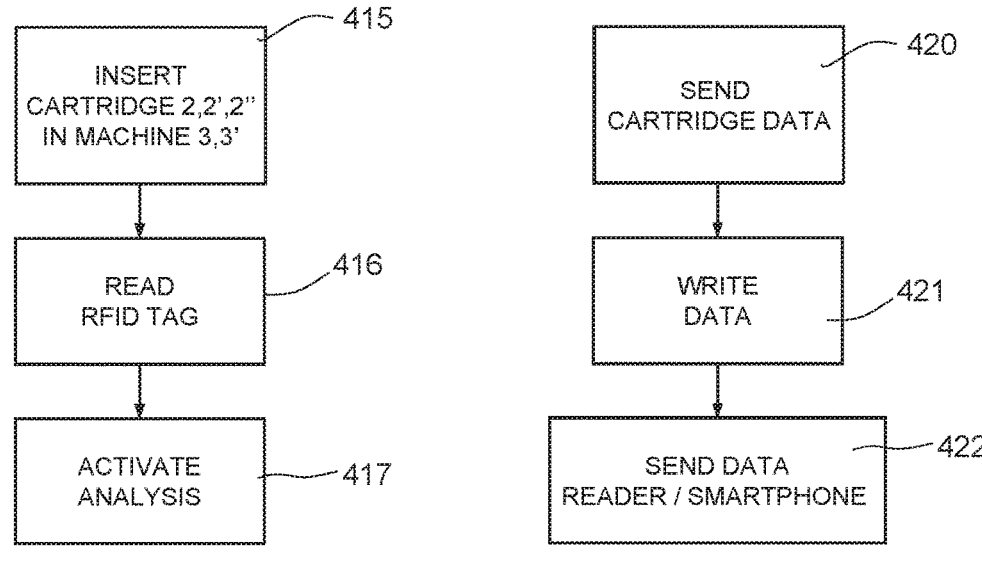
FIG. 69 is a flowchart of communications between the control machine and the cartridge in the present system.
FIG. 70 is a flowchart of communications between the cartridge and an external device.

Typically, the RFID tag 411 interacts with the control machine 3 before and after performing an analysis; it interacts with the mobile device 412 after performing an analysis, as represented in the flow charts of FIGS. 69 and 70.

In particular, when it is desired to carry out an analysis (FIG. 69), the cartridge 2 is inserted in the control machine 3 (step 415), the control machine 3 reads the information stored in the RFID tag 411, referred to above (step 416), and, on the basis of the information read, the control machine 3 is able to start the intended operations for the correct type of analysis, which include the sample preparation (for example, coupling of chambers 46 in the desired sequence, activating the actuators 40-43, the pump 25, the heaters 48, etc., as described with reference to FIGS. 7-10, or similar operations described with reference to FIGS. 16-19). Then, the machine 3 may perform the proper analysis operations, and read the results, in a per se known manner.

After analysis (FIG. 70), the control machine 3 sends the results of the analysis to the cartridge 2 through its own antenna 410 (step 420). The cartridge 2 receives and writes these results through its own RFID tag 411 (step 421). These data may then be read at any moment, for example via the cellphone 412 having an NFC (Near-Field Communication) protocol (step 422).

In this way, the results of the analysis may be stored and read after quite some time, facilitating handling of the stored data. In fact, if these data were stored for example in the cloud, access might be far from practical. For instance, due to the large number of performed analyses, the identifiers, provided to the users, would be very long and thus far from practical to use.

The data could be protected by encryption algorithms, to safeguard the privacy of the patients.

Finally, it is clear that modifications and variations may be made to the solutions described and illustrated herein, without thereby departing from the scope of the present disclosure. For instance, the various described embodiments may be combined to provide further solutions.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
a cartridge for sample preparation and molecule analysis, the cartridge including:
a body including:
a first surface;
a second surface opposite to the first surface;
an extraction recess that extends into the second surface;
an analysis recess that extends into the second surface, the analysis recess having a parallelepipedal shape with rounded corners at an end of the analysis recess; and
a waste opening;
a first closing wall coupled to the first surface of the body, the first closing wall including a waste recess that is aligned with and overlaps the waste opening, the waste recess is in fluid communication with the waste opening;
a second closing wall coupled to the second surface of the body, the second closing wall including a chip receiving opening in the second closing wall, and the second closing wall including one or more first sidewalls that define and delimit the chip receiving opening; and
a chip within the chip receiving opening, the chip is aligned with and fully overlaps the analysis recess in the body closing off sides of the analysis recess such that a first surface of the chip and respective sides of the analysis recess delimit an analysis chamber, the chip including one or more second sidewalls that abut the one or more first sidewalls, the one or more second sidewalls being spaced apart outward from respective sides of the analysis recess and the analysis chamber is configured to, in operation, collect a solution including assay reagents such that first surface of the chip is exposed to an analysis sample.

2. The device of claim 1, wherein the chip includes a heating and temperature control element configured to, in operation, heat the solution in the analysis recess.

3. The device of claim 2, wherein the chip includes one or more first sidewalls that are transverse to the first surface of the chip, and the one or more second sidewalls of the second closing wall that delimit and define the chip receiving opening.

4. The device of claim 1, wherein the chip includes:
a second surface that faces away from the analysis recess, and the second surface is opposite to the first surface of the chip;
an electrical contact that is on the second surface of the chip; and
a heating and temperature control element configured to, in operation, heat a solution in the analysis recess.

5. The device of claim 1, wherein:
the extraction recess includes a first end and a second end opposite to the first end;
the body further includes:
a first valve hole that extends through the body from the first surface to the second surface;
a second valve hole that extends through the body from the first surface to the second surface, the second valve hole is closer to the analysis recess than the first valve hole; and
a third valve hole that extends through the body from the first surface to the second surface, the third valve hole is closer to the analysis recess than the first valve hole and the second valve hole;
the cartridge further includes:
a first magnetic shutter in the first valve hole;
a second magnetic shutter in the second valve hole; and
a third magnetic shutter in the third valve hole.

6. The device of claim 5, wherein:
the first magnetic shutter includes an opened position in which the first end of the extraction recess is in fluid communication with the waste opening and the waste recess;
the second magnetic shutter includes an opened position in which the second end of the extraction recess is in fluid communication with the waste opening and the waste recess; and
the third magnetic shutter includes an opened position in which the analysis recess is in fluid communication with the waste opening and the waste recess.

7. The device of claim 5, wherein:
the body includes a first edge and a second edge transverse to the first edge;
the first valve hole is between the first edge of the body and the second valve hole, the first valve hole includes a first center;
the second valve hole is between the first valve hole and the third valve hole, the second valve hole includes a second center;
the third valve hole is between the second valve hole and the analysis recess, the third valve hole includes a third center; and
the center of the first valve hole, the center of the second valve hole, and the center of the third valve hole are aligned along an axis that is substantially parallel to the second edge.

8. The device of claim 7, wherein the analysis recess is along the axis.

9. A device, comprising:
a cartridge for sample preparation and molecule analysis, the cartridge including:
a body including:
a first main face and a second main face opposite to the first main face;
a first sidewall extends from the first main face to the second main face;
a second sidewall extends from first main face to the second main face, the second sidewall is opposite to the first sidewall;
a third sidewall extends from the first main face to the second main face, the third sidewall is opposite to the first sidewall;
an inlet at the second sidewall and an outlet at the third sidewall;
a waste chamber;
a plurality of reagent chambers separated from the waste chamber by a plurality of first partition walls, each one of the plurality of reagent chambers is separated from an adjacent one of the plurality of reagent chambers by one of the plurality of first partition walls; and an analysis recess separated from waste chamber by a second partition wall, the analysis recess extends into the second main face, and the analysis recess has a parallelepipedal shape having rounded corners at an end of the analysis recess;

a first closing wall coupled to the first main face;

a second closing wall coupled to the second main face, the second closing wall including a chip receiving opening, and the second closing wall including one or more first sidewalls that define and delimit the chip receiving opening; and a chip within the chip receiving opening, the chip is coupled to the second main face, the chip fully overlaps the analysis recess, the chip includes a first surface that closes off sides of the analysis recess, the chip including one or more second sidewalls that abut the one or more first sidewalls, the one or more second sidewalls of the chip are spaced outward from the sides of the analysis recess, and the first surface of the chip and the sides of the analysis recess delimit and define an analysis chamber such that the first surface of the chip is exposed to an analysis sample when present within the analysis chamber.

10. The device of claim 9, wherein:

the body further includes:

an extraction recess, and the extraction recess includes a first end and a second end opposite to the first end;

a vent recess within the body and separated from the waste chamber by a third partition wall;

a first valve hole extends into the second main face of the body to the waste chamber;

a second valve hole extends into the second main face of the body to the waste chamber, the second valve hole is closer to the analysis recess than the first valve hole; and a third valve hole extends into the second main face of the body to the vent recess, the third valve hole is closer to the analysis recess than the first valve hole and the second valve hole;

the cartridge further includes:

a first magnetic shutter in the first valve hole;

a second magnetic shutter in the second valve hole; and a third magnetic shutter in the third valve hole.

11. The device of claim 10, wherein:

the first magnetic shutter includes an opened position in which the second end of the extraction recess is in fluid communication with the waste chamber;

the second magnetic shutter includes an opened position in which the first end of the extraction recess is in fluid communication with the waste chamber; and the third magnetic shutter includes an opened position in which the analysis chamber is in fluid communication with the vent recess.

12. The device of claim 10, wherein;

the body includes a first edge and a second edge transverse to the first edge;

the first valve hole is between the first edge of the body and the second valve hole, the first valve hole includes a first center;

the second valve hole is between the first valve hole and the third valve hole, the second valve hole includes a second center;

the third valve hole is between the second valve hole and the analysis recess, the third valve hole includes a third center; and the center of the first valve hole, the center of the second valve hole, and the center of the third valve hole are aligned along an axis that is substantially parallel to the second edge.

13. The device of claim 9, wherein the chip includes:

a second surface that faces away from analysis recess, and the second surface is opposite to the first surface of the chip;

an electrical contact that is on the second surface of the chip; and a heating and temperature control element configured to, in operation, heat a solution within the analysis recess.

14. The device of claim 9, wherein the body further comprises:

an extraction recess having a first end and a second end opposite to the first end;

an inlet recess in fluid communication with the inlet and the second end of the extraction recess, the inlet recess extends from the inlet to the extraction recess; and a plurality of reagent holes are in fluid communication with the inlet recess and the plurality of reagent chambers, each one of the plurality of reagent holes extends to one of the plurality of reagent chambers, and the plurality of reagent holes extend along the inlet recess.

15. The device of claim 14, further comprising a plurality of one-shot valves that close off the plurality of reagent holes, each one of the plurality of one-shot valves closes off one of the plurality of reagent holes.

16. The device of claim 15, wherein the plurality of one-shot valves include a material that melts when exposed to heat.

17. A device, comprising:

a cartridge for sample preparation and molecule analysis, the cartridge including:

a body including:

a first side;

a second side opposite to the first side;

an extraction recess that extends into the second side;

an analysis recess that extends into the second side, the analysis recess includes a parallelepipedal shape and an end having rounded corners;

a waste opening that extends into the second side to the first side, the waste opening extends entirely through the body; and one or more valve holes that extend into the second side to the first side, the one or more valve holes extend entirely through the body;

a first closing wall coupled to the first side of the body, the first closing wall including:

a waste recess in fluid communication with the waste opening;

a first gasket cavity; and a second gasket cavity;

a first gasket in the first gasket cavity;

a second gasket in the second gasket cavity;

a second closing wall coupled to the second side of the body, the second closing wall including a chip receiving opening, and the second closing wall including one or more first sidewalls that define and delimit the chip receiving opening; and a chip within the chip receiving opening, the chip is aligned with and overlaps the analysis recess, the chip is coupled to the second side of the body, the chip includes a heating and temperature control element, configured to, in operation, heat a solution in the analysis recess, and the chip closes off sides of the analysis recess delimiting an analysis chamber with the analysis recess and the chip, one or more second sidewalls of the chip abut the one or more first sidewalls of the second closing wall, and the one or more second sidewalls of the chip are spaced outward from the sides of the analysis recess, and a first surface of the chip and the sides of the analysis recess delimit the analysis chamber, and the first surface of the chip is exposed to the solution when in the analysis recess.

18. The device of claim 17, wherein one or more magnetic shutters are in the one or more valve holes, each respective magnetic shutter of the one or more magnetic shutters is in a corresponding valve hole of the one or more valve holes.

19. The device of claim 17, wherein the body further includes a first fluid passageway in fluid communication with the first gasket cavity and the extraction recess.

20. The device of claim 18, wherein:

the body includes a first portion of a second passageway;

the first closing wall includes a second portion of the second passageway, the second portion is in fluid communication with the first portion; and the second passageway is in fluid communication with the second gasket cavity and the waste recess.

* * * * *